US010792438B2

(12) United States Patent
Sanders et al.

(10) Patent No.: US 10,792,438 B2
(45) Date of Patent: Oct. 6, 2020

(54) SAFETY NEEDLE DEVICES

(71) Applicant: Becton, Dickinson and Company, Franklin Lakes, NJ (US)

(72) Inventors: Laurie Sanders, Glen Ridge, NJ (US); Peter Smith, Cary, NC (US); Edward P. Browka, Oneida, NY (US); Eli B. Nichols, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 121 days.

(21) Appl. No.: 15/837,756

(22) Filed: Dec. 11, 2017

(65) Prior Publication Data

US 2018/0161521 A1 Jun. 14, 2018

Related U.S. Application Data

(60) Provisional application No. 62/533,786, filed on Jul. 18, 2017, provisional application No. 62/479,507,
(Continued)

(51) Int. Cl.
*A61M 5/32* (2006.01)
*A61B 5/15* (2006.01)

(52) U.S. Cl.
CPC .......... *A61M 5/3245* (2013.01); *A61M 5/326* (2013.01); *A61M 5/3243* (2013.01);
(Continued)

(58) Field of Classification Search
CPC .............. A61M 5/3271; A61M 5/3243; A61M 5/3272; A61M 5/321; A61M 5/3257;
(Continued)

(56) References Cited

U.S. PATENT DOCUMENTS 3,367,488 A 2/1968 Hamilton
3,869,062 A 3/1975 Jaeschke et al.
(Continued)

FOREIGN PATENT DOCUMENTS

CA 2551835 A1 8/2005
CA 2803761 A1 12/2011
(Continued)

OTHER PUBLICATIONS

Final Office Action in U.S. Appl. No. 15/837,018 dated Jun. 18, 2019, 15 pages.
(Continued)

*Primary Examiner* — Nilay J Shah
(74) *Attorney, Agent, or Firm* — Servilla Whitney LLC

(57) ABSTRACT

A safety needle device is disclosed having a hub, needle cannula, housing, tether, retractable sleeve, locking member and spring element. The tether is movably disposed in the housing, the tether having a slot with an enlarged first guide path and a narrowed second guide path extending distally from the enlarged first guide path. The retractable sleeve is configured to move from an initial position to partially expose a distal tip of the needle cannula, a retracted position to fully exposes the needle cannula, and an extended position to fully cover the distal tip of the needle cannula. The proximal movement of one or more protrusions on the retractable sleeve, rotates the tether to move the at least one or more protrusions from the enlarged first guide path of the tether to the narrowed second guide path of the tether, this rotation activating the device.

32 Claims, 47 Drawing Sheets

Related U.S. Application Data filed on Mar. 31, 2017, provisional application No. 62/433,294, filed on Dec. 13, 2016, provisional application No. 62/433,350, filed on Dec. 13, 2016.

(52) U.S. Cl.
CPC ........ *A61M 5/3257* (2013.01); *A61M 5/3271* (2013.01); *A61M 5/3272* (2013.01); *A61B 5/150656* (2013.01); *A61M 5/321* (2013.01); *A61M 2005/325* (2013.01); *A61M 2005/3267* (2013.01)

(58) Field of Classification Search
CPC ........ A61M 5/3202; A61M 2005/3249; A61M 2005/3267; A61B 5/15003; A61B 5/150633; A61B 5/150641; A61B 5/150648; A61B 5/150656
See application file for complete search history.

(56) References Cited

U.S. PATENT DOCUMENTS

| | | | | |
|---|---|---|---|---|
| 4,610,667 | A | 9/1986 | Pedicano et al. | |
| 4,795,432 | A | 1/1989 | Karczmer | |
| 4,813,940 | A | 3/1989 | Parry | |
| 4,950,250 | A | 8/1990 | Haber | |
| 5,084,028 | A | 1/1992 | Kennedy et al. | |
| 5,330,899 | A | 7/1994 | Devaughn | |
| 5,336,199 | A | 8/1994 | Castillo et al. | |
| 5,395,347 | A | 3/1995 | Blecher | |
| 5,415,645 | A | 5/1995 | Friend et al. | |
| 5,591,138 | A | 1/1997 | Vaillancourt | |
| 5,688,241 | A | 11/1997 | Asbaghi | |
| 5,984,899 | A | 11/1999 | D'Alessio | |
| RE36,885 | E | 9/2000 | Blecher | |
| 6,884,237 | B2 | 4/2005 | Asbaghi | |
| 6,926,697 | B2 | 8/2005 | Malenchek | |
| 7,134,550 | B2 | 11/2006 | Groth | |
| 7,320,682 | B2 * | 1/2008 | Cocker | A61M 5/326 604/110 |
| 7,361,159 | B2 | 4/2008 | Fiser | |
| 7,513,888 | B2 | 4/2009 | Sircom | |
| 7,665,605 | B2 | 2/2010 | Erickson et al. | |
| 7,811,261 | B2 | 10/2010 | Rubinstein | |
| 7,871,397 | B2 | 1/2011 | Schraga | |
| 8,062,265 | B2 | 11/2011 | Millerd | |
| 8,162,882 | B2 | 4/2012 | Rubinstein | |
| 8,303,541 | B2 | 11/2012 | Chun | |
| 8,333,738 | B2 | 12/2012 | Millerd | |
| 8,439,870 | B2 | 5/2013 | Moyer | |
| 8,496,627 | B2 | 7/2013 | Chelak | |
| 8,636,688 | B2 | 1/2014 | Shaw | |
| 8,636,703 | B2 | 1/2014 | Foshee | |
| 8,647,307 | B2 | 2/2014 | Gratwohl | |
| 8,663,129 | B2 | 3/2014 | Allen | |
| 8,747,355 | B2 | 6/2014 | Rubinstein | |
| 8,827,961 | B2 | 9/2014 | Emmott | |
| 8,968,241 | B2 | 3/2015 | Liversidge | |
| 8,979,794 | B2 | 3/2015 | Chevallier | |
| 9,050,416 | B2 | 6/2015 | Feret | |
| 9,061,106 | B2 | 6/2015 | Roberts | |
| 9,067,024 | B2 | 6/2015 | Roberts | |
| 9,186,466 | B2 | 11/2015 | Zachek | |
| 9,352,099 | B2 | 5/2016 | Roberts | |
| 9,352,100 | B2 | 5/2016 | Ward | |
| 9,352,101 | B2 | 5/2016 | Roberts | |
| 9,370,327 | B2 | 6/2016 | Teoh | |
| 9,408,632 | B2 | 8/2016 | Erskine | |
| 9,445,760 | B2 | 9/2016 | Allen | |
| 9,694,140 | B2 | 7/2017 | Rubinstein | |
| 9,848,810 | B2 | 12/2017 | Allen | |
| 2001/0031949 | A1 * | 10/2001 | Asbaghi | A61M 5/326 604/198 |
| 2002/0063074 | A1 | 5/2002 | Simm et al. | |
| 2002/0165497 | A1 | 11/2002 | Greene | |
| 2003/0093009 | A1 | 5/2003 | Newby et al. | |
| 2003/0120209 | A1 * | 6/2003 | Jensen | A61M 5/326 604/110 |
| 2003/0121815 | A1 | 7/2003 | Bergeron et al. | |
| 2003/0181867 | A1 * | 9/2003 | Bressler | A61M 25/0625 604/263 |
| 2003/0181869 | A1 | 9/2003 | Swenson et al. | |
| 2005/0067309 | A1 | 3/2005 | Choi | |
| 2005/0113750 | A1 * | 5/2005 | Targell | A61M 5/326 604/110 |
| 2005/0119627 | A1 | 6/2005 | Crawford | |
| 2005/0279664 | A1 | 12/2005 | Hommann | |
| 2006/0189933 | A1 | 8/2006 | Alheidt et al. | |
| 2006/0189934 | A1 | 8/2006 | Kuracina et al. | |
| 2006/0213793 | A1 | 9/2006 | Brand | |
| 2009/0024093 | A1 | 1/2009 | Carrel et al. | |
| 2009/0254042 | A1 * | 10/2009 | Gratwohl | A61M 5/326 604/198 |
| 2009/0299295 | A1 | 12/2009 | Rubinstein et al. | |
| 2010/0298770 | A1 | 11/2010 | Rubinstein | |
| 2011/0288491 | A1 | 11/2011 | Newman et al. | |
| 2011/0319817 | A1 | 12/2011 | Rubinstein et al. | |
| 2012/0029440 | A1 | 2/2012 | Boyd et al. | |
| 2014/0048433 | A1 | 2/2014 | Dasbach et al. | |
| 2014/0097111 | A1 | 4/2014 | Dasbach et al. | |
| 2014/0135706 | A1 | 5/2014 | Rubinstein | |
| 2014/0228772 | A1 | 8/2014 | Ward | |
| 2014/0364803 | A1 | 12/2014 | Rubinstein | |
| 2015/0034516 | A1 | 2/2015 | Chapin et al. | |
| 2015/0094659 | A1 | 4/2015 | Schraga | |
| 2015/0165132 | A1 | 6/2015 | Perot et al. | |
| 2015/0182704 | A1 | 7/2015 | Chevallier | |
| 2015/0190580 | A1 | 7/2015 | Imai | |
| 2015/0190586 | A1 | 7/2015 | Takemoto | |
| 2015/0297837 | A1 | 10/2015 | Schraga | |
| 2015/0297881 | A1 | 10/2015 | Sanders et al. | |
| 2016/0074572 | A1 | 3/2016 | Spool et al. | |
| 2016/0303331 | A1 | 10/2016 | Evans et al. | |
| 2017/0106136 | A1 | 4/2017 | Dibiasi | |
| 2017/0233168 | A1 | 8/2017 | Horvath et al. | |
| 2018/0161490 | A1 | 6/2018 | Sanders et al. | |
| 2018/0161492 | A1 | 6/2018 | Sanders et al. | |
| 2018/0161521 | A1 | 6/2018 | Sanders et al. | |

FOREIGN PATENT DOCUMENTS

| | | | |
|---|---|---|---|
| CN | 103079610 | A | 5/2013 |
| EP | 0734739 | A2 | 10/1996 |
| EP | 0750915 | A2 | 1/1997 |
| EP | 1537890 | A1 | 6/2005 |
| EP | 1949928 | A1 | 7/2008 |
| EP | 2585146 | B1 | 3/2017 |
| FR | 2884723 | A1 | 10/2006 |
| FR | 2930160 | A1 | 10/2009 |
| JP | 2007519474 | A | 7/2007 |
| JP | 2013529973 | A | 7/2013 |
| MX | 2013/000081 | A | 3/2013 |
| MX | 349289 | B | 7/2017 |
| WO | 92/06725 | A1 | 4/1992 |
| WO | 2008050158 | A2 | 5/2008 |
| WO | 2009040602 | A1 | 4/2009 |
| WO | 2009/114777 | A1 | 9/2009 |
| WO | 2010/033767 | A2 | 3/2010 |
| WO | 2012/000833 | A1 | 1/2012 |
| WO | 2012/013587 | A1 | 2/2012 |
| WO | 2015/164416 | A1 | 10/2015 |
| WO | 2016/087187 | A1 | 6/2016 |

OTHER PUBLICATIONS

Non-Final Office Action in U.S. Appl. No. 15/837,008 dated Jul. 25, 2019, 23 pages.
PCT International Search Report and Written Opinion in PCT/US2017/065688 dated Feb. 26, 2018, 13 pages.
PCT Invitation to Pay Additional Fees, and, Where Applicable, Protest Fee dated Feb. 20, 2018, 12 pages.

(56) References Cited

OTHER PUBLICATIONS

PCT Invitation to Pay Additional Fees, and, Where Applicable, Protest Fee in PCT/US2017/065718 dated Apr. 9, 2018, 13 pages.
PCT International Search Report and Written Opinion in PCT/US2017/065692 dated Mar. 13, 2018, 14 pages.
PCT International Search Report and Written Opinion in PCT/US2017/065693 dated Mar. 7, 2018, 12 pages.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
"PCT International Search Report and Written Opinion in PCT/US2017/065718 dated Jan. 2, 2019", 18 pgs.
PCT International Preliminary Report on Patentability in PCT/US2017/065688 dated Jun. 27, 2019, 9 pages.
PCT International Preliminary Report on Patentability in PCT/US2017/065689 dated Jun. 27, 2019, 10 pages.
PCT International Preliminary Report on Patentability in PCT/US2017/065692 dated Jun. 27, 2019, 8 pages.
PCT International Preliminary Report on Patentability in PCT/US2017/065693 dated Jun. 27, 2019, 7 pages.
PCT International Preliminary Report on Patentability in PCT/US2017/065716 dated Jun. 27, 2019, 9 pages.
PCT International Preliminary Report on Patentability in PCT/US2017/065717 dated Jun. 27, 2019, 9 pages.
PCT International Preliminary Report on Patentability in PCT/US2017/065718 dated Jun. 27, 2019, 12 pages.
Non-Final Office Action in U.S. Appl. No. 15/837,011 dated Oct. 7, 2019, 8 pages.
Non-Final Office Action in U.S. Appl. No. 15/837,748 dated Oct. 17, 2019, 19 pages.
Non-Final Office Action in U.S. Appl. No. 15/837,810 dated Oct. 17, 2019, 27 pages.
Non-Final Office Action in U.S. Appl. No. 15/837,018 dated Dec. 5, 2019, 14 pages.
Final Office Action in U.S. Appl. No. 15/837,748 dated Feb. 28, 2020, 19 pages.
Final Office Action in U.S. Appl. No. 15/837,810 dated Feb. 28, 2020, 24 pages.
Non-Final Office Action in U.S. Appl. No. 15/837,020 dated Feb. 3, 2020, 11 pages.

* cited by examiner

SAFETY NEEDLE DEVICES

CROSS-REFERENCE TO RELATED APPLICATIONS

This application claims priority under 35 U.S.C. § 119(e) to U.S. Provisional Application No. 62/433,294, filed Dec. 13, 2016, U.S. Provisional Application No. 62/433,350, filed Dec. 13, 2016, U.S. Provisional Application No. 62/479,507, filed Mar. 31, 2017, and U.S. Provisional Application No. 62/533,786, filed Jul. 18, 2017, the disclosures of which are incorporated herein by reference in their entirety.

TECHNICAL FIELD

The present disclosure relates generally to safety needle devices, and specific embodiments pertain to single-use passive safety needle devices.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior safety needle devices include various disadvantages including a retractable sleeve which requires one or more of long stroke distances to activate the safety feature, multi-component retraction and locking elements, and creation of an undesirable significant force against a patient's skin during activation of the safety feature upon receiving an injection. In addition, conventional retraction syringe assemblies often do not incorporate reuse prevention features, and thus, the retraction mechanism of the syringe may be reset so the syringe barrel may be reused. The reuse of syringe assemblies without sterilization or sufficient sterilization is believed to facilitate the transfer of contagious diseases. Further, the retraction features of conventional syringes may also require the user to actively activate the retraction mechanism. Accordingly, the chance of human error in failure to activate or properly activate the retraction mechanism can lead to continued exposure of needles leading to needle stick injuries.

Existing retracting sleeve safety needle devices also may include a single-use safety needle device assembly that obscures a substantial majority or an entirety of an injection needle from view before, during, and after an injection procedure. However, many injection procedures require that the practitioner know precisely the location and depth to which the needle is inserted in the patient's tissue to be sure that medication is delivered to an appropriate location. In addition, many users falsely assume that they were "safe" from needle stick injuries, even when the safety needle devices are in the non-locked initial state, due to the tip of the prior art retracting sleeve safety needle devices being fully covered in an unlocked state.

Thus, there is a need to provide a safety needle device having an activation mechanism that overcomes one or more of the deficiencies of existing retractable sleeve safety needle devices. It may also be desirable to provide a safety needle device that can provide one or more of activation over a shorter stoke distance, ease of use, increased patient comfort, low part count, minimal part complexity, relatively compact design and relatively short overall length, minimal to no sleeve rotation against a patient's skin, and clear and unobstructed view of the needle in an initial position prior to injection into a patient.

SUMMARY

One aspect of the present disclosure pertains to a safety needle device comprising a hub having a proximal end that can be coupled to a syringe, the hub having a needle cannula extending therefrom in a distal direction, the needle cannula having a longitudinal axis and distal tip; a housing having a proximal end, a distal end, and a housing body, the hub being attached to the housing and the distal tip extending past the distal end of the housing; a needle cannula cover comprising an elongate sleeve having a distal end, the needle cannula cover slidably movable in a distal and proximal direction inside the housing and being biased to move in a distal direction toward the distal tip of the needle cannula, the needle cannula cover having an initial starting position at which the distal tip of the needle cannula is exposed, an intermediate position at which the needle cannula cover is moved in a proximal direction to move the distal end of the needle cannula cover a distance further from the distal tip of the needle cannula, and an extended position at which the distal end of the needle cannula cover extends past the distal tip of the needle cannula to cover the distal tip; and a clip disposed adjacent the distal end of the needle cannula cover, the clip preventing proximal movement of the sleeve and exposure of the distal tip of the needle cannula.

A second aspect pertains to a safety needle device comprising: a hub having a proximal end that can be coupled to a syringe, the hub having a needle cannula extending therefrom in a distal direction, the needle cannula having a longitudinal axis and distal tip; a housing having a proximal end, a distal end, and a housing body, the hub being attached to the housing and the needle cannula and the distal tip extending past the distal end of the housing; an activation component that can move axially and radially with respect to the housing, the activation component telescopically engaged with the housing; and a needle cannula cover that can move axially with respect to the housing and the activation component, the needle cannula cover telescopically engaged with the activation component, the needle cannula cover comprising a peg engaged in a slot in the activation component to activate the needle cannula cover, causing the needle cannula cover to be moved in a distal direction.

Another aspect pertains to a safety needle device comprising: a hub having a proximal end that can be coupled to a syringe and a distal end supporting a needle cannula having a longitudinal axis and distal tip extending from the hub; a housing having a proximal end, a distal end, and a housing body, the hub being attached to the housing adjacent the proximal end and the needle cannula and the distal tip extending past the distal end of the housing; a needle cannula cover comprising an elongate sleeve having a distal end having an opening therein, the sleeve axially movable in a distal and proximal direction inside the housing and being biased to move in a distal direction to cover the distal tip of the needle cannula, the opening allowing the distal tip to pass therethrough when the sleeve is moved in a proximal direction; and a biased clip disposed adjacent the distal end of the elongate sleeve, the sleeve having a gate that is biased by a biasing element to a closed position to cover the opening when the cover is moved in a proximal direction and the distal tip of the needle cannula passes through the opening, the gate held in an open position by the needle cannula.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

In this disclosure, a convention is followed wherein the distal end of the device is the end closest to a patient and the proximal end of the device is the end away from the patient and closest to a practitioner. As used herein, a "front view" refers to a view of the distal end of the device, and a "rear view" refers to a view of the proximal end of the device.

As used herein, a "safety needle device" refers to a device having a needle suitable for injection that includes one or more features to prevent needle stick injuries. As used herein, a "passive safety needle" refers to a safety needle device with a passive activation mechanism that has a sheath or sleeve that automatically covers the distal end of the needle after a patient has been injected. Thus, "passive" refers to the fact that the needle is shielded by a sleeve or sheath automatically after the needle cannula is removed from a subject or patient. A practitioner or user of the device does not have to activate the sleeve or sheath by pressing a button, twisting the device or taking any other action.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

One or more embodiments of the safety needle device of the present disclosure provide a safety needle device with a passive activation mechanism. In one or more embodiments, a device is provided that allows for at least one of shorter distance for lockout travel, ease of use, increased patient comfort, low part count, minimal part complexity, relatively compact design, and clear and unobstructed view of needle in an initial position.

Figure 1:
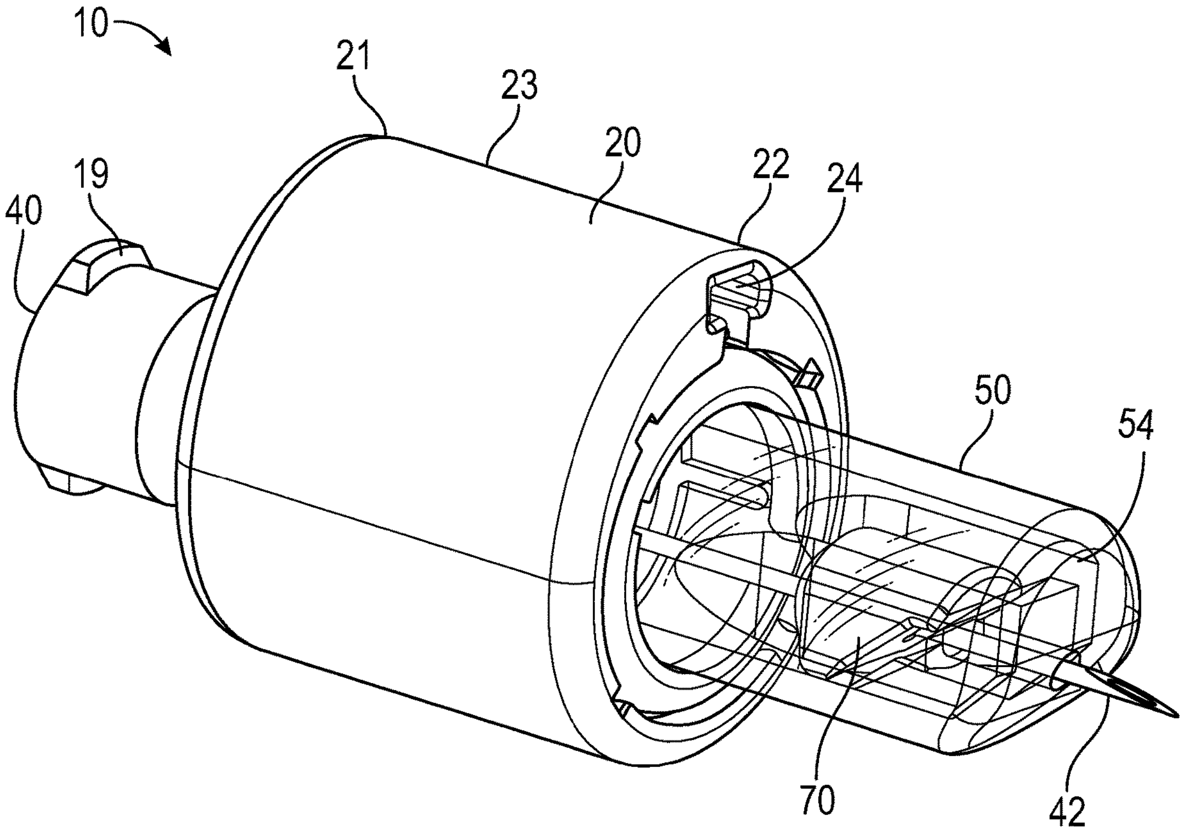
FIG. 1 illustrates a perspective view of a safety needle device according to a first embodiment.

FIG. 1 illustrates a safety needle device 10 that may be removably coupled to a standard or specially configured syringe (not shown). Although the illustrated safety needle device 10 is configured to be coupled to and removed from a syringe, the safety needle device 10 may instead be integrally formed with the syringe. The syringe is generally of a known type suitable for the withdrawal and injection and/or aspiration of fluids or other solutions by way of the safety needle device 10.

FIGS. 1-4 illustrate a first exemplary embodiment of a safety needle device 10 according to the present disclosure. As shown in FIG. 1, safety needle device 10 including a hub 40 configured to couple to a syringe (not shown), a needle cannula 42 having a proximal end 43 attached to the hub 40 and distal tip 44. The hub 40 may include lugs 19 to couple to a syringe, or other connection features may be included such as threads (not shown). The safety needle device 10 also includes a housing 20 having a proximal end 21, a distal end 22, a housing body 23 and an opening 24 located on the distal end. The hub is disposed on the proximal end of the housing, and the hub may be press fit, heat welded, glued, ultrasonically welded or attached to the housing by any other suitable way. The housing 20 may be of a unitary construction or may be formed from a plurality of components. In one or more embodiments, a proximal end 21 and a distal end 22 of the housing 20 can be separate components that are joined using techniques, such as but not limited to sonic welding, adhesive, snap or press fitting, or the like.

In one or more embodiments, the proximal end 21 of the housing 20 may be connectable to a luer connection or other fluid connector via hub 40, for example by lugs 19, or by threads or other suitable connection means. As shown in FIG. 1, needle cannula 42 is connected to hub 40 disposed at the proximal end 21 of the housing 20. In one or more embodiments, needle cannula 42 may have a sharp beveled tip at the distal tip 44, as shown in FIG. 1. Needle cannula 42 is disposed in the hub 40 in a manner as would be well understood in the art. Hub 40 may be integrally formed with the proximal end 21 of housing 20. Hub 40 may be configured to be removable or permanently attached to a syringe, or alternatively, hub 40 may be integrally formed with a syringe. For example, hub 40 may include internal or external threads or other suitable coupling, latching, or locking features such as tabs, slots, projections, pressure/snap fits, and the like, for removably coupling the safety device to a syringe. In some embodiments, the hub or housing may include a needle support 41 that extends axially from the hub 40 to support the needle cannula 42. Hub 40 is in fluid communication with the needle cannula 42 to permitting fluid to pass between a syringe and the needle cannula 42 when a syringe is connected to the hub 40.

The needle cannula 42 extends from the hub 40 disposed in the housing 20 and extends to a distal tip 44. As shown in FIG. 1, distal tip 44 of the needle cannula 42 is partially exposed and protruding from the distal end of the retractable sleeve 50 so as to be visible when the retractable sleeve 50 is in an initial position. The shaft of the needle cannula 42 is exposed from the retractable sleeve 50 when the retractable sleeve 50 is in a retracted position.

Needle cannula 42 in accordance with the present disclosure can be formed from conventional materials such as steel, more specifically stainless steel. It will be realized by the skilled artisan that medical grade plastics, composites, ceramics, or like materials can be utilized.

Figure 2:
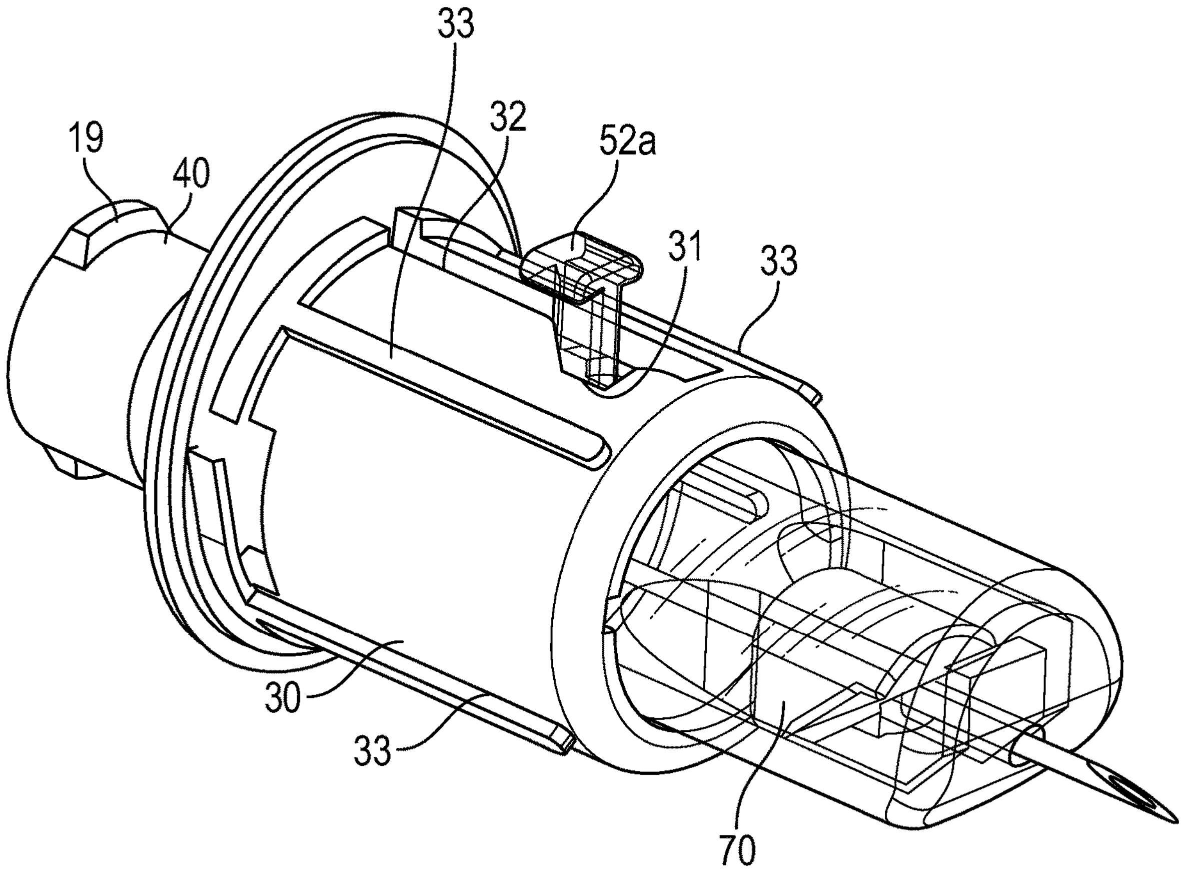
FIG. 2 illustrates a perspective view of a safety needle device shown in FIG. 1 in an initial state and without a housing.

In one more embodiments, incorporation of an activation component shown in the first embodiment as a tether 30 allows the overall size (length from the proximal end to the distal end) of the safety needle device to be significantly reduced. In one or more embodiments, as shown in FIG. 2, the tether 30 may be a telescoping tether having a first end or proximal end 30*a* connected with or attached to the housing body 23 and a second end or distal end 30*b* connected to or attached to retractable sleeve 50. In one or more embodiments, the tether 30 extends from the housing 20 as retractable sleeve 50 is moved distally along a length of the cannula.

Tether 30 is movably (e.g., slidably or rotationally or both slidably and rotationally) disposed in the housing 20. Tether 30 is generally parallel to a central axis which generally extends along the axis defined the needle cannula 42 extending within the housing body 23. In one or more embodiments, tether 30 has a slot with an enlarged first guide path 31 with a proximal angled lead ramped surface 35, a ledge 27 at the distal end of the enlarged first guide path for seating one or more radial protrusions 52*a* in the form of a bar extending from retractable sleeve 50, and a narrowed second guide path 32 extending distally from the enlarged first guide path 31. First guide path 31 is positioned at an angle, curvature or taper relative to the axis and intersects the second guide path 32. Second guide path 32 is in the form of a guide channel that is generally parallel to a central axis which extends along the housing body 23. In one or more embodiments, the angle, curvature or taper of the first guide path 31 permits the one or more radial protrusions 52*a* to shift between the first guide path 31 and second guide path 32 in the form of a guide channel. In one or more embodiments, the slot may include a transition region between the enlarged first guide path 31 and the narrowed second guide path 32, the transition region including an angled or ramped surface 35 to guide the one or more radial protrusions 52*a* extending from the sleeve into the narrowed second guide path 32 from the enlarged first guide path 31.

In one or more embodiments, the first guide path 31, and the second guide path 32 are disposed on the inner diameter of the tether 30 to prevent tampering or contact from a user. In other embodiments, the first guide path 31 and the second guide path 32 are exposed and visible to a user of the device.

The activation component in the form of the tether 30, having a proximal end 30*a* and a distal end 30*b*, may have the proximal end 30*a* connected to the housing 20 or hub 40 and the distal end 30*b* of the tether 30 may be connected to the retractable sleeve 50. In one or more embodiments, tether 30 may be in the form of a tube or concentric cone-shaped enclosures. In such embodiments, the tether 30 deploys from the housing around the needle cannula 42. Tether 30 extends from the housing as the retractable sleeve 50 is moved distally along the length of the cannula.

The term "retractable sleeve" is intended to include any type of member that can surround a needle cannula, such as a tubular member. The retractable sleeve 50 is dimensioned to be compatible with the size and type of needle cannula 40 as will be appreciated by those skilled in the art. The housing 20 includes a housing body 23 with an internal hollow region in which the retractable sleeve 50 may move axially in the proximal and distal direction. In one or more embodiments, the retractable sleeve does not rotate with respect to the housing or move radially with respect to the housing. Retractable sleeve 50 may be configured to move between an initial position, a retracted position and an extended position with respect to housing 20, wherein the initial position partially exposes a distal tip 44 of the needle cannula 42, the retracted position fully exposes the needle cannula 42, and the extended position fully covers the distal tip 44 of the needle cannula 42. The single-use passive safety device also includes a locking member 70 disposed in the retractable sleeve 50, the locking member being configured to cover the distal tip of the needle cannula when retractable sleeve is in the extended position. The single-use passive safety device also includes a spring element 90 to bias the retractable sleeve 50 from the retracted position to the extended position.

In one or more embodiments, retractable sleeve 50 is slidably disposed in the tether 30, the retractable sleeve having one or more radial protrusions 52*a* to slidably engage the slot of the tether. The distal end of the retractable sleeve includes an opening 55 in a distal wall thereof, through which distal tip 44 of needle cannula 42 moves through and is exposed.

As the retractable sleeve 50 moves distally along the needle cannula 42, the tether 30 extends along the length of the needle cannula 42.

Tether 30 and retractable sleeve 50 are designed to telescopically slide with respect to each other, but not to extend past each other, and the total extension length of the tether 30 is long enough to permit the retractable sleeve 50 to cover the length of needle cannula and for locking member 70 to extend over and cover the sharp distal tip 44 of the needle cannula 42. Tether 30 is configured to fully cover needle cannula 42 when the retractable sleeve is maximally extended to cover and shield the sharp distal tip 44 of the needle cannula.

Figure 3:
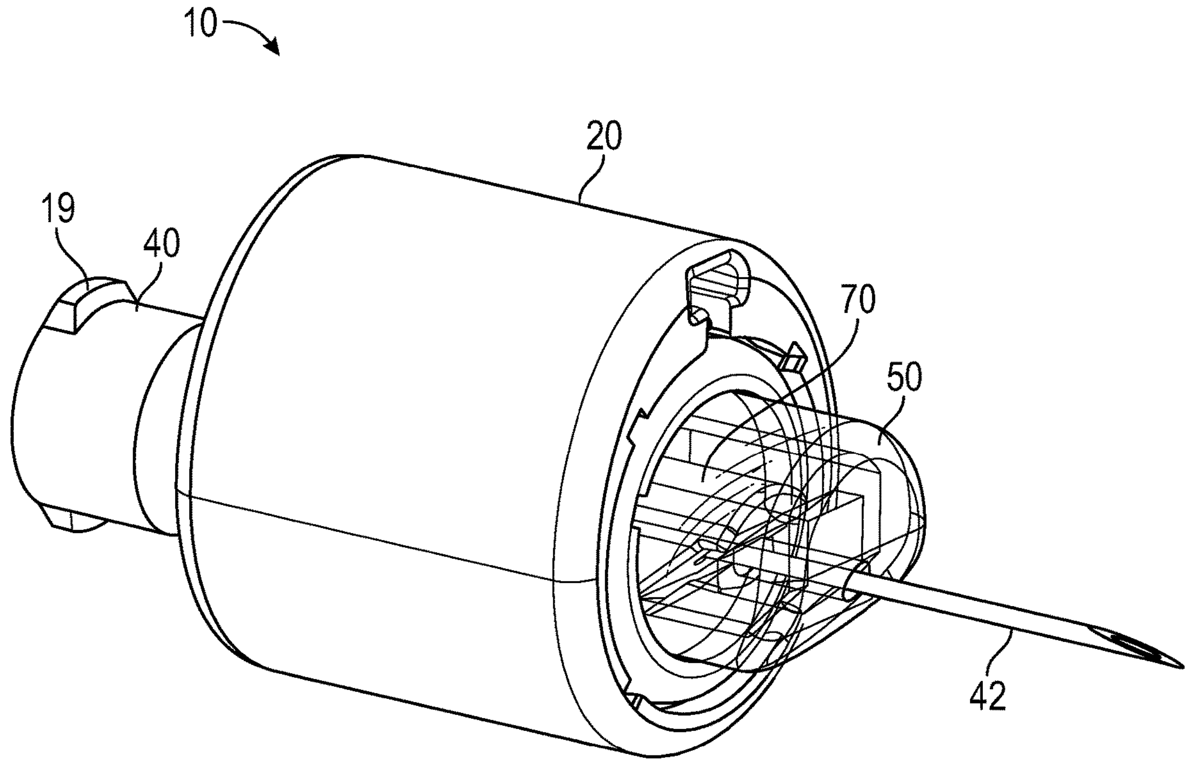
FIG. 3 illustrates a perspective view of a safety needle device shown in FIG. 1 in a retracted state.
Figure 4:
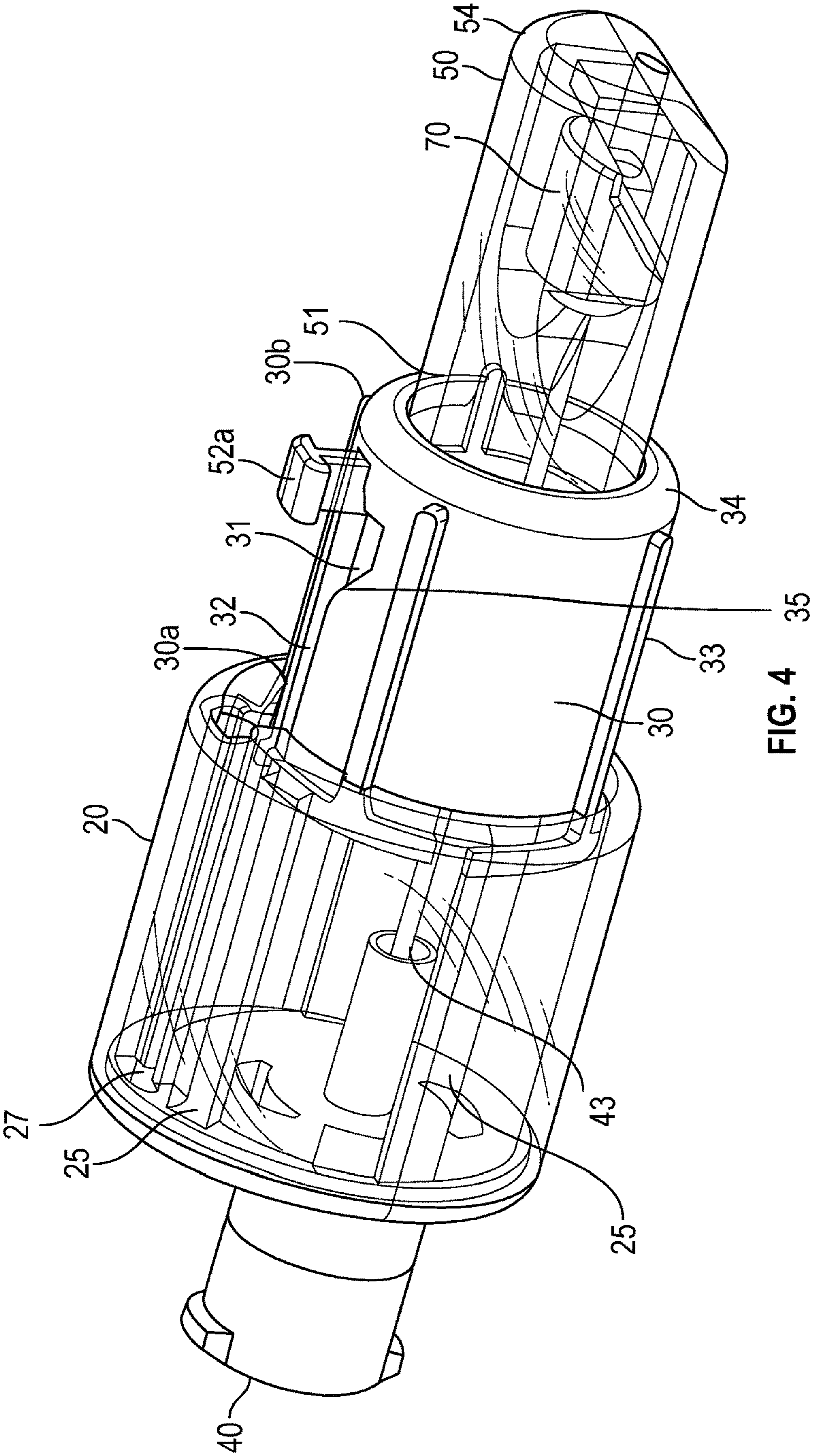
FIG. 4 illustrates a perspective view of a safety needle device shown in FIG. 1 in an extended state.

In one or more embodiments, as shown in FIGS. 1-4, the one or more radial protrusions 52*a* of retractable sleeve 50 comprise a protrusion radially extending from a proximal portion of the retractable sleeve 50. FIGS. 2 and 4 show a first embodiment having at least one protrusion 52*a* in the shape of a T-Bar (T-shaped protrusion) which keys with an opening 24 the retractable sleeve 50 to housing 20. In the embodiment shown, the opening 24 is complementary in shape to the protrusion 52*a*, and the opening 24 is a T-shaped opening. In an initial state, as shown in FIGS. 1 and 2, tether 30 holds retractable sleeve 50 in an initial position with the needle cannula distal tip 44 exposed. Upon movement of retractable sleeve 50, such as when the distal end 54 of the retractable sleeve is pushed against as subjects skin as the distal tip 44 of the needle cannula 42 is inserted into a subject, the radial protrusion 52*a* shown as a T-shaped protrusion 52*a* causes tether 30 to rotate until the one or more protrusion 52*a* shifts from a first guide path 31 along ramped surface 35 to a second guide path 32 and the tether 30 is no longer held within housing 20. As will be explained further below, ledges on the housing which supported a portion of ribs on the tether, the tether is released, and the tether and the sleeve are biased in a distal direction. As insertion of needle cannula 42 continues into a subject, the one or more protrusions 52*a* travels proximally along the second guide path 32 as the sleeve is pushed proximally away from the distal tip 44 of the needle cannula 42. Upon removal of the needle cannula 42 from a subject or patient, the radial protrusion 52*a* in the form of a T-shaped protrusion travels distally along the second guide path 32 of tether 30, and tether 30 fully extends out of the distal end of the housing 20 as the sleeve is biased in a distal direction. As shown in FIG. 1-4, in one or more embodiments, the locking member 70 is in the form of a sliding block to lock out the safety device. In this respect, the locking member may be a "blocking member," in that the locking member blocks the needle cannula 42 from moving (e.g., sliding) through the end of the sleeve, and thus locks the device from further use. The needle holds the device in the initial position until it exits centering holes on both the block and sleeve. Once the needle is out of both holes, the block is no longer constrained and the spring in the device pushes the block down the ramp misaligning the block and sleeve holes, thereby preventing the needle from exiting the device once again. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action. The sliding block is discussed in more detail below.

Figure 9:
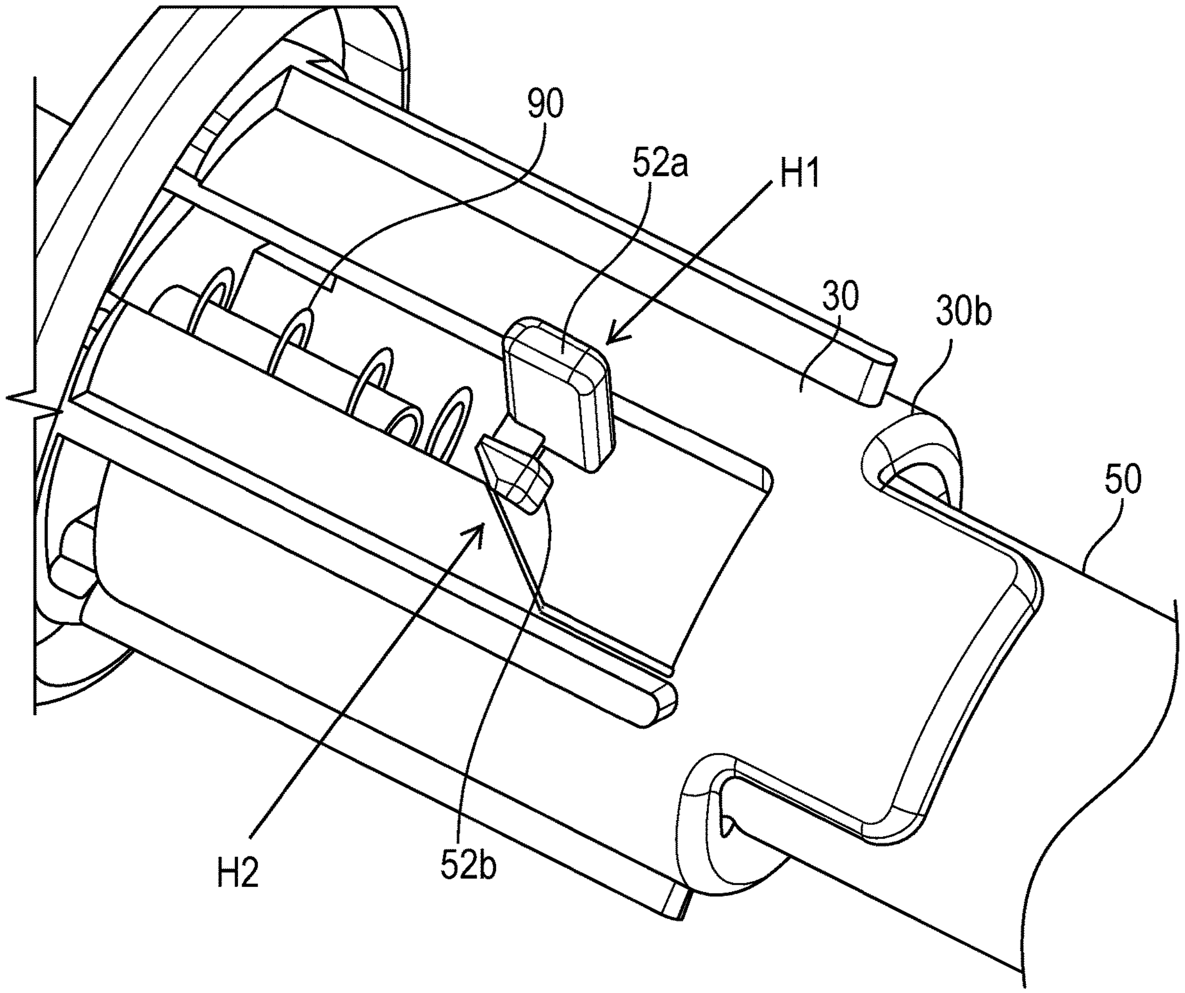
FIG. 9 illustrates a section view of a retractable sleeve keyed to a tether of a safety needle device according to an alternate embodiment having two protrusions.

In another embodiment, as shown in FIG. 9, the one or more radial protrusions 52*a* comprise a first radial protrusion 52*a* radially extending from a proximal portion of the retractable sleeve and having a height $H_1$ and a second radial protrusion 52*b* or tab radially extending from a distal portion of the retractable sleeve and having a height $H_2$, the height $H_1$ of the first protrusion extending radially from the sleeve being greater than the height $H_2$ of the second protrusion 52*b* extending from the sleeve. In yet another embodiment, the one or more protrusions comprise a single radially extending protrusion having a first portion having a first height and a second portion extending laterally from the first portion, the second portion having a second height that is less than the first height. In one or more embodiments, the second protrusion contacts the first guide path when the retractable sleeve is in the initial position and moves distally along the second guide path when the retractable sleeve is moved to the second position.

As shown in FIGS. 2-4, distal end 22 of housing 20 couples to tether 30 such that the tether 30 is configured to move along and at least partially rotate about a central axis. Distal end 34 of tether 30 couples to a proximal end of retractable sleeve 50. A channel and an opening 24 are included in the retractable sleeve 50 in order to permit the needle cannula 42 and distal tip 44 of needle cannula 42 to pass therethrough.

The proximal end of retractable sleeve 50 includes a one or more protrusions 52*a* configured to move between an initial position, a retracted position and an extended position with respect to the housing 20, wherein the initial position partially exposes a distal tip 44 of the needle cannula 42, the retracted position fully exposes the needle cannula 42, and the extended position fully covers the distal tip 44 of the needle cannula 42. The slot of the tether 30 includes a first guide path 31 and a second guide path 32 are disposed on the body of the tether and are configured to direct the retractable sleeve 50 during movement. In one or more embodiments, the first guide path, and second guide path are configured to slidingly receive the one or more protrusions of the retractable sleeve 50.

Retractable sleeve 50 is slidably mounted and movable in the distal opening 24 of the housing body to slidably accommodate and encase needle cannula 42 projecting axially from housing 20.

As illustrated in several of the drawings, most notably FIGS. 1 and 2, retractable sleeve 50 is generally comprised of a tubular portion and is slidably retractable along the length of the needle cannula 42 such that a distal tip 44 of the needle cannula 42 is partially exposed and protruding from the distal end of the retractable sleeve 50 when in an initial position so as to be visible to a user. A substantial or entire portion of needle cannula 42 is exposed when the retractable sleeve 50 is in its retracted position. The length of needle cannula 42 which extends from the hub 40 in a distal direction is completely encased when retractable sleeve 50 is in its extended position, as shown in FIG. 4.

The inside diameter of the retractable sleeve 50 is selected so that it will fit closely over needle cannula 42. The retractable sleeve 50 may be made of any suitable material, but preferably of a polymer which is tough enough to protect needle cannula 42.

In one or more embodiments, proximal movement of the retractable sleeve 50 from the initial position causes the one or more protrusions 52*a* of the retractable sleeve 50 to move from the enlarged first guide path 31 of the tether to the narrowed second guide path 32 of the tether. In one or more embodiments, the tether 30 rotates with respect to the housing 20 during proximal movement of the retractable sleeve from the initial position. Rotation of the tether 30 from the initial position to the second position guides the one or more protrusions 52*a* of the retractable sleeve from the enlarged first guide path 31 of the tether to the narrowed second guide path 32 of the tether.

In one or more embodiments, the enlarged first guide path 31 of the tether intersects the narrowed second guide path 32 of the tether. In one or more embodiments, the narrowed second guide path is generally parallel to a central axis and extends along the tether body. In one or more embodiments, the enlarged first guide path may comprise an angle, curvature or taper relative to a central axis. The angle, curvature or taper of the first guide path 31 may allow the one or more protrusions 52*a* to shift from the first guide path 31 to the second guide path 32.

The proximal end 51 of retractable sleeve 50 includes one or more protrusions 52*a* that extends radially outward from the proximal end of retractable sleeve 50 and is configured to engage one or more paths formed on the inside surface of the housing body 23. In one or more embodiments, one or more protrusions 52*a* may be an outwardly extending peg that seats against a ledge of the distal end of the housing in the initial position. As shown in FIG. 1, housing 20 has an opening 24 that receives the retractable sleeve 50 and its one or more protrusions 52.

In one or more embodiments, retractable sleeve 50 may be disposed and movable in the housing body 23. The retractable sleeve 50 is spring loaded, and is supplied to the user with the retractable sleeve 50 partially covering the needle cannula 42 so that the distal tip of the needle cannula is exposed and visible in an initial state, as shown in FIG. 1. In the initial state, the one or more protrusions 52*a* of the retractable sleeve 50 is disposed in the first guide path of the housing body. In one or more embodiments, the one or more protrusions is a peg. Upon administration of the injection, the retractable sleeve 50 moves from an initial position whereby the needle cannula is increasingly exposed so that the needle cannula may penetrate the injection site. As shown in FIGS. 2 and 4, the tether 30 rotates with respect to the housing 20 during proximal movement from the initial position.

During administration of an injection to a patient, the application of force by the user in the distal direction causes the one or more protrusions 52*a* of retractable sleeve 50 to move in a proximal direction such that one or more protrusions switches from the first guide path of the housing body to second guide path of the housing body. Proximal movement of the retractable sleeve 50 from the initial position transfers the one or more protrusions 52*a* of the retractable sleeve from the first guide path 31 on the slot of the tether to the second guide path 32 on the slot of the tether. In or more embodiments, the retractable sleeve moves from the initial position to the retracted position without impediment.

A continued application of force by the user in the distal direction causes rotational movement of tether 30 causing one or more protrusions 52*a* to move from the first guide path 31 of the tether to a narrowed second guide path 32.

The movement of the one or more protrusions from the enlarged first guide path inhibits or prevents counter-rotation of the tether 30, which in turn prevents the one or more protrusions 52*a* from shifting back into the enlarged first guide path 31 at intersection between the first guide path 31 and the second guide path 32. In one or more embodiments, a tether reverse prevention element prevents the tether from moving back to the first position after entering a second position. In one or more embodiments, the tether reverse prevention comprises one-way ratchet arms or a small detent bump. Detent bumps may allow for the device to be purposefully reset after sleeve depression to aid in manufacturability especially when needle lubing is required.

Upon continued application of force by pressing retractable sleeve 50 against the skin of a patient at the location where it is desired to insert needle cannula 42, retractable sleeve 50 retracts into housing 20 allowing the injection site to be penetrated by the needle cannula distal tip and needle cannula.

Upon completion of an injection to the patient, the user withdraws the needle cannula from the patient, thus causing the stored energy of spring element 90 to allow one or more protrusions 52*a* of the retractable sleeve 50 to proceed along the narrowed second guide path 32 to allow retractable sleeve 50 to fully cover needle cannula 42 in the extended position. The spring element 90 biases the retractable sleeve 50 in a distal direction to cover the distal tip 44 of needle cannula 42 causing activation of the locking member to prevent further translational movement of the retractable sleeve 50 within the housing body 23. Movement of the retractable sleeve from the retracted position to the extended position engages the locking member 70 to a distal tip 44 of the needle cannula 42 to block the needle cannula 42 from exiting the sleeve, providing a blocking function. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

In one or more embodiments, the locking member 70 is disposed on the retractable sleeve 50 and rides along the needle cannula 42 until the locking member 70 covers the distal tip 44 of the needle cannula 42 in the extended position. In one or more embodiments, the locking member 70 inhibits reuse of the safety needle device 10 by inhibiting further translational movement of the retractable sleeve 50 within the housing body 23. Needle cannula 42 is obscured from view when the retractable sleeve is in the extended position. As shown in FIG. 4, as the injection is completed and the distal tip 44 of needle cannula 42 is pulled from injection site, the stored force of spring element 90 causes the retractable sleeve 50 to extend, and at the end of the stroke, a second locking member extends over the distal tip 44 of the needle cannula 42 to lock the retractable sleeve 50 thereby completing a passive safety lock-out. In one or more embodiments, the locking member may comprise a clip, latch, a gate, or sliding block to shield the distal tip of the cannula. In one or more embodiments, the locking member may be metal. In one or more alternate embodiments, the locking member may be plastic.

In one or more embodiments, movement of the retractable sleeve from the retracted position to the extended position engages the locking member to a distal tip of the needle cannula.

In one or more embodiments, the locking member inhibits reuse of the passive safety needle device by inhibiting translation of the retractable sleeve.

In one or more embodiments, the locking member may comprise a metal clip, bead and spring plate, tumbling block, and a living hinge built into the sleeve. In one or more embodiments, the locking member may comprise one or more plastic cantilever arms disposed on the retractable sleeve, tether, or housing to lock the device.

Referring now to FIGS. 1 and 2, the safety needle device 10 is illustrated in an initial state wherein the retractable sleeve 50 is in a partially retracted configuration. Further retraction of the retractable sleeve 50 is generally initiated by a user applying pressure on the safety needle device 10 and/or syringe in the distal direction, which thereby encourages the retractable sleeve 50 proximally against the bias of the spring element 90. This retraction of the retractable sleeve 50 in turn further exposes the distal tip 44 of the needle cannula 42 and initiates penetration by the needle cannula 42 into the patient's skin. The one or more protrusions of the retractable sleeve, which is initially positioned in the enlarged first guide path 31, directs the retractable sleeve 50 to immediately move toward the narrowed second guide path 32. As the retractable sleeve 50 moves proximally, the one or more protrusions 52*a* passes through the narrowed second guide path 32 thereby encouraging the tether 30 to rotate about the axis. Upon reaching the intersection of the enlarged first guide path and the narrowed second guide path, rotation of the tether prevents the one or more protrusions 52*a* from returning to the enlarged first guide path.

Spring element 90 includes a proximal end, a main body, and a distal end. In one or more embodiments, as shown in FIG. 1, spring element 90 comprises a compression or coil spring. The spring element 90 biases the retractable sleeve from the retracted position to the extended position.

In one or more embodiment, spring element 90 engages and extends between the proximal end of the retractable sleeve and the proximal end of the housing. The spring biases the retractable sleeve 50 toward an initial position in which the one or more protrusions 52*a* of the retractable sleeve 50 is biased into engagement with the first guide path located at the distal end of the housing body 23 allowing the distal tip 44 of the needle cannula 42 to be exposed and visible in the initial position. The retractable sleeve 50 completely covers the distal tip 44 of the needle cannula 42 in the extended position. Many types of springs may be employed, such as but not limited to a helical coil spring, conical spring, wave-spring, or the like. In some embodiments, the spring element 90 is configured to facilitate retraction of the retractable sleeve 50 by a user applying distal pressure to the syringe and/or the safety needle device 10 with just one hand.

Safety needle device 10, and components thereof, can be formed using many manufacturing processes sufficient to provide the desired shape of the components. In some embodiments one or more components are made by a molding process, such as but not limited to injection molding, compression molding, blow molding, transfer molding, or similar. In some embodiments, one or more components are formed by forging, machining, casting, stamping, extrusion, a combination thereof, or the like.

In many embodiments, the safety needle device 10 is constructed from a biocompatible material. In some arrangements one or more of the components of the safety needle device 10 are plastic (e.g. polyurethane, etc.) or metal (e.g., stainless steel, etc.). In some embodiments, the housing 20 and/or the retractable sleeve 50 are constructed of materials that are either translucent or opaque.

In some embodiments, movement of the retractable sleeve 50 automatically engages the locking member 70. In some embodiments, movement of the retractable sleeve 50 from an about fully retracted position to an about fully extended position automatically prevents or inhibits reuse of the safety needle device 10.

Retractable sleeve 50 has one or more protrusions 52*a* are aligned with first guide path 31 of tether 30. The retractable sleeve 50 is slidingly moved through the distal opening 24 of housing 20. The needle cannula 42 is coupled with the needle support 41 of the housing 20. The spring element 90 is inserted into the housing body 23 and positioned to bias the retractable sleeve 50. Upon withdrawal of the needle cannula 42 from the patient, the stored spring energy of the spring element 90 to distally extend the retractable sleeve 50. As the retractable sleeve 50 distally extends, it covers the needle cannula 42 into the channel of the hub body thereby covering the distal end of the needle cannula 42. The distal movement of the retractable sleeve 50 also slides the one or more protrusions 52*a* along the second guide path.

As shown in FIG. 4, upon reaching the retractable sleeve 50 reaching the distal tip 44 of the needle cannula 42, the locking member 70 moves distally over the distal tip to cover the distal tip 44 of the needle cannula 42 to prevent reuse of the safety needle device 10. The retractable sleeve 50 has been fully extended and fully covers the needle cannula 42. The locking member 70 thus presents a physical stop to inhibit the retractable sleeve 50 from being proximally retracted again. In some embodiments the locking member engages the distal tip 44 of the needle cannula, meaning that the locking member 70 is in physical contact with the distal tip 44 of the needle cannula 42. In other embodiments, the locking member 70 blocks the opening 55 at the distal end of the sleeve 50. In such embodiments, the locking member 70 blocks the distal tip 44 of the needle cannula from exiting the opening 55 in the sleeve, thus functioning as a blocking member that locks out a user from further utilizing the device 10.

Therefore, embodiments of the present disclosure utilize one or more protrusions 52*a* on the retractable sleeve traveling along a first guide path 31 and second guide path 32 disposed on tether 30. Once injection begins, the one or more protrusions 52*a* on the retractable sleeve 50 travels along the a first guide path 31 and second guide path 32 rotating the tether from an initial position to a second position as it moves axially. At this point, the user can continue to insert the needle to the desired depth in the patient and the tether 30 will move axially within the second guide path 32 of the tether. Upon removal of the needle cannula, spring element 90 within the system will push the retractable sleeve 50 down the second guide path 32 to a final position and the locking member 70 will automatically cover the distal tip 44 of the needle cannula 42 thereby passively protecting the user from needle stick injury.

In one or more embodiments, the tether includes one or more ribs 33 that interact with one or more guide tracks disposed on the inner surface of the housing body. The one or more ribs 33 on tether 30 interact with one or more guide tracks 25 within the housing 20 to capture the tether 30 within the housing 20 in the initial position. Each rib 33 slidably engages each guide track 25, and upon activation, the each of one or more ribs 33 slidably moves along each ledge 27 within the housing 20 to one or more openings such that the one or more ribs 33 no longer constrain the tether 30 to the housing 20. Once rotation of tether 30 is completed, the one or more ribs disposed on the top surface of the tether 30 snap into the one or more guide tracks disposed on the inner surface of the housing body. The one or more ribs 33 serve to keep tether 30 from rotating back to the initial position ensuring that final lockout with locking member 70 will occur. At this point, the user can continue to insert the needle to the desired depth in the patient and the retractable sleeve 50 will move axially within the narrowed second guide path. Thereafter, upon removal of the device, the tether and its associated ribs can extend out of the housing allowing the needle cannula distal tip to be shielded. Contemporaneously, upon removal of the needle cannula, spring element 90 within the system will push the retractable sleeve 50 down the narrowed second guide path to a final position and the locking member 70 will automatically cover the distal tip 44 of the needle cannula 42 thereby passively protecting the user from needle stick injury.

In one or more embodiments, in the initial state, the one or more protrusions of the retractable sleeve interact with the slot of the tether, tether holds the device in such that the distal tip of the needle cannula is exposed and the retractable sleeve and tether are keyed to the housing such that it can only move in and out of the device. In one or more embodiments, one or more ribs of the tether interact with the guide tracks of the housing body to hold the device in an initial state such that the distal tip of the needle cannula is exposed and the retractable sleeve and tether are keyed to the housing such that it can only move in and out of the device. In this state, the tether is constrained along the length of the part so that it cannot extend out of the housing. Upon insertion of the device into a patient, vial, or other medium, the activation feature on the sleeve of the device causes the tether to move from an initial position to a second position. In one or more embodiments, this motion can be rotational or linear. In the second position, the tether is no longer contained within the housing and is allowed to extend out of the housing once the device is removed from the patient, vial, or other medium. As the tether extends out of the housing, the retractable sleeve also disengages from the housing and the tip of the needle is shielded.

Figure 5:
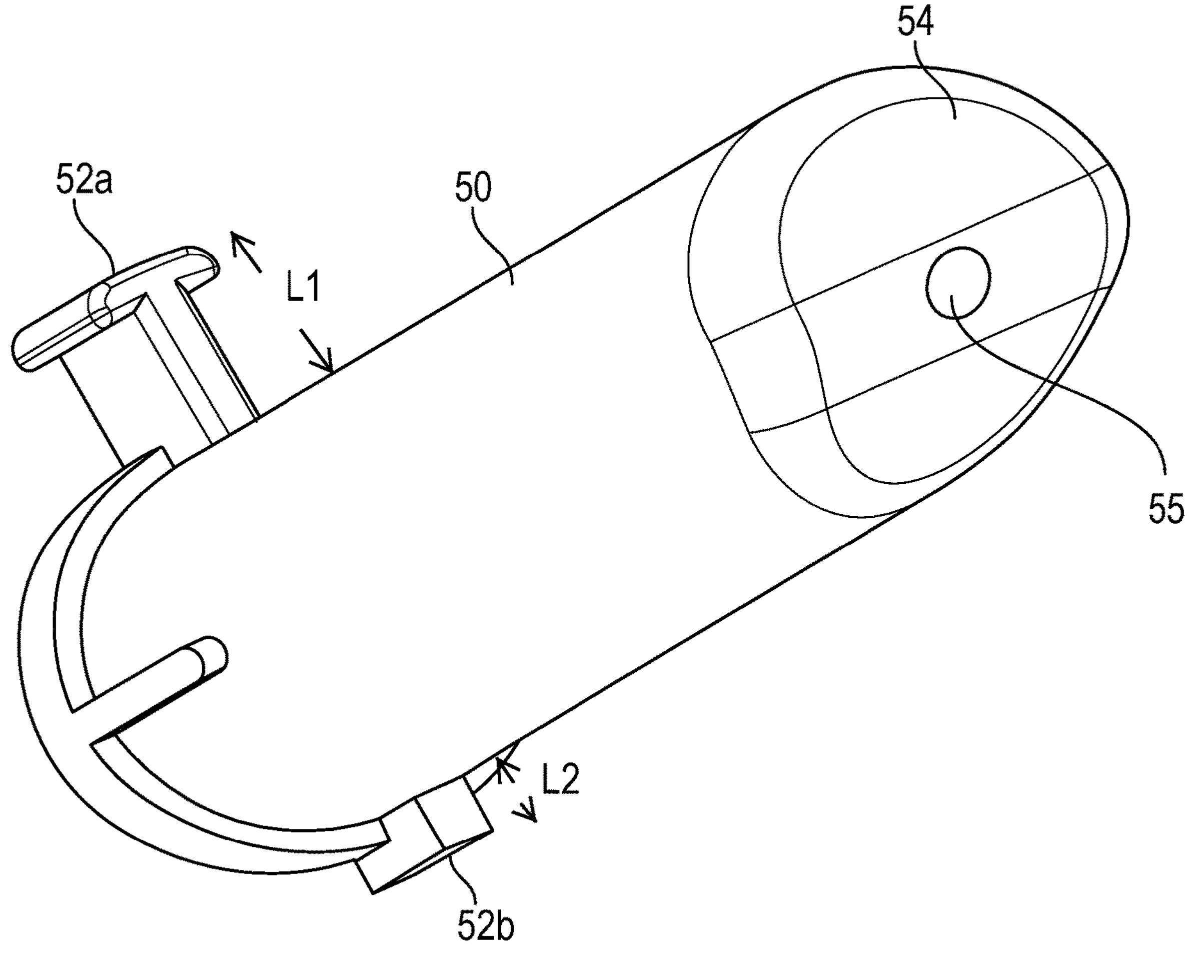
FIG. 5 illustrates a perspective view of a retractable sleeve of a safety needle device according to a first embodiment.
Figure 6:
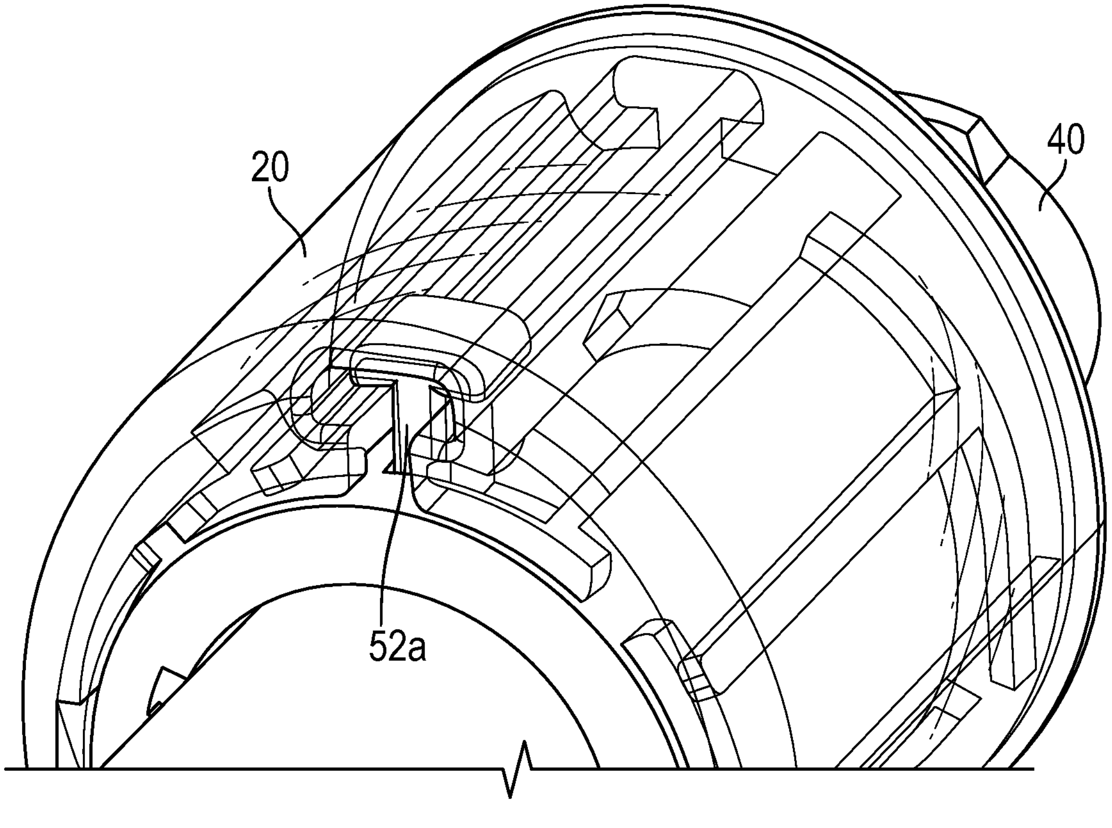
FIG. 6 illustrates a section view of a retractable sleeve keyed to a housing of a safety needle device according to a first embodiment.
Figure 7:
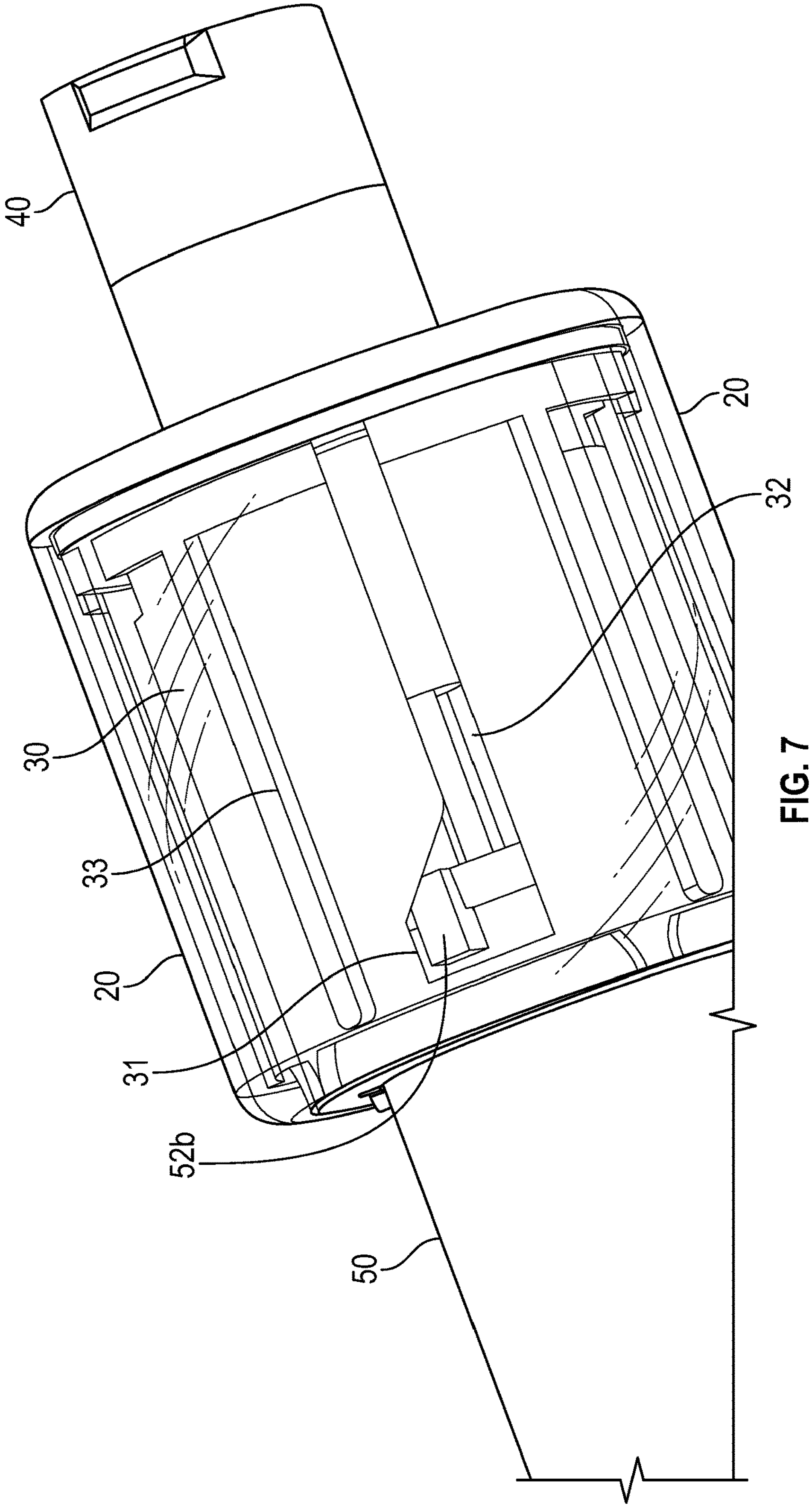
FIG. 7 illustrates a section view of a retractable sleeve keyed to a tether of a safety needle device according to a first embodiment.

As shown in FIG. 5, in one or more embodiments, the one or more protrusions may comprise a first protrusion 52*a* of a first length L1 and a second protrusion 52*b* having a second length L2 less than L1. In another embodiment (not shown), the first protrusion 52*a* may be located 90° to the second protrusion 52*b*. In yet another embodiment, as shown in FIG. 5, the first protrusion 52*a* may be located 180° to the second protrusion 52*b*. In one or more embodiments, as shown in FIG. 5, the first protrusion 52*a* is T-shaped and the second protrusion 52*b* is in the form of a peg or tab. FIG. 6 shows the embodiment of FIG. 5 in which the first protrusion 52*a* keys to housing 20 but has no impact on rotating tether 30 to activate the safety needle device 10. FIG. 7 shows the embodiment of FIG. 5, in which the second protrusion 52*b* engages with the tether 30 and activates the device by causing the tether 30 to rotate. In such an embodiment, the second protrusion 52*b* does not engage with housing 20.

Figure 8:
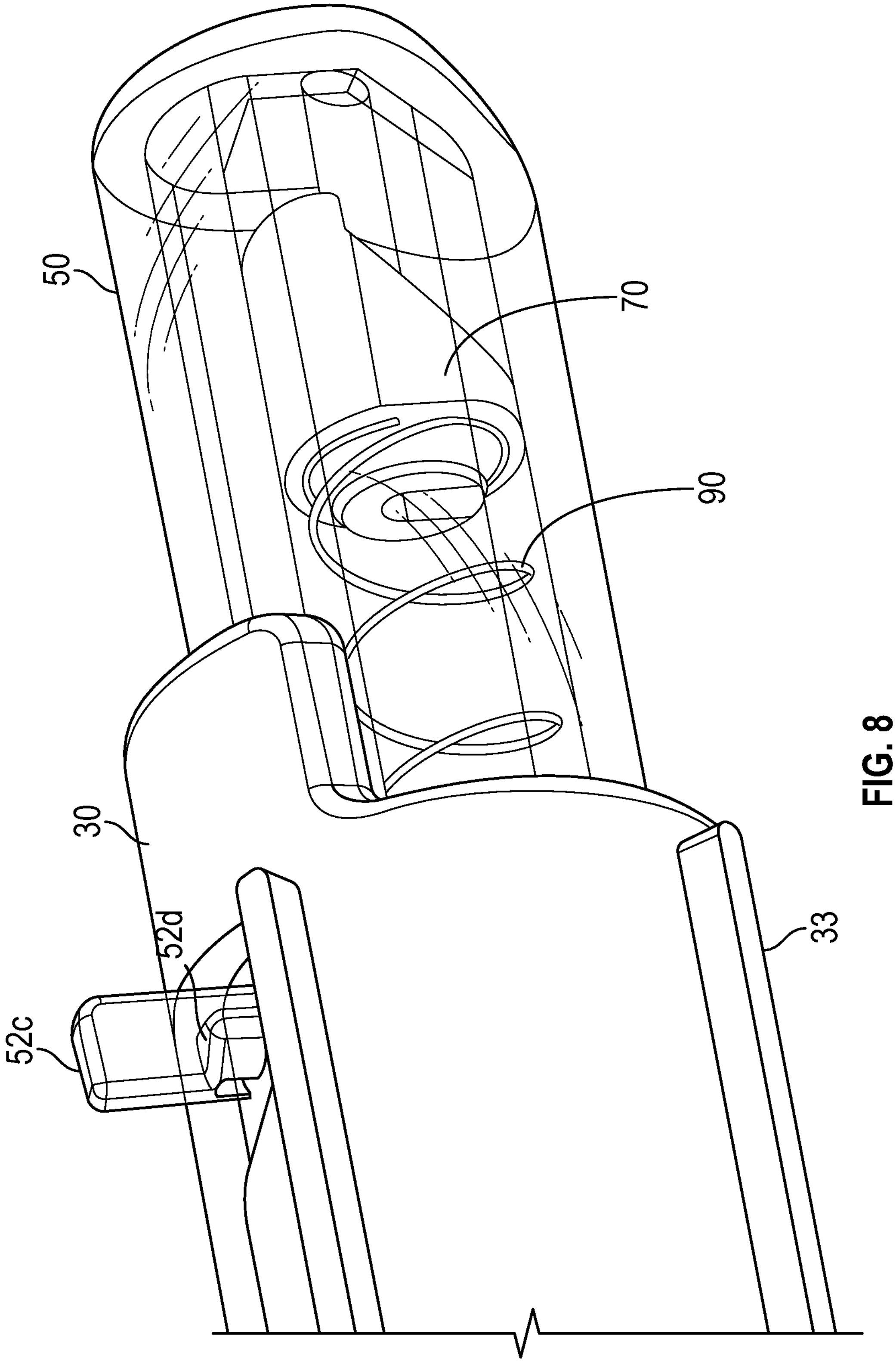
FIG. 8 illustrates a section view of a retractable sleeve keyed to a tether of a safety needle device according to an alternate embodiment having two protrusions.

FIG. 8 shows an alternate embodiment of the retractable sleeve 50 having one or more protrusions in which the first and second protrusions are integral, the first protrusion 52*c* of the integral protrusions is in the shape of an elongate bar and the second protrusion 52*d* of the integral protrusions is an activation bump or a shorter protrusion having a height that is less than the first protrusion 52*c* of the integral protrusions. First protrusion 52*c* interacts with a slot in the housing 20 to rotationally key the housing and the retractable sleeve. The second protrusion 52*d* is connected to or integral with the first protrusion and engages with tether 30 and activates the safety needle device 10 by causing the tether to rotate. The second protrusion 52*d* does not engage with the housing.

Figure 10:
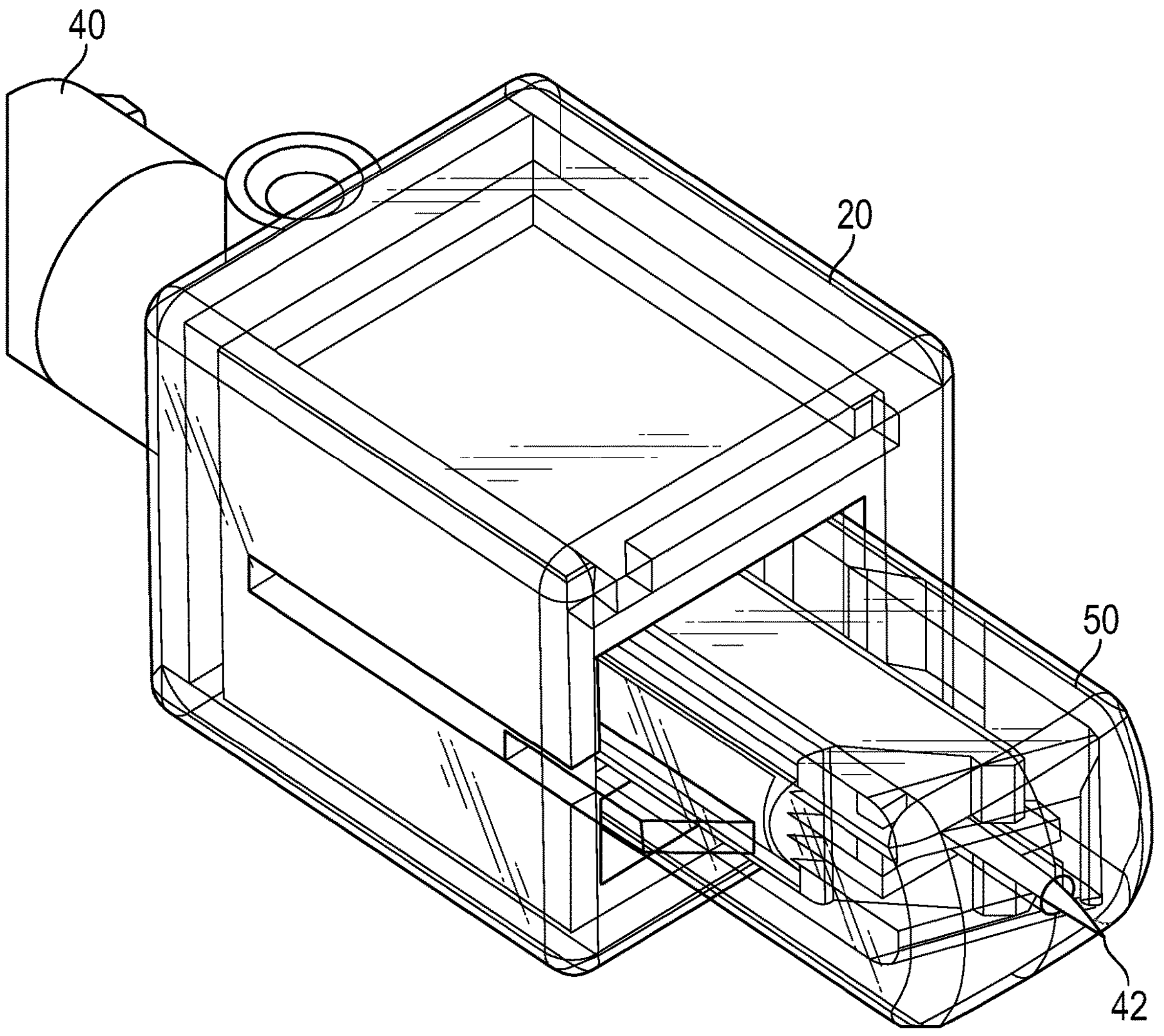
FIGS. 10 and 11 illustrate a perspective view of a retractable sleeve of a safety needle device according to an alternate embodiment utilizing linear motion.
Figure 11:
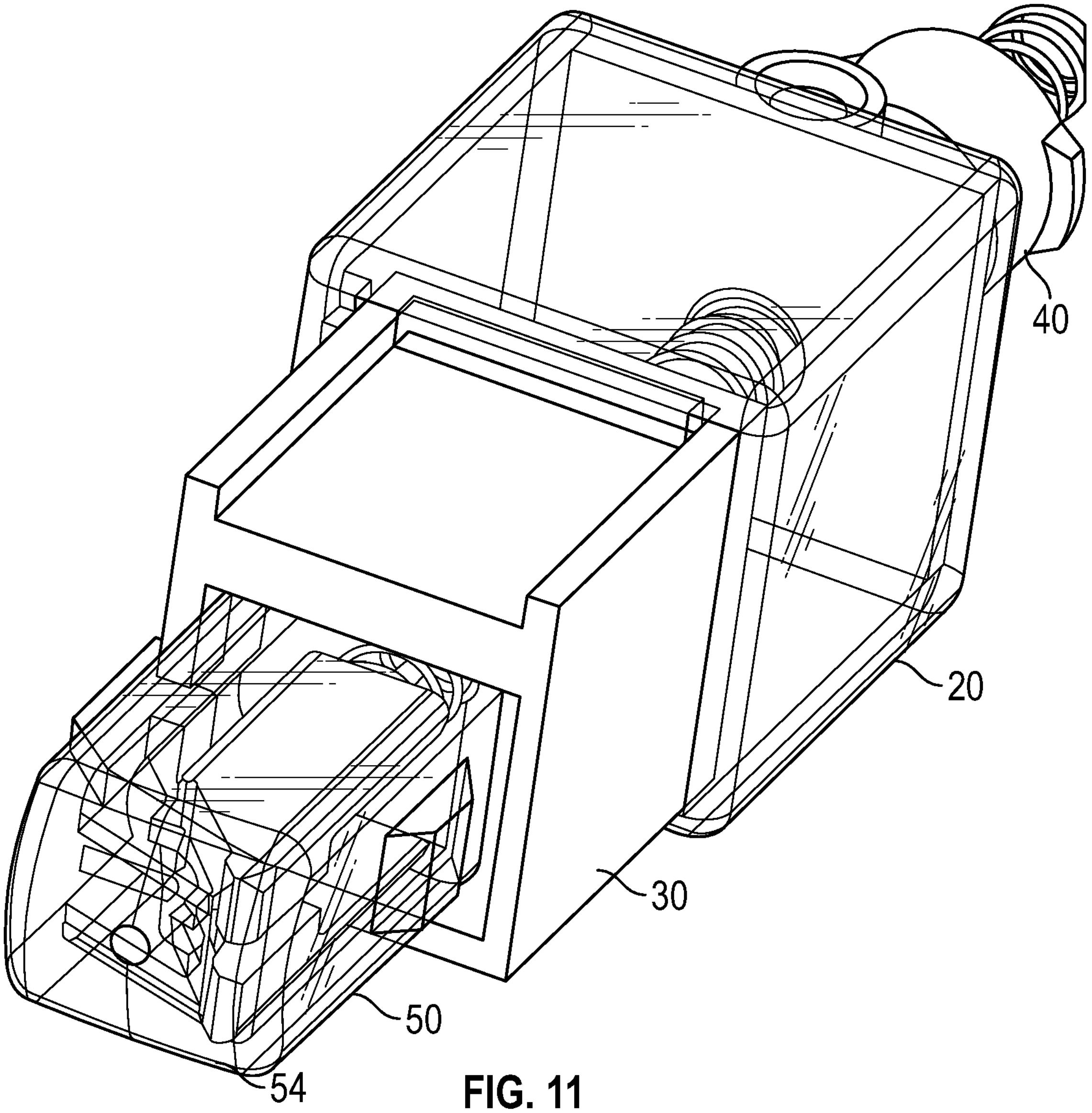

FIG. 9 shows an alternate embodiment of the retractable sleeve having one or more protrusions in which the first protrusion 52*a* interacts with a slot in the housing to rotationally key the housing and the retractable sleeve. In one or more embodiments, as shown in FIG. 9, the first protrusion 52*a* may be adjacent to but separated from the second protrusion 52*b*. In one or more embodiments, the second protrusion 52*b*, in the form of a peg, small tab or bump, engages with tether 30 and activates the safety needle device 10 by causing tether 30 to rotate. The second protrusion 52*b* does not engage with the housing 20. The FIGS. 10 and 11 show an alternate embodiment in which tether 30 utilizes linear motion instead of rotational motion. As shown in FIG. 10, retractable sleeve and tether start in an initial position with the distal tip 44 of the needle cannula exposed and tether 30 retained in housing 20. Upon movement of the retractable sleeve 50 in a proximal direction, one or more bevels on the retractable sleeve 50 interact with tether 30 to move the tether from a starting position to a second position where it is no longer locked to the housing 20. After completion of the injection and upon removal the safety needle device 10 from the patient, retractable sleeve 50 and tether 30 are allowed to fully extend as they are no longer locked to housing 20. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action. As shown in FIGS. 10 and 11, the locking element may be in the form of a sliding block to lock out the safety device to prevent re-use and accidental needle stick injury. It is also contemplated that the locking element may be in the form of a metal clip, latch or gate.

As shown in FIGS. 12-19, in one or more embodiments, the proximal end 51 of retractable sleeve 50 includes a retention hook 53 that extends radially outward from the proximal end of retractable sleeve 50 and is configured to engage the activation latch 80 of the housing body 23.

Figure 12:
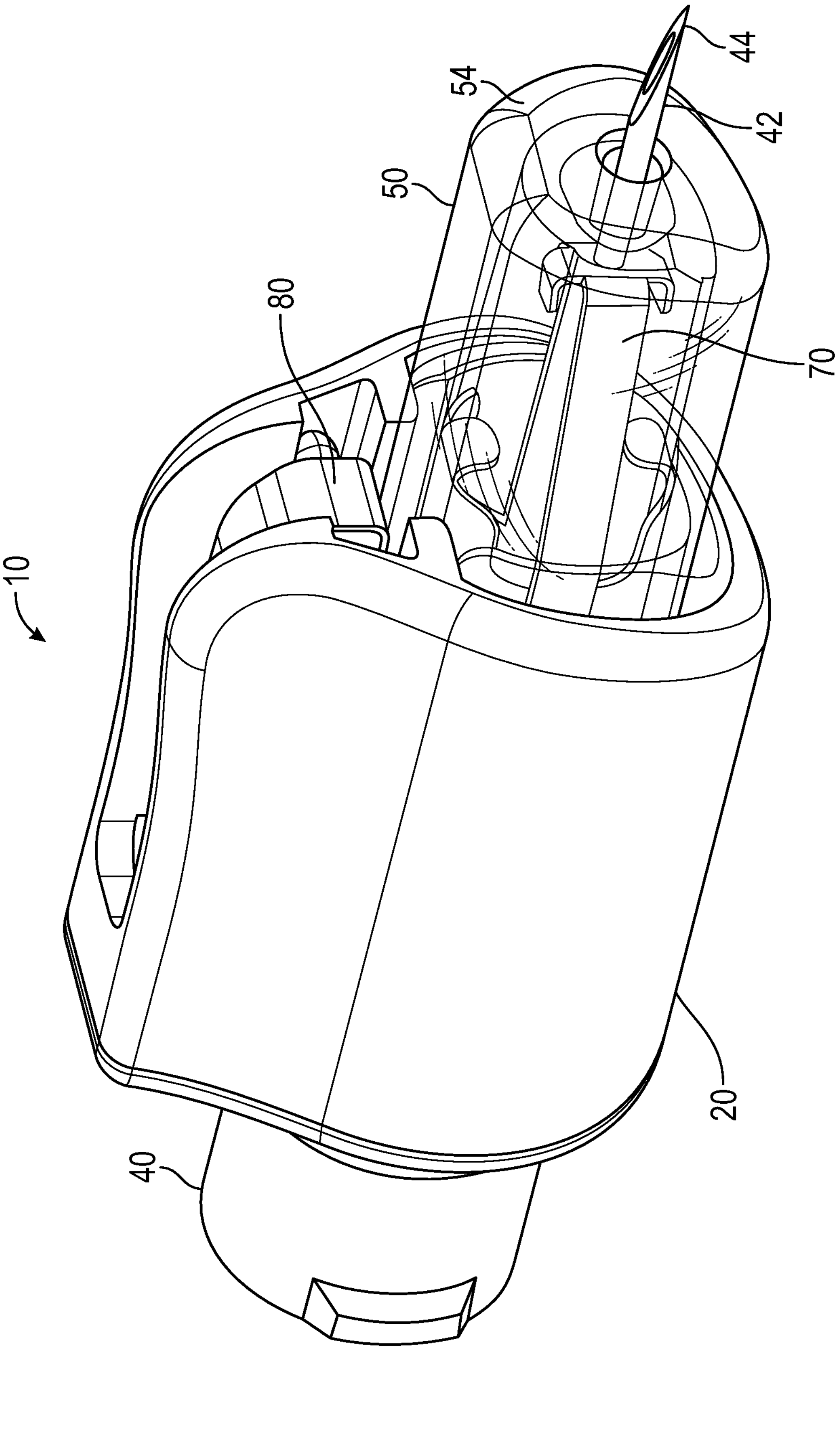
FIG. 12 illustrates a perspective view of a safety needle device according to an alternate embodiment including a retention hook.
Figure 13:
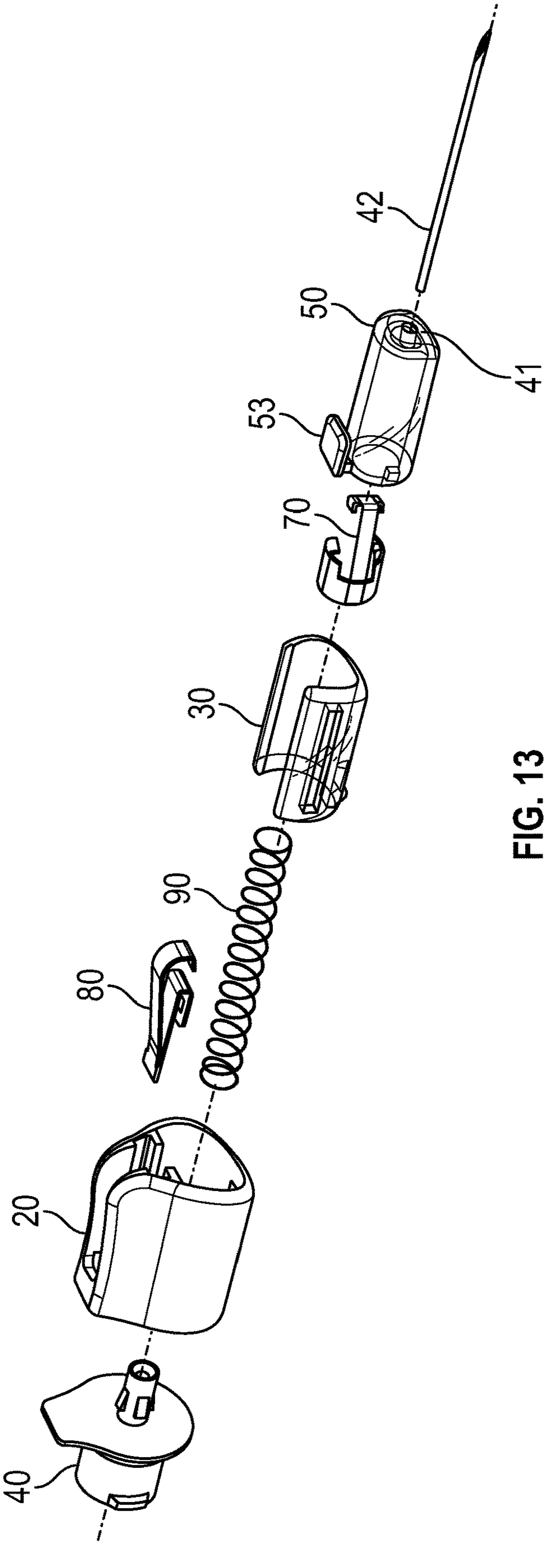
FIG. 13 illustrates an exploded view of a safety needle device of FIG. 12.

FIG. 12 illustrates a perspective view of a safety needle device according to an alternate embodiment including a retention hook 53 and FIG. 13 illustrates an exploded view of a safety needle device of FIG. 12.

As shown in FIG. 12, housing 20 has an opening 24 that receives the retractable sleeve 50. In one or more embodiments, retractable sleeve 50 may be disposed and movable in the housing body 23. The retractable sleeve 50 is spring loaded, and is supplied to the practitioner with the retracting sleeve 50 partially covering the needle cannula 42 so that the distal tip of the needle cannula is exposed and visible in an initial state. Upon administration of the injection, the retractable sleeve 50 moves from an initial position whereby the needle cannula is increasingly exposed so that the needle cannula may penetrate the injection site.

As shown in FIGS. 12 and 13, one or more embodiments of the safety needle device 10 include an activation latch 80 in combination with a spring element 90. In the initial state both the activation latch 80 and the spring element 90 hold stored energy. Upon beginning injection, the energy in the activation latch 80 is released once the retention hook 53 on the proximal end of the retractable sleeve 50 is released from engagement with the activation latch 80 upon a practitioner depressing the activation latch over a very short distance.

Once the activation latch 80 is released from the retention hook 53 on the proximal end of the retractable sleeve 50, the practitioner can continue to inject the cannula to their desired depth in a patient during an injection (or a vial during a syringe filling procedure) by either utilizing the full length of the needle or a significantly shorter distance of the needle cannula. Upon removing the needle cannula 42 from a patient, the retractable sleeve 50 is biased by the spring element 90 to automatically advance forward as the stored energy in the spring element 90 is released allowing retractable sleeve 50 to continue to be pushed forward until the a locking member 70 in the form of a lockout latch is able to clip over the distal tip 44 of the needle cannula 42 thereby passively locking out the safety needle device 10 and preventing needle stick injury to the practitioner. In one or more embodiment, activation latch 80 may be a metal latch. In one or more embodiments, the locking member 70 in the form of a lockout latch may be a metal latch that has a bend that engages the distal tip 44 of the needle cannula 42.

During administration of an injection to a patient, the application of force on the needle device by the practitioner in the distal direction and/or depression of the activation latch 80 by the practitioner causes the retractable sleeve 50 to move in a proximal direction. In or more embodiments, the retractable sleeve moves from the initial position to the retracted position without impediment. A continued application of force by the practitioner in the distal direction causes activation latch 80 to disengage from the retention hook 53 thus activating the locking member 70 in the form of a lockout latch. In one or more embodiments, the locking member 70 in the form of the lockout latch includes a metal latch on a distal end of the retractable sleeve. Proximal movement of the retractable sleeve from the initial position disengages the activation latch 80 from the retention hook 53. In some embodiments, the activation latch 80 is generally resilient, so that the radially inwardly disposed second ends can flex and then return to the original position even after the ends have been radially outwardly deflected. In one or more embodiments, the activation latch 80 may include a latching member, such as a hook, clasp, detent, ratchet, or other structure.

Upon completion of an injection to the patient, the practitioner withdraws the needle cannula from the patient, thus causing the stored energy of spring element 90 to allow the retractable sleeve 50 to proceed to fully covers needle cannula 42 in the extended position. The spring element 90 biases the retractable sleeve 50 in a distal direction to cover the distal tip 44 of needle cannula 42 causing activation of the locking member 70 in the form of a lockout latch to prevent further translational movement of the retractable sleeve 50 within the housing body 23. Movement of the retractable sleeve from the retracted position to the extended position engages the locking member in the form of the lockout latch to a distal tip of the needle cannula. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

In one or more embodiments, the locking member 70 in the form of the lockout latch is disposed on the retractable sleeve and rides along the needle cannula until the lockout latch covers the distal tip 44 of the needle cannula 42 in the extended position. In one or more embodiments, the retractable sleeve 50 extends in length beyond the lockout latch. In one or more embodiments, lockout latch comprises a protective clip which can have a V-shape at the distal end to cover the distal tip 44 of the needle cannula 42 in the extended position. In one or more embodiments, the lockout latch inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position. As the injection is completed and the distal tip 44 of needle cannula 42 is pulled from injection site, the stored force of spring element 90 causes the retracting sleeve 50 to extend, and at the end of the stroke, a lockout latch extends over the distal tip of the needle cannula 42 to lock the retractable sleeve 50 thereby completing a passive safety lock-out. In one embodiment, the lockout latch is a metal clip.

Figure 14:
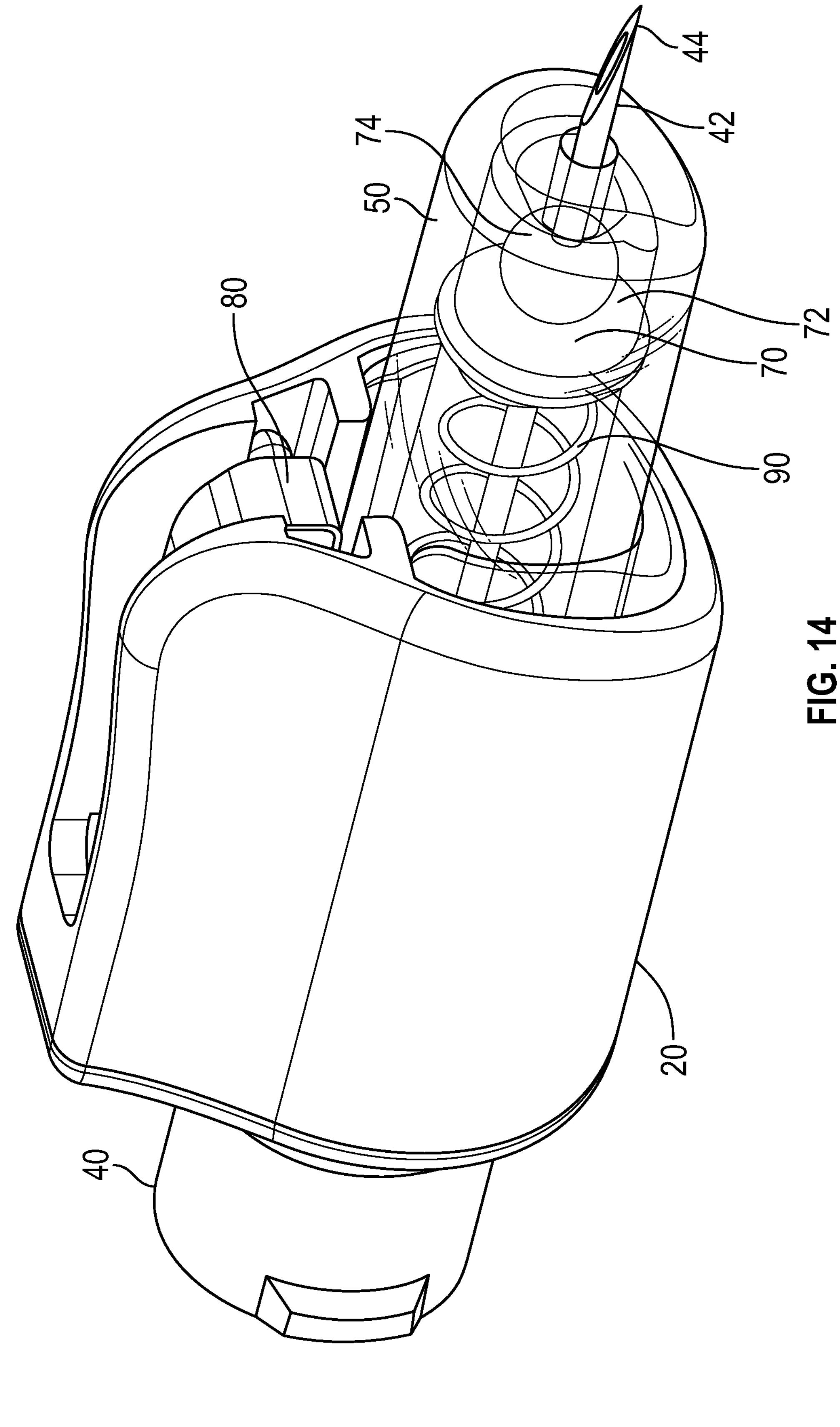
FIG. 14 illustrates a perspective view of a safety needle device according to an alternate embodiment having a locking element with a bead and spring plate.
Figure 15:
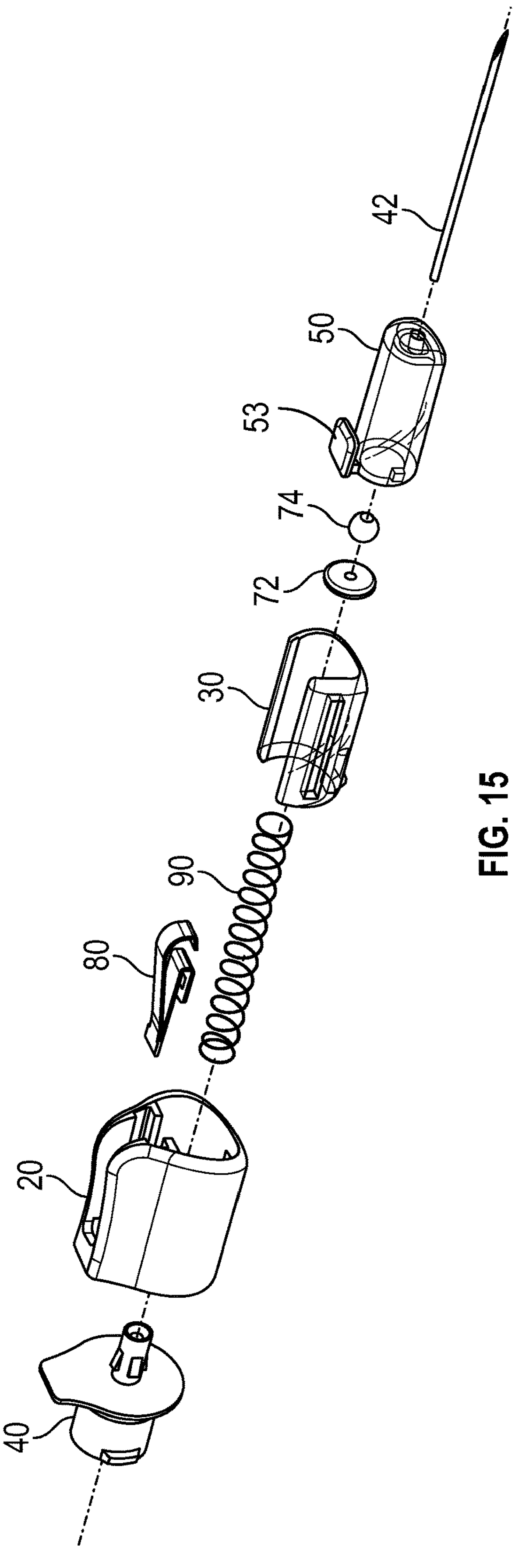
FIG. 15 illustrates an exploded view of a safety needle device of FIG. 14.

FIG. 14 shows an alternate embodiment having a locking member including a bead and spring plate. FIG. 15 shows an exploded view of the embodiment shown in FIG. 14. As shown in FIGS. 14 and 15, locking member 70 may be in the form of a spring plate 72 and bead 74 in combination with a spring element 90 to pivot that bead 74 and spring plate 72 in order to achieve lockout and thereby preventing the needle from re-finding the hole. In one or more embodiment, spring plate 72 and bead 74 are housed inside the retractable sleeve 50 as shown in FIGS. 14-15. Retractable sleeve 50 utilizes the energy in spring element 90 to bias the retractable sleeve upon lockout so that the needle and corresponding holes in the spring plate 72 and bead 74 are no longer co-axial preventing the needle from once again finding the hole.

In one or more embodiments, as shown in FIGS. 14 and 15, spring plate 72 and bead 74, respectively, have a channel within the body of spring plate 72 and bead 74. In an initial state, the cannula is threaded through the channel of both the spring plate 72 and bead 74 allowing the distal tip of the cannula to protrude from the distal end of the retractable sleeve 50 such that distal tip of the cannula is visible to the practitioner. Upon administration of an injection to a patient, the retractable sleeve 50 moves in a proximal direction such that the needle cannula moves out of the channel of both spring plate 72 and bead 74 allowing both spring plate 72 and bead 74 to rotate such that the distal tip 44 of needle cannula 42 is prevented from re-entering the channel within the body of the spring plate 72 and bead 74 to prevent exposure of the practitioner from the distal tip 44 of needle cannula 42.

If the distal tip of the cannula attempts to pass back through the channel of spring plate 72 and bead 74, the distal tip will be buttressed by the body of one or both of the spring plate 72 and bead 74 thus causing the distal tip to remain safely disposed within the housing 20.

Spring plate 72 and bead 74 may be made of strong material to prevent the distal tip 44 of the needle cannula 42 from piercing through the spring plate and bead.

Figure 16:
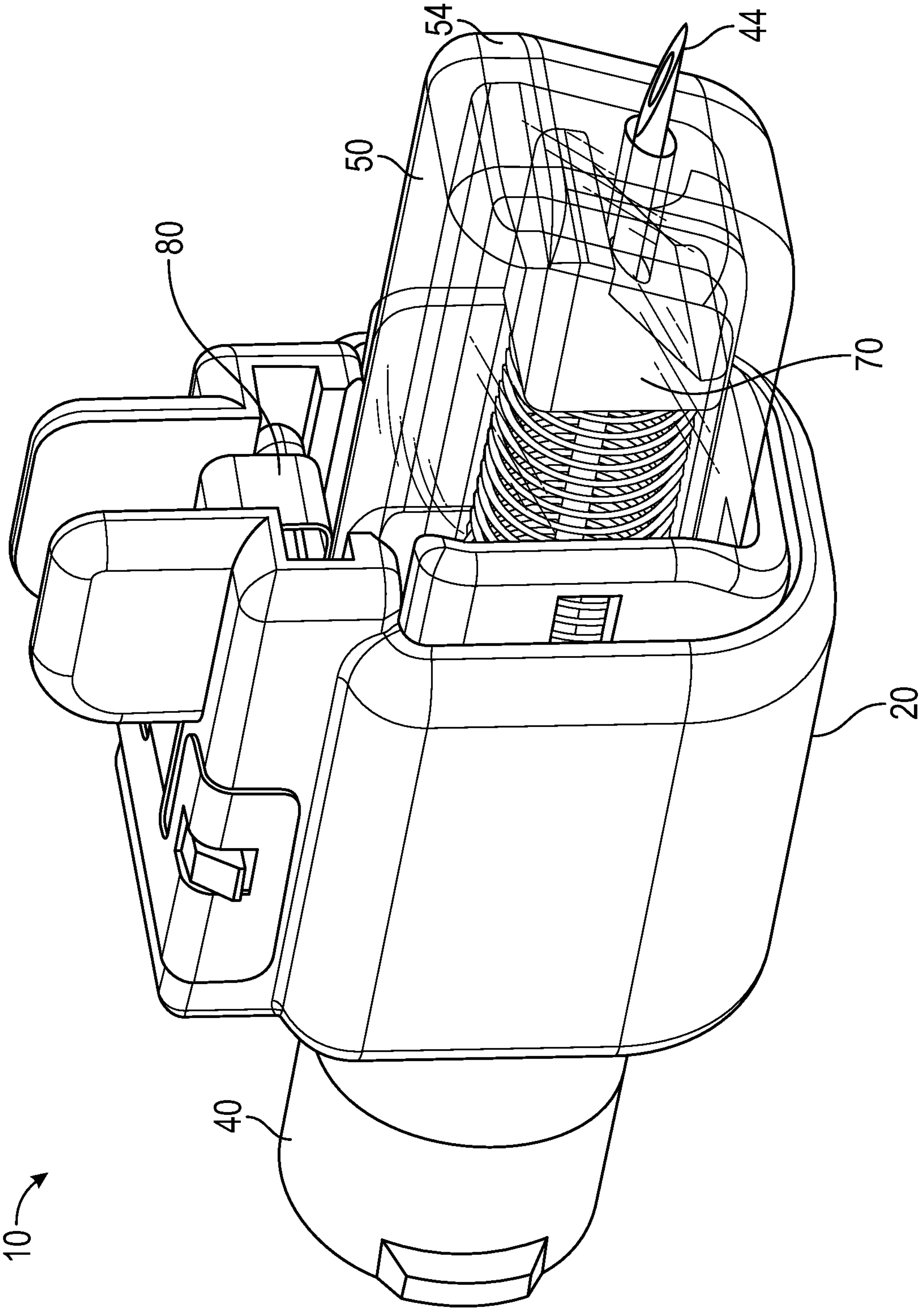
FIG. 16 illustrates a perspective view of a safety needle device according to an alternate embodiment having a locking element in the form of a sliding block.
Figure 17:
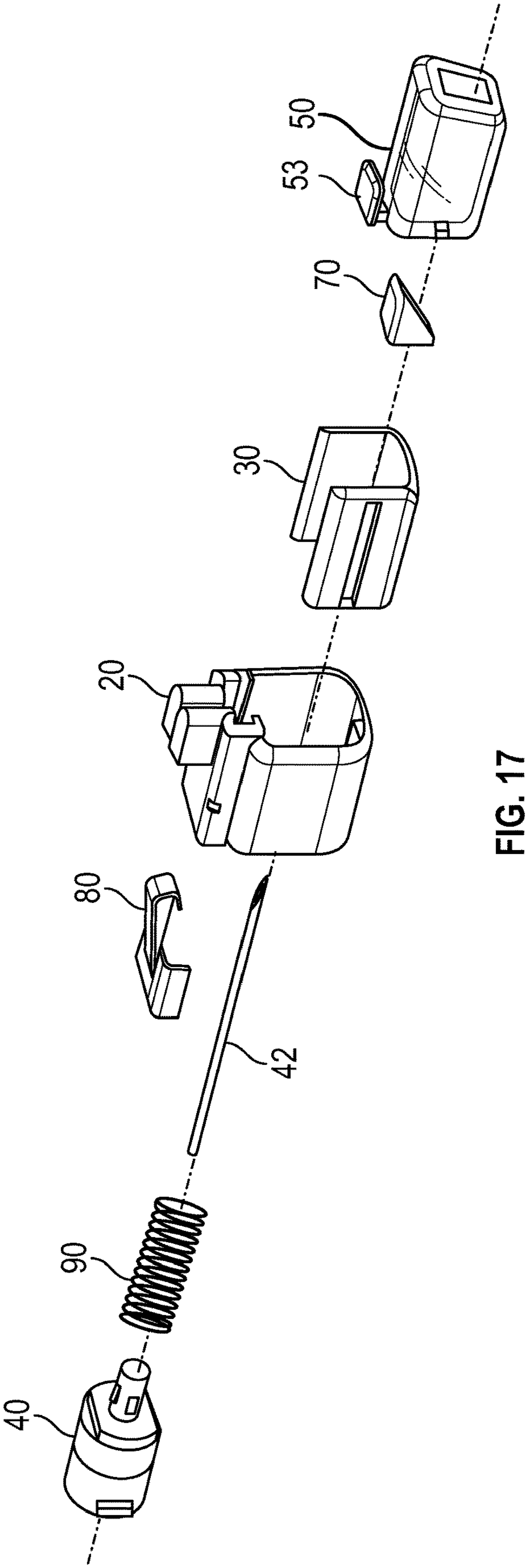
FIG. 17 illustrates an exploded view of a safety needle device of FIG. 16.

FIGS. 16-18 show an alternate embodiment in which locking member 70 is in the form of a sliding block. FIG. 17 shows an exploded view of embodiment shown in FIG. 16. As shown in FIGS. 16-18, locking member 70 may be in the form of a sliding block in combination with a spring element to pivot that sliding block in order to achieve lockout and thereby preventing the needle from re-finding the hole. In one or more embodiment, sliding block is housed inside the retractable sleeve 50 as shown in FIGS. 16-18. As shown in FIG. 18, retractable sleeve 50 utilizes the energy in spring element 90 to bias the retractable sleeve upon lockout so that the needle and the hole are no longer co-axial preventing it from once again finding the hole. In one or more embodiments, sliding block may be configured as an angled plastic component.

Figure 18D:
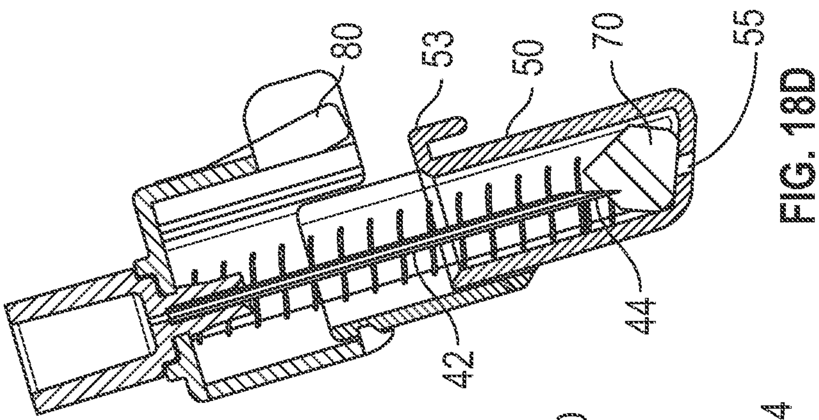
FIG. 18D illustrates a cross-sectional view of a safety needle device of FIG. 16 with the sleeve in an extended and locked position.
Figure 18C:
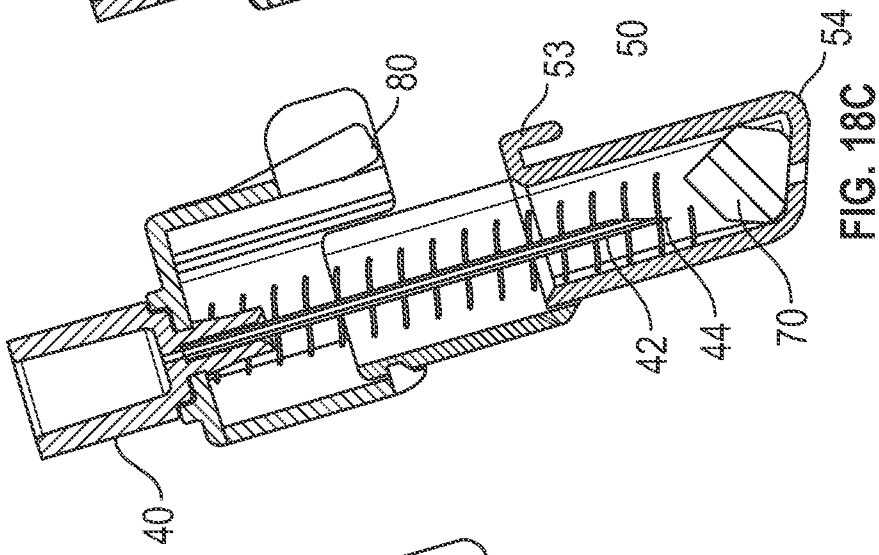
FIG. 18C illustrates a cross-sectional view of a safety needle device of FIG. 16 with the sleeve in an extended position.
Figure 18B:
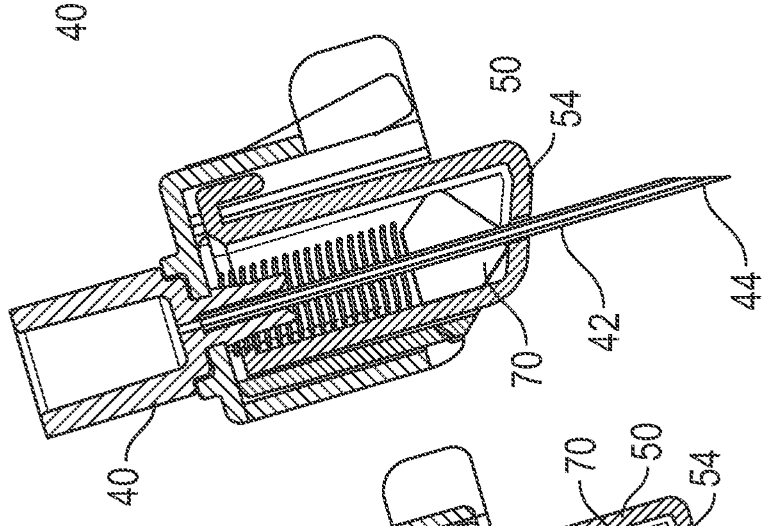
FIG. 18B illustrates a cross-sectional view of a safety needle device of FIG. 16 with the sleeve in a retracted position.

In one or more embodiments, as shown in FIGS. 17 and 18A-D, sliding block comprises a block having a channel within the body of the sliding block attached to spring element is provided. In an initial state shown in FIG. 18A, the cannula is threaded through the channel such allowing the distal tip of the cannula to protrude from the distal end of the retractable sleeve 50 such that distal tip of the cannula is visible to the practitioner while the spring element exerts force on sliding block to maintain the blocking element in a biased state at the distal end of the retractable sleeve 50. Upon administration of an injection to a patient, the retractable sleeve 50 moves in a proximal direction such that the needle cannula moves out of the channel (as shown in FIG. 18B) allowing the sliding block to rotate to an unbiased state such that the distal tip 44 of the needle cannula 42 is prevented from re-entering the diagonal channel within the body of the sliding block to prevent exposure of the practitioner from the distal tip 44 of needle cannula 42 (as shown in FIG. 18D).

If the distal tip of the cannula attempts to pass back through the channel, the distal tip will be buttressed by the body of the sliding block thus causing the distal tip to remain safely disposed within the housing 20 and prevented by the tether 30 and sliding block from exiting the confines of the housing 20, as shown in FIG. 18D.

Figure 18A:
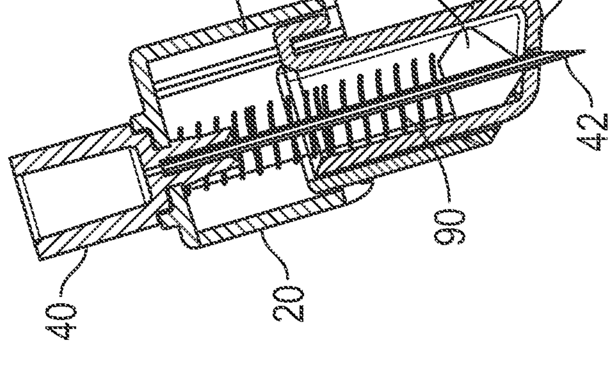
FIG. 18A illustrates a cross-sectional view of a safety needle device of FIG. 16 with the sheath in an initial position.

When the needle cannula 42 is withdrawn from the patient, the patient's skin no longer obstructs forward movement of the retractable sleeve 50, and the retractable sleeve 50 then moves to the extended position as shown in FIG. 18C. As shown in FIG. 18A, the retractable sleeve 50 has an opening 55 through which the needle cannula 42 extends in an initial position.

The misalignment of the needle cannula 42 with the channel of the sliding block prevents the needle cannula 42 from extending back out of the channel of the sliding block after use. Furthermore, the sliding block may be made of strong material to prevent the distal tip 44 of the needle cannula 42 from piercing through the blocking element.

Figure 19B:
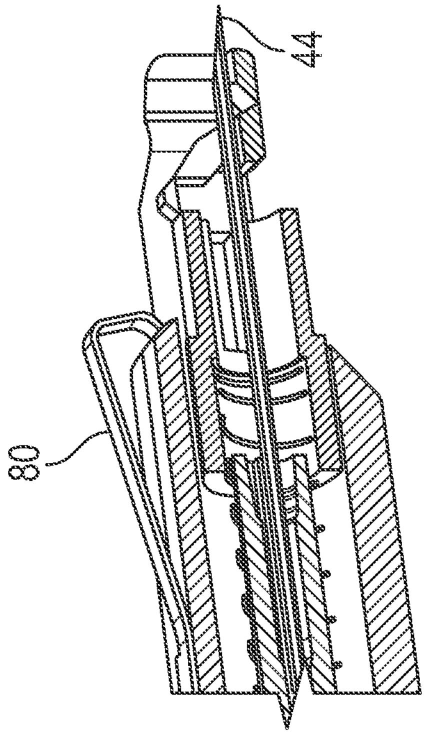
FIG. 19B illustrates a cross-sectional view of the device of FIG. 19A with the sleeve in a partially extended position.
Figure 19C:
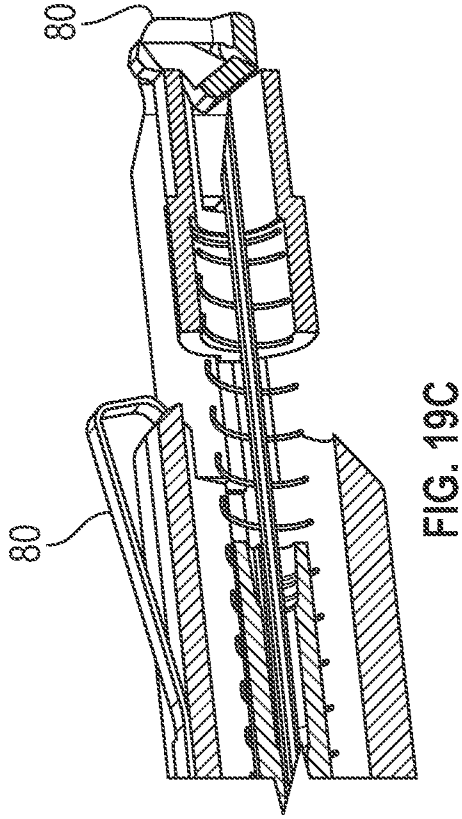
FIG. 19C illustrates a cross-sectional view of the device of FIG. 19A with the sleeve in a retracted position.
Figure 19A:
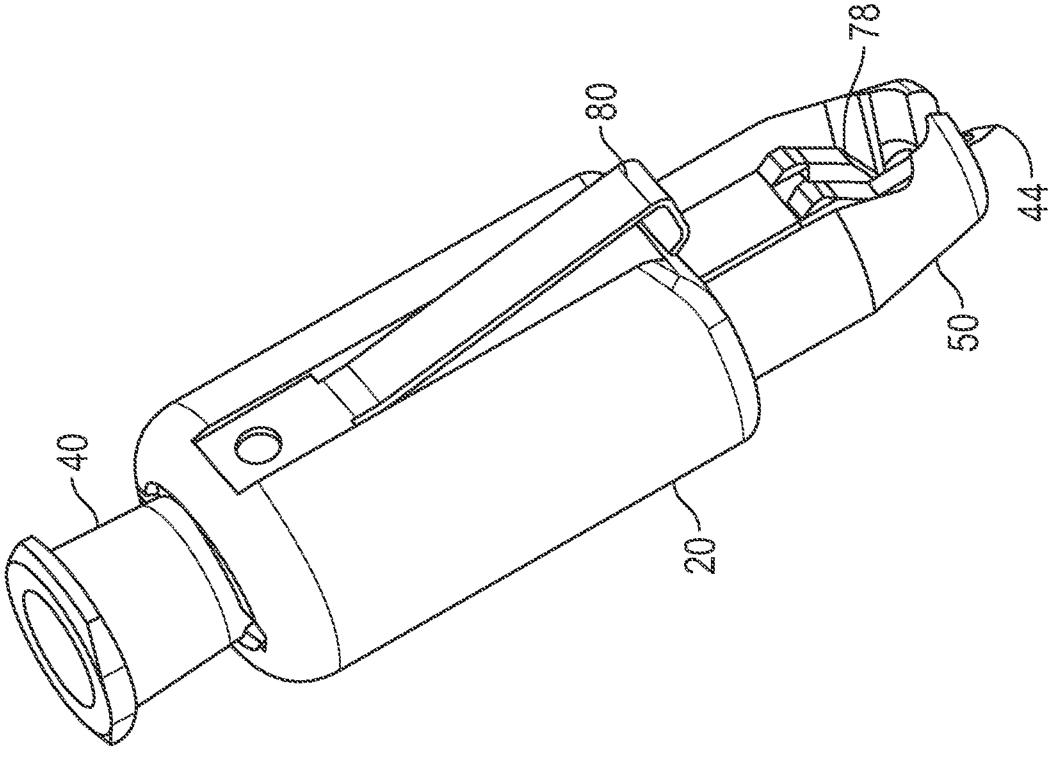
FIG. 19A illustrates a perspective view of a safety needle device according to an alternate embodiment having a living hinge with the sleeve in starting position and locked position.

FIGS. 19A-C show an alternate embodiment having a locking member including a living hinge 78 in combination with an activation latch 80 to bias the living hinge in order to achieve lockout and thereby preventing the needle from exiting the retractable sleeve 50 after completion of an injection. Upon lockout (FIG. 19C), the distal tip 44 of needle cannula 42 will be buttressed by the body of living hinge thus causing the distal tip to remain safely disposed within the housing 20. In this way, the device is a single-use passive safety needle device, as the sleeve 50 automatically covers the distal end of the needle after a patient has been injected and the needle has been removed from the patient. Thus, the needle distal tip is shielded by a sleeve or sheath automatically after the needle cannula is removed from a subject or patient. A practitioner or user of the device does not have to activate the sleeve or sheath by pressing a button on the device, twisting the device or taking any other action.

Figure 20C:
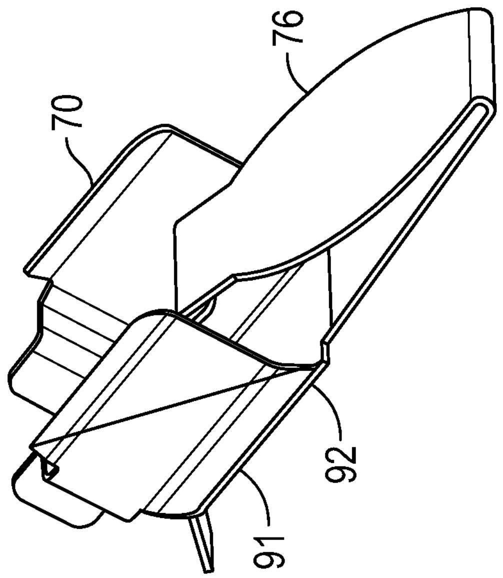
FIG. 20C illustrates a perspective view the latch locking member of the safety needle device of FIG. 20A.
Figure 20B:
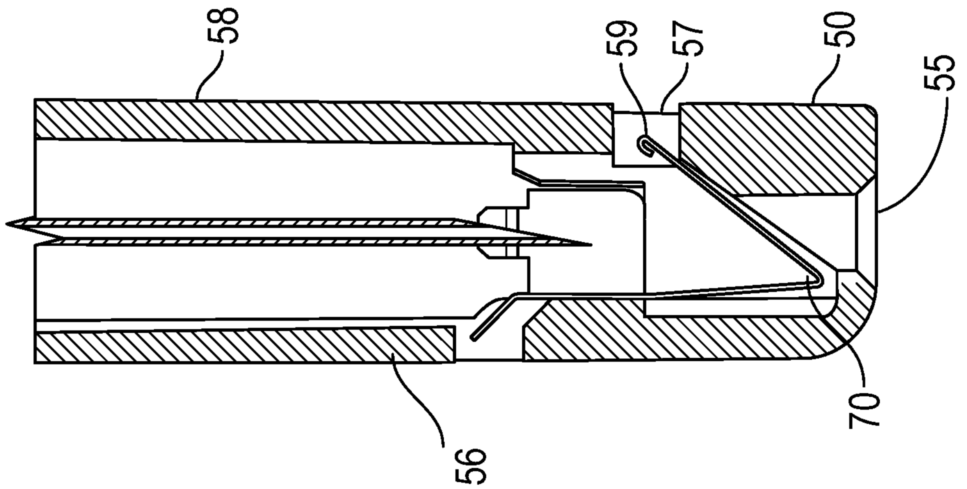
FIG. 20B illustrates a cross-sectional view of a safety needle device of FIG. 20A with the sleeve in an extended position.
Figure 20A:
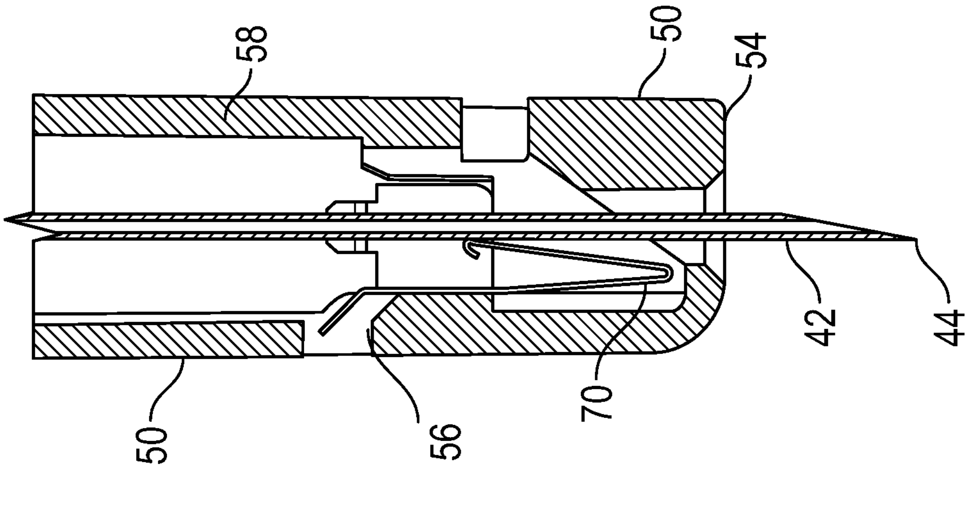
FIG. 20A illustrates a cross-sectional view of a safety needle device according to an alternate embodiment having a tether and latch locking member with the sleeve in an initial position.
Figure 21D:
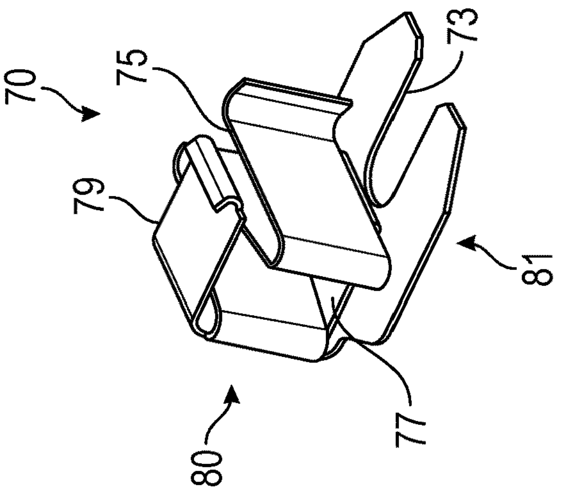
FIG. 21D illustrates a perspective view of the locking member used in the safety needle device of FIG. 21A.
Figure 21C:
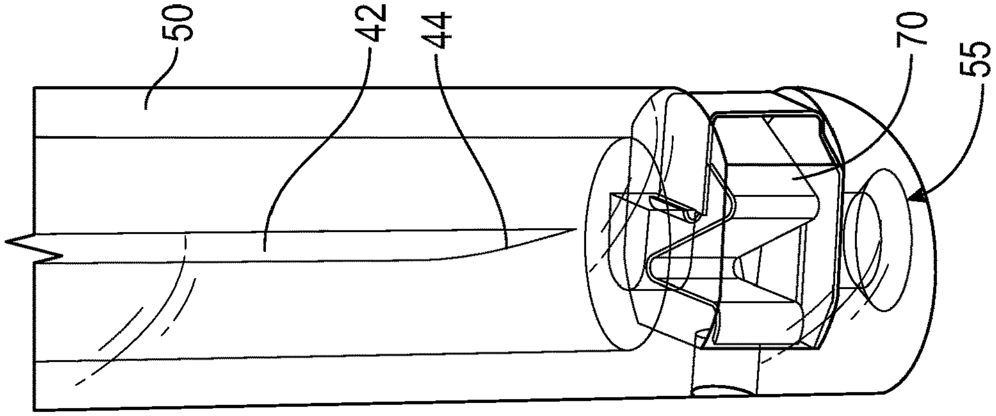
FIG. 21C illustrates a perspective view of a distal portion the safety needle device of FIG. 21A with the sleeve in an extended and locked position.
Figure 21B:
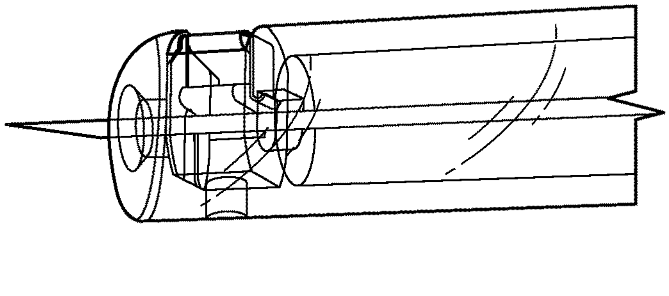
FIG. 21B illustrates a partial perspective view of a distal portion of the safety needle device of FIG. 21A with the sleeve in an initial position.
Figure 21A:
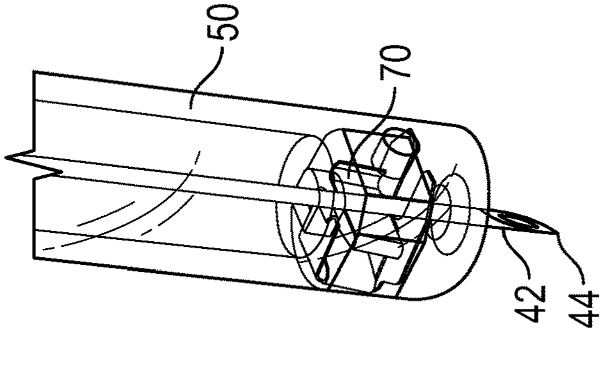
FIG. 21A illustrates a partial perspective view of a distal portion of a safety needle device according to an alternate embodiment having a locking member with a U-shaped clip and a slot to nest the needle cannula with sleeve in an initial position.
Figure 21E:
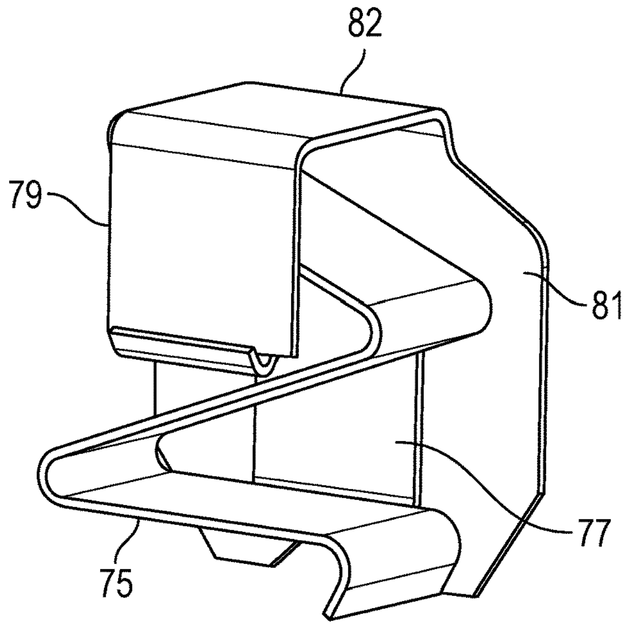
FIG. 21E illustrates a rear perspective view of the locking member used in the safety needle device of FIG. 21A.
Figure 21F:
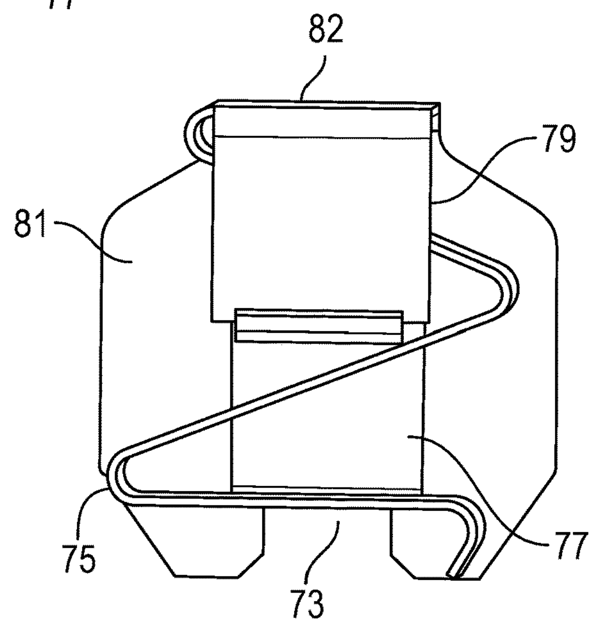
FIG. 21F illustrates a rear view of the locking member used in the safety needle device of FIG. 21A.
Figure 21G:
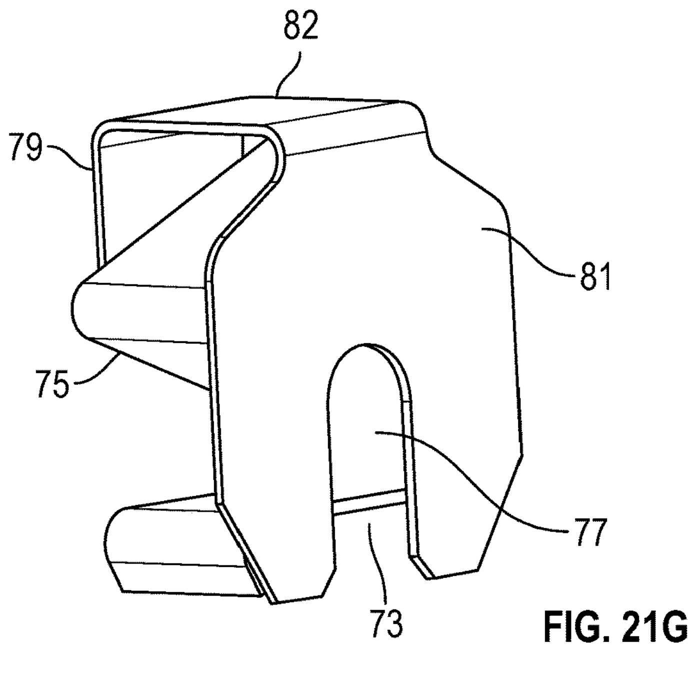
FIG. 21G illustrates a front perspective view of the locking member used in the safety needle device of FIG. 21A.

FIGS. 20A-C shows yet another alternate embodiment having a locking member 70 in the form of a lockout latch to prevent the needle from exiting the retractable sleeve 50 after completion of an injection. The locking member 70 in the form of a lockout latch has an overall three-dimensional U-shape (as shown in FIG. 20C), including a proximal end 91 and a distal end 92. The proximal end 91 of the locking member 70 is connected to a sidewall 56 of the retractable sleeve. The distal end of the locking member 70 includes a V-shaped biasing member 76 that rests against the needle cannula 42 in an initial state and interacts with a recess 57 on the opposite sidewall 58 of the retractable sleeve 50 when the retractable sleeve is in an extended position. In the starting position, locking member 70 in the form of a lockout latch is disposed in the retractable sleeve and rests in a compressed position against the body of the needle cannula 42. The V-shaped biasing member slides along the needle cannula 42 while the needle cannula 42 is inserted into a subject or a patient, and the sheath or sleeve 50 moves in a proximal direction as the sheath or sleeve 50 end face contacts the patient's or subject's skin. When the needle cannula 42 is removed from the subject or patient, and the sheath or sleeve 50 moves in a distal direction, and the V-shaped biasing member slides past the needle cannula 42 the locking member 70 in the form of a lockout latch covers the distal tip 44 of the needle cannula 42 in the extended position. After the device is activated, a spring element (not shown) pushes the retractable sleeve forward to allow the retractable sleeve 50 to extend past the distal tip 44 of needle cannula 42 which allows stored energy in the compressed V-shaped biasing member 76 to be released such that it activates and locks the device when hook 59 on the distal tip of the V-shaped biasing member 76 interacts with a recess 57 on the opposite sidewall 58 of the retractable sleeve 50. Locking member 70 in the form of a lockout latch is able to clip over the distal tip 44 of the needle cannula 42 thereby passively locking out the safety needle device 10 and preventing needle stick injury to the practitioner. The locking member 70 in the form of the lockout latch inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position. In one or more embodiments, locking member 70 in the form of a lockout latch may be a metal latch.

FIGS. 21A-D show an alternate embodiment including a locking member 70 in the form of a spring clip, which has an overall three-dimensional U-shape or L-shape, including a proximal leg 79, a lateral leg 82 and a distal leg 81. As best shown in FIGS. 21D-G, the locking member 70 includes a slot 73 sized and configured to allow a needle cannula 42 to nest therein when the sheath or sleeve 50 is in the initial position and the distal tip 44 of the needle cannula 42 is exposed. The needle cannula 42 slides in the slot 73 while the needle cannula 42 is inserted into a subject or a patient, and the sheath or sleeve 50 moves in a proximal direction as the sheath or sleeve 50 end face contacts the patient's or subject's skin. When the needle cannula 42 is removed from the subject or patient, and the sheath or sleeve 50 moves in a distal direction, the needle cannula 42 slides in the slot 73. The slot 73 is located within the distal leg 81, and a biasing member 75 extends from the lateral leg 82. The biasing member 75 can include a flat spring, a tong spring or a double loop tong spring as shown in FIGS. 21D-G. A gate 77 in the form of a flat sheet protrudes from the biasing member 75. In the initial position, the biasing member 75 rests against the body of the needle cannula 42 to keep gate 77 out of alignment with opening 24 of sleeve 50 and the slot 73 of the of the locking member 70. In the retracted state, the biasing member 75 rides along the needle cannula 42. After the device is activated, the retractable sleeve 50 moves forward to allow the retractable sleeve 50 and the gate 77 of biasing member 75 to extend past the distal tip 44 of needle cannula 42 which allows stored energy in the compressed flat spring to be released such that the gate 77 covers the slot 73 thereby passively locking out the safety needle device 10 and preventing needle stick injury to the practitioner. The locking member 70 in the form of a U-shaped clip inhibits reuse of the safety needle device 10 by inhibiting further translational movement of the retractable sleeve 50 within the housing body 23 by covering the distal tip 44 of the needle cannula 42 in the extended position. Needle cannula 42 is obscured from view when the retractable sleeve is in the extended position.

Figures 22A, 22B, 22C, 22D, 22E, 22F:
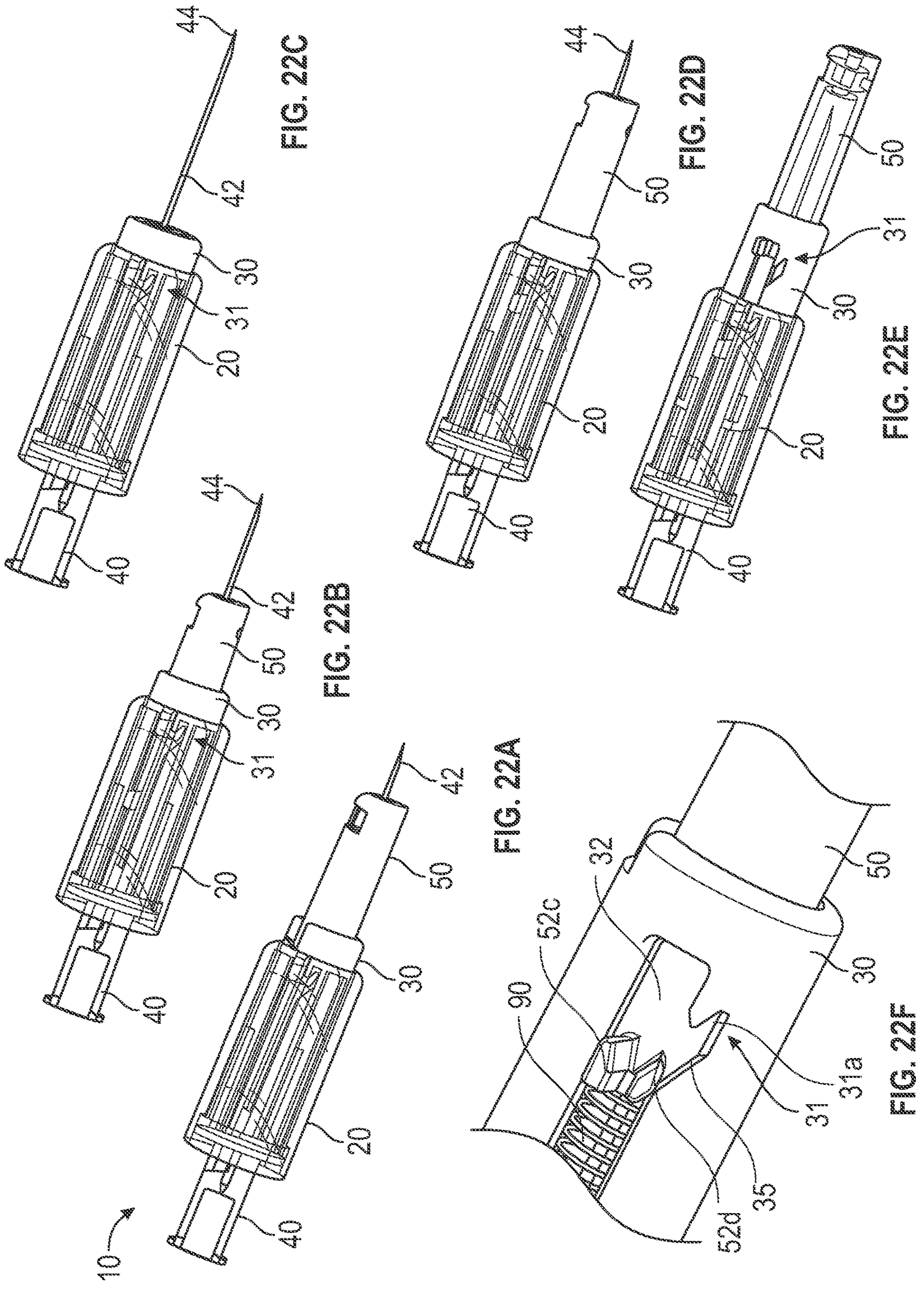
FIG. 22A illustrates a perspective view of a safety needle device according to an alternate embodiment having a tether including a hook with the sleeve in an initial position.
FIG. 22B illustrates a perspective view of the safety needle of FIG. 22A with the sleeve in a partially retracted position.
FIG. 22C illustrates a perspective view of the safety needle device of FIG. 22A with the sleeve in a fully retracted position.
FIG. 22D illustrates a perspective view of the safety needle device of FIG. 22A with the sleeve in partially extended position.
FIG. 22E illustrates a perspective view of the safety needle device of FIG. 22A with the sleeve in a fully extended and locked position.
FIG. 22F illustrates a partial view of the safety needle device of FIG. 22A.

FIGS. 22A-F show an alternate embodiment with a tether having a hook-shaped portion that prevents one or protrusions (first protrusion 52*c*) and second protrusion 52*d*) from rotation prior to retractable sleeve advancement. In one or more embodiments, the retractable sleeve has one or more protrusions 52*c*, 52*d* in the form of a stabilization bar that interacts with a slot in the housing to rotationally key the sleeve and housing. A second protrusion 52*d* engages the tether and activates the safety device by causing the tether to rotate relative to the housing thereby releasing the tether from the housing. In one or more embodiments, the enlarged first guide path 31 may comprise a hook-shaped portion (or branch) 31*a* defining a hook-shaped portion that engages the second protrusion 52*d* and resists or prevents relative rotation of the tether 30 and the sleeve 50. The one or more protrusions may comprise a single radially extending protrusion having a first protrusion 52*c* having a first height and a second protrusion 52*d*extending laterally from the first protrusion 52*c*, the second protrusion 52*d* may have a second height that is less than the first height, and the second protrusion 52*d* may have a surface that nests in the hook-shaped portion 31*a* when the device is packaged, removed from the package and in an initial position as shown in FIG. 22A. FIG. 22F shows an enlarged view of the first guide path and a second guide path 32. In use, the device 10 is removed from a package, and the sleeve 50 is in an initial position (FIG. 22A) with the distal tip 44 of the needle cannula 42 exposed so that the distal tip 44 of the needle cannula 42 can be inserted into the skin of a patient or through the surface of a vial to fill the syringe (not shown). FIG. 22B shows the sleeve 50 moved in a proximal direction as the needle cannula 42 is inserted further into a patient, and the sleeve retracts into the housing 20. At this point, the second protrusion 52*d* has moved out of the first guide path 31, pushed against the ramped surface 35, causing the tether 30 to rotate, and activating the device, causing the spring element 90 to bias the sleeve 50 in the distal direction. FIG. 22C shows the sleeve 50 fully retracted into the housing 20, and as the needle is withdrawn from a patient, the sleeve is biased to move in the distal direction as shown in FIG. 22D. When the needle cannula 42 distal tip 44 is removed from the patient, the sleeve 50 by the spring element 90 to cover the distal tip 44 as shown in FIG. 22E. A blocking element at the end of the sleeve 50 prevents the needle cannula 42 distal tip 44 from exiting the sleeve 50, thereby protection from needle cannula 42 sticks.

Figure 23:
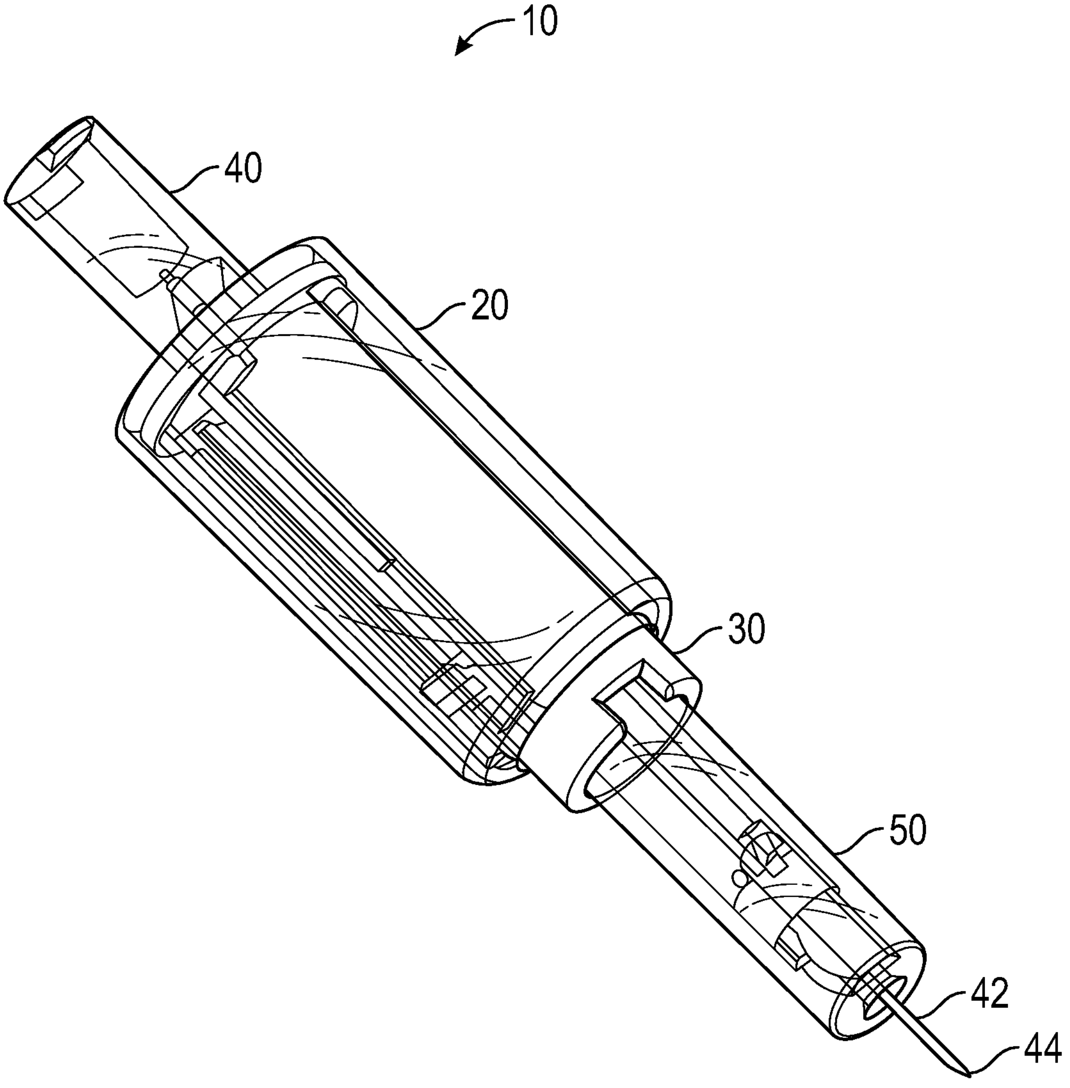
FIG. 23 illustrates a perspective view of a safety needle device according to an alternate embodiment.

As shown in FIG. 23, one or more embodiments include an anti-fire feature. In one embodiment, the slot in the tether interfaces with one or more ribs, tabs or bars disposed in a cap or hard package so that the safety needle device 10 does not "mis-fire" in transit or storage. Any suitable caps or packaging comprising a safety feature may be used in conjunction with the safety needle device disclosed herein.

Figure 24A:
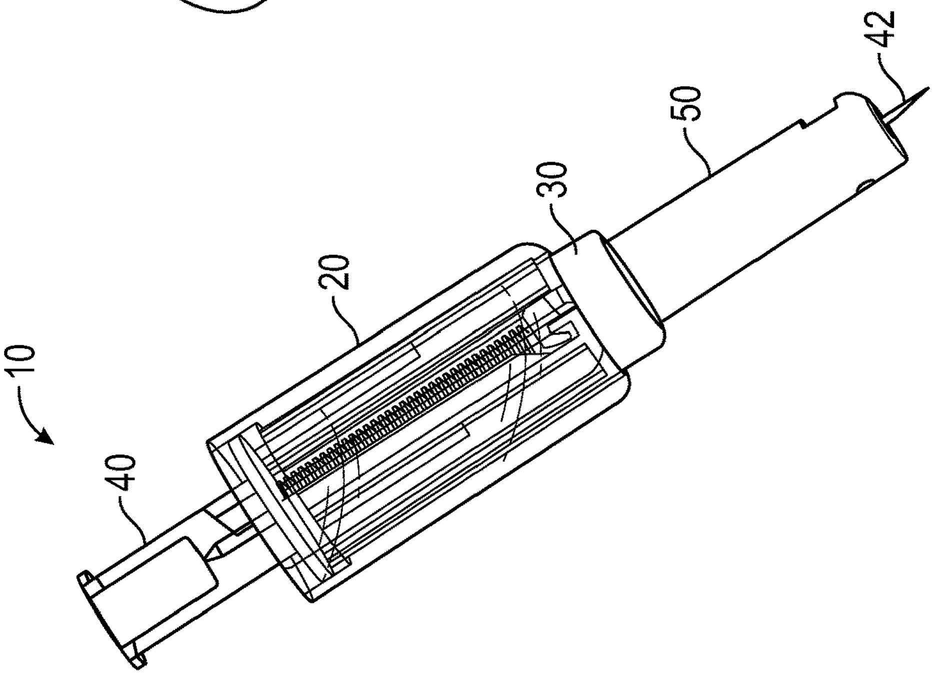
FIG. 24A illustrates a perspective view of a safety needle device according to an alternate embodiment having a retractable sleeve.
Figure 24B:
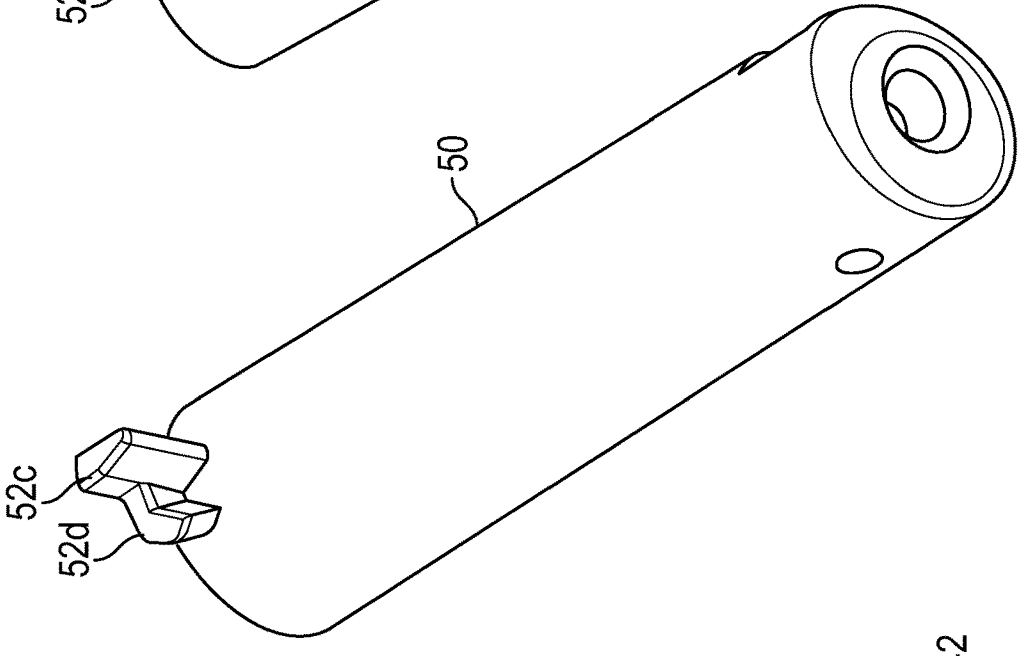
FIG. 24B illustrates a perspective view of a sleeve of a safety needle device according to an alternate embodiment showing an alternate protrusion configuration.
Figure 24C:
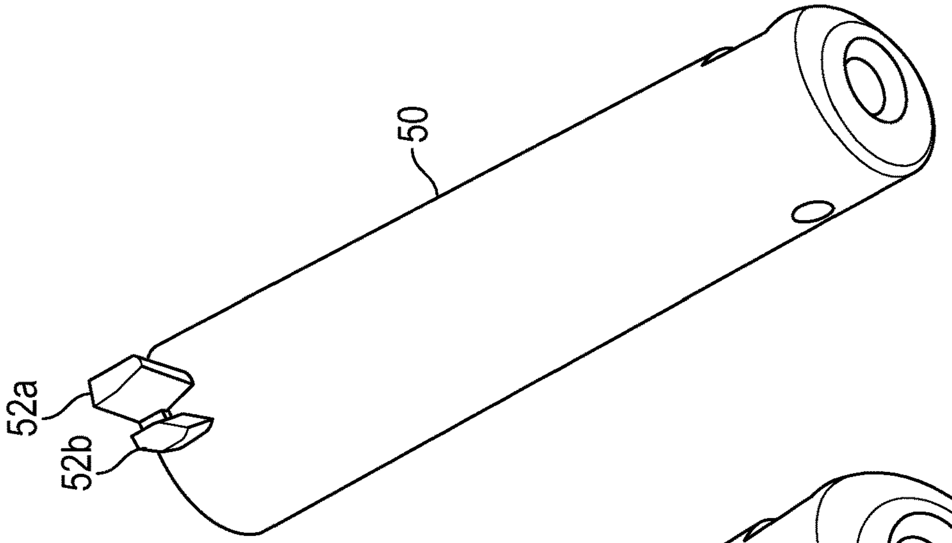
FIG. 24C illustrates a perspective view of a sleeve of a safety needle device according to an alternate embodiment showing an alternate protrusion configuration.
Figure 25:
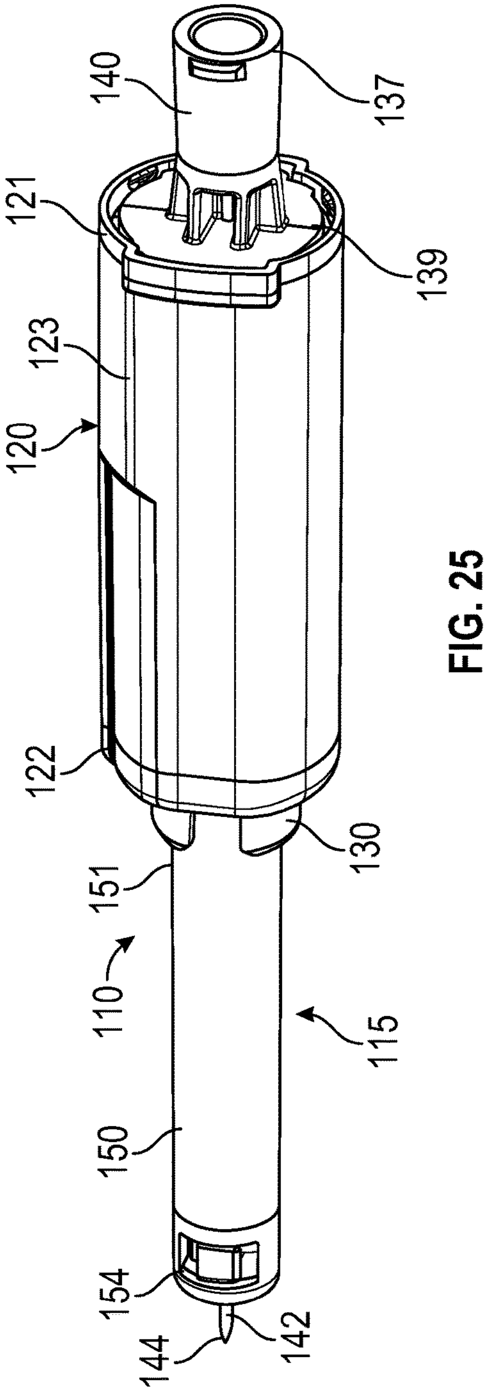
FIG. 25 illustrates a side perspective view of an alternate embodiment of a safety needle device having a retractable sleeve.
Figure 26:
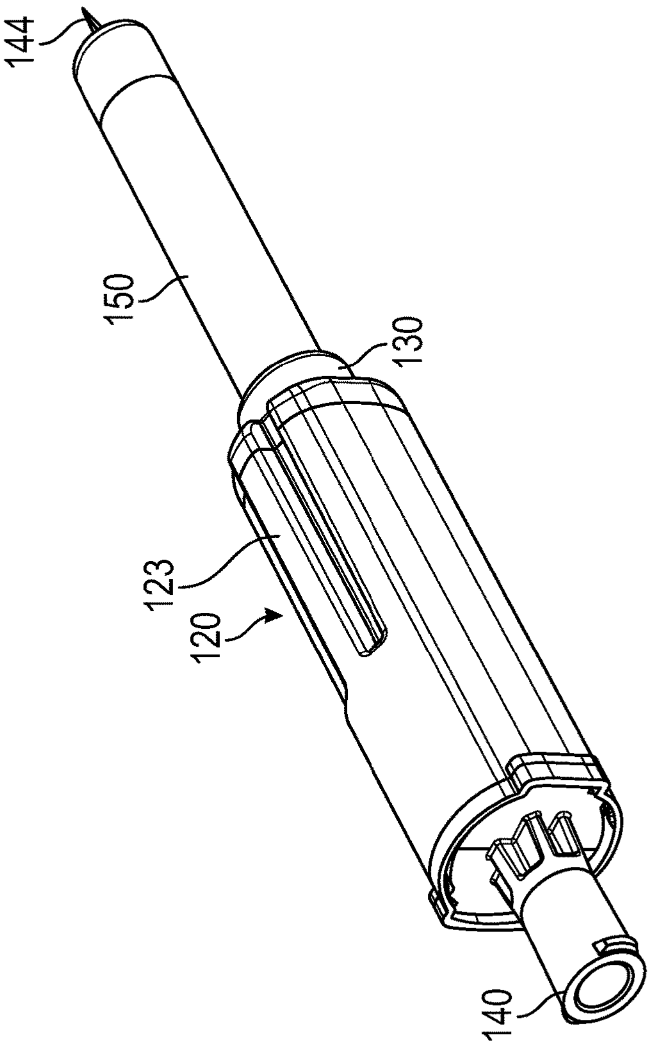
FIG. 26 illustrates a rear perspective view the device of FIG. 25.

FIG. 24A illustrates a perspective view of a safety needle device according to an alternate embodiment having a retractable sleeve 50 with alternative protrusion configurations shown in FIGS. 24B and 24C. As shown in FIG. 24B, an embodiment of the retractable sleeve has one or more protrusions that are integral or connected, first protrusion 52*c* having a first height that is greater than second height of second protrusion 52*d*. As shown in FIG. 24C, an alternate embodiment of the retractable sleeve has one or more protrusions which are separated from each other, first protrusion 52*a* having a first height than the second height of second protrusion 52*b*.

In one or more embodiments, one or more protrusions are disposed on or near the proximal end of the retractable sleeve 50 to key the retractable sleeve to the housing. The one or more protrusions allow the retractable sleeve to move in and out of the housing but prevent rotation of the retractable sleeve relative to the housing.

In one or more embodiments, one or more protrusions reduce wobbliness between the housing and retractable sleeve, as well as, guide the retractable sleeve from an initial position in the enlarged first guide path of the tether to a second position in the narrowed second guide path of the tether.

In one or more embodiments, the one or more protrusions are in the shape of a T-Bar. The T-shape at the end of the one or more protrusions helps to reduce wobbliness between the housing and retractable sleeve by adding additional guidance and support.

Upon movement of the retractable sleeve in the proximal direction, the T-shaped one or more protrusions move along from the initial position in the enlarged first guide path of the tether to a second position in the narrowed second guide path of the tether that causes the tether to rotate.

In one or more alternate embodiments, the device includes one or more protrusions and one or more pegs on the retractable sleeve that engages with the rotating tether but does not engage with the housing. The one or more pegs activate the device. Upon movement of the retractable sleeve in the proximal direction, the one or more pegs move along a path that causes the tether to rotate while the sleeve is held rotationally fixed by a separate one or more protrusions moving the tether from a first position to a second position. The one or more pegs can be located at any orientation (0-360 degrees) relative to the stabilization feature including but not limited to 0 degrees (same feature), 180 degrees, side by side, or separated by only a few degrees.

In one or more alternative embodiments, the one or more protrusions are in the shape of a dovetail.

Stroke length is the sum of needle cannula length and retractable sleeve 50 length for lock-out travel. The distance between distal end of retractable sleeve 50 and distal tip 44 of needle cannula 42 is a stack-up of tolerances and safety margin to insure needle stick injury (NSI) is prevented following use.

In one or more embodiments, overall length of the safety needle device may be reduced when the spring element is allowed to collapse inside both the retractable sleeve 50 and housing 20. Thus reducing overall length by the solid height and subsequently lowering forces applied to a patient's skin.

In one or more embodiments, the safety needle device can include a cap that is removably coupled to the housing to reduce or prevent contamination of the needle cannula during shipping and storage of the safety needle device. The cap is generally kept in the closed position until just prior to an injection and/or aspiration procedure, at which time the cap is removed from the housing. In some embodiments, cap may be configured to assist in properly drawing a dose from a vial.

Referring now to FIGS. 25-30, specific embodiments and features of a safety needle device 110 are shown. The device 110 may be a safety needle device 110, or a single use passive safety device, which means that a protective cover that shields a distal end of the needle cannula is covered by a cover or sleeve that is automatically deployed by the device to move over the needle cannula tip, without the user or practitioner activating a button, lever, etc.

The safety needle device 110 comprises a hub 140 having a proximal end 137 that can be coupled to a syringe (not shown) and a distal end 139. The hub has a needle cannula 142 extending therefrom in a distal direction. The needle cannula has a longitudinal axis and distal tip 144.

Figure 27:
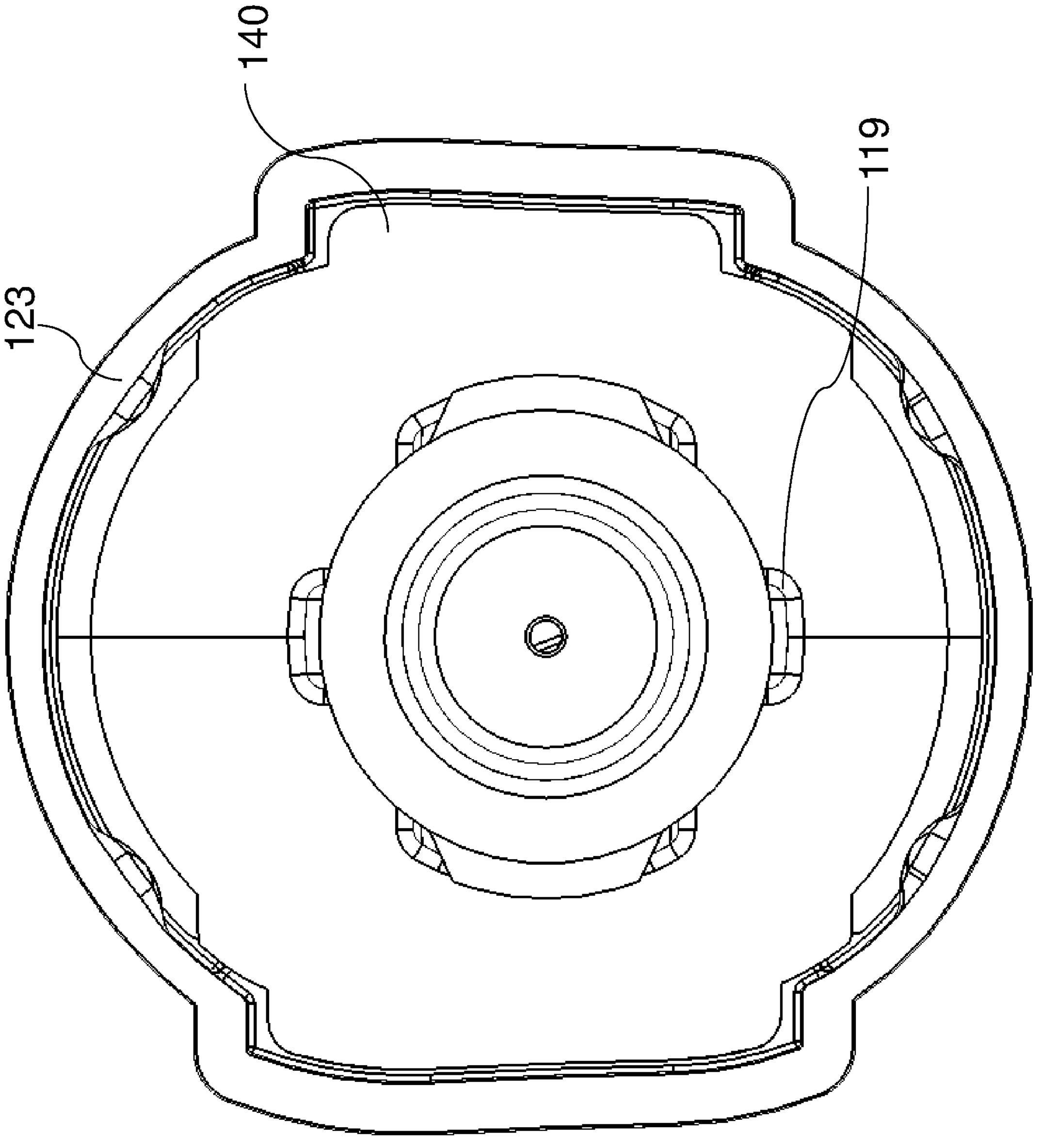
FIG. 27 illustrates a rear of the device of FIG. 25.
Figure 28:
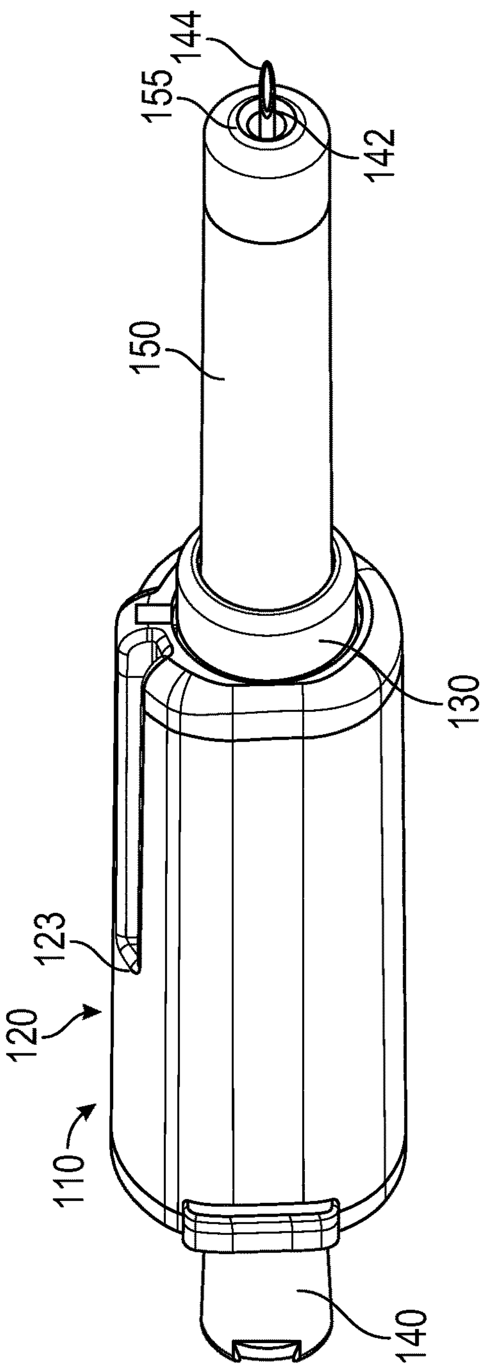
FIG. 28 illustrates a front perspective view of the device of FIG. 25.
Figure 29:
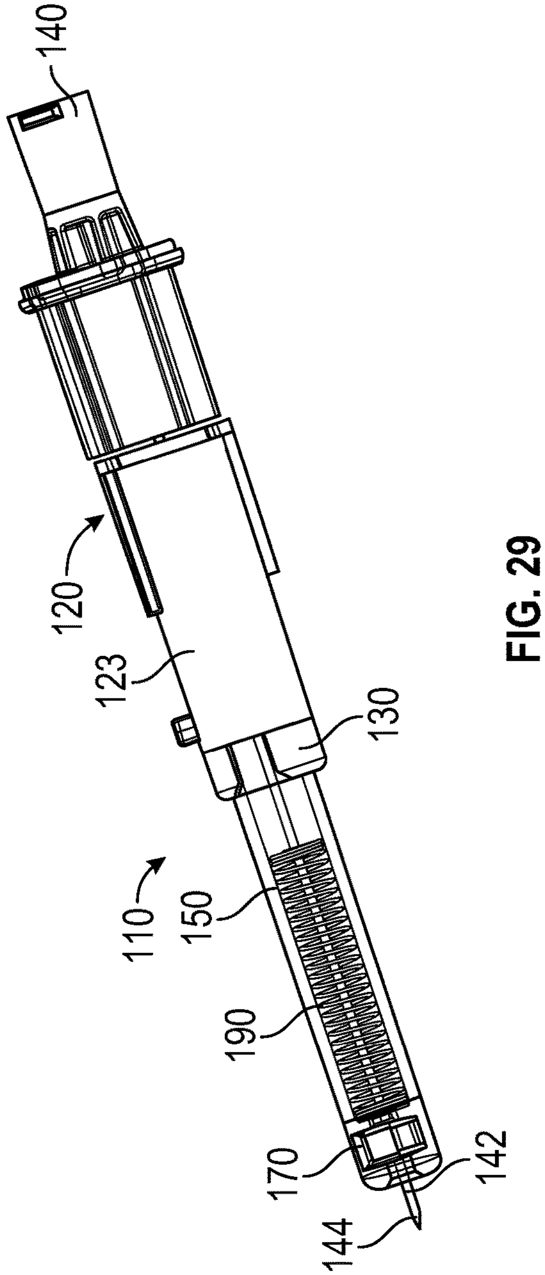
FIG. 29 illustrates a side view the device of FIG. 25.
Figure 30:
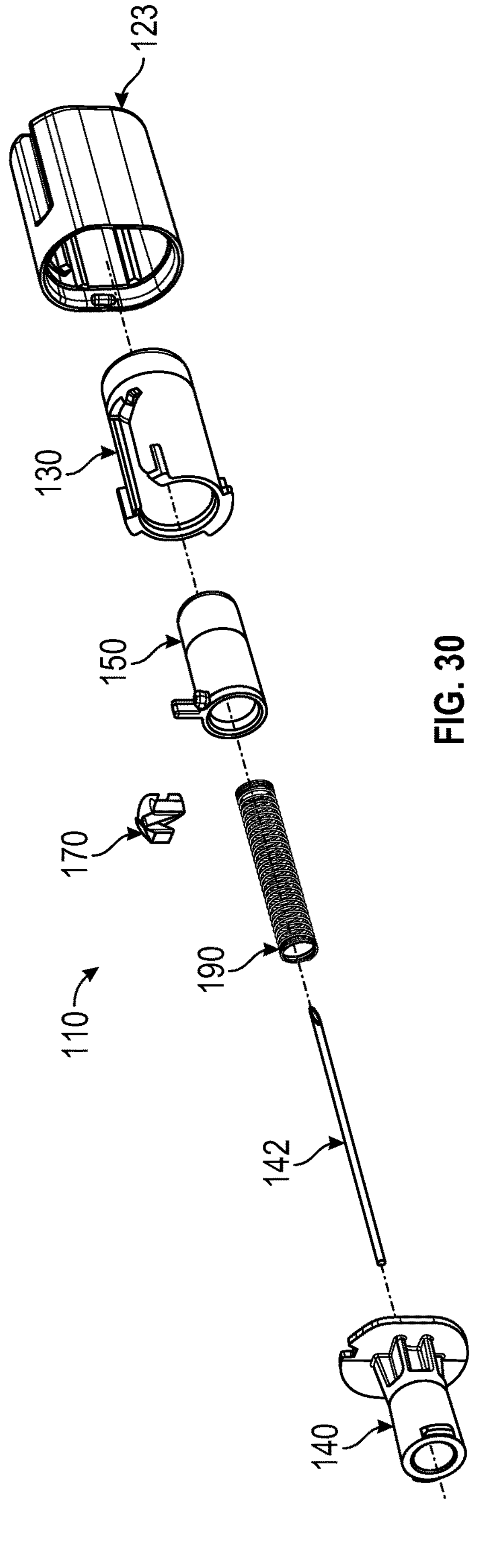
FIG. 30 illustrates an exploded perspective view of the device of FIG. 25.
Figure 31:
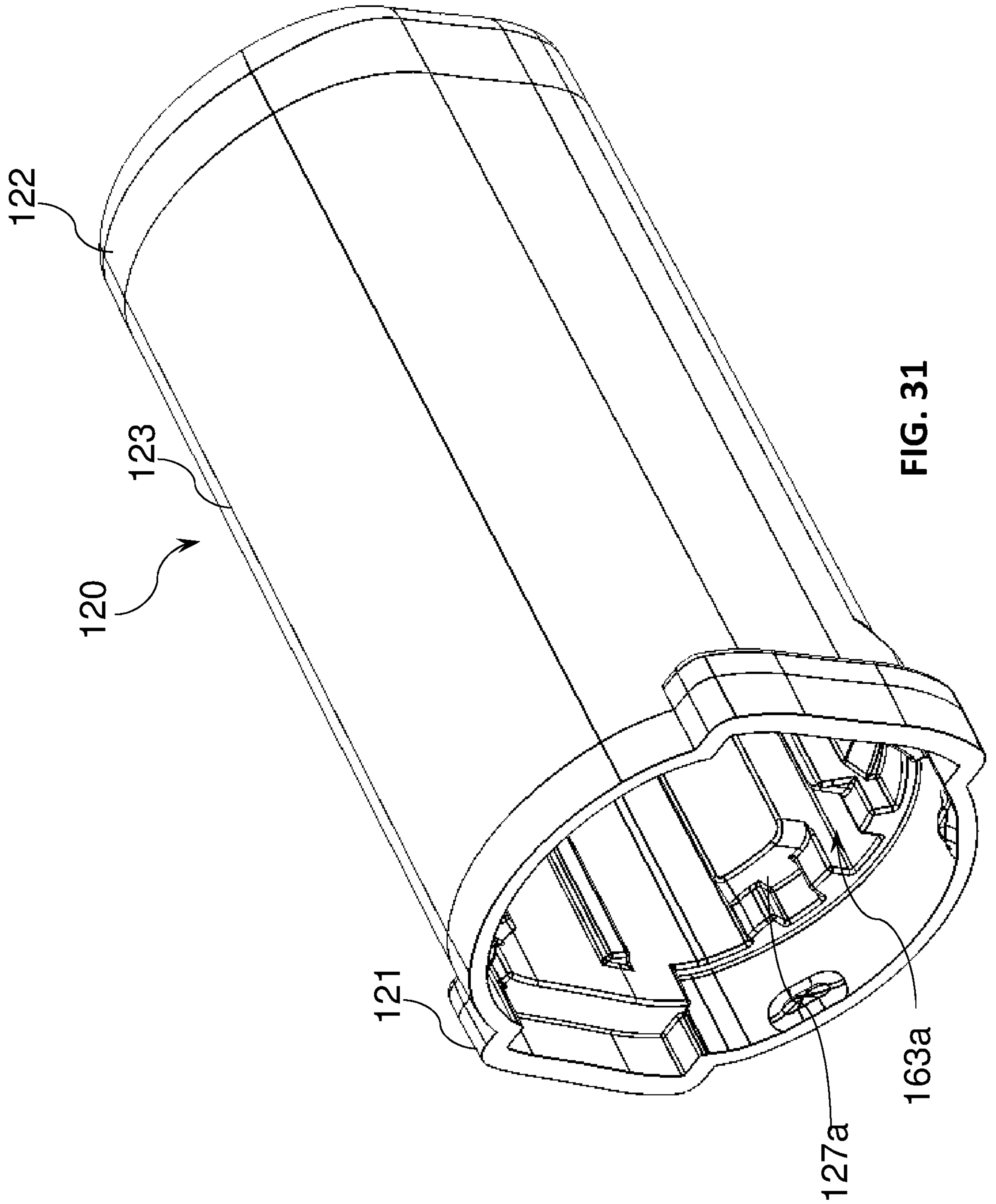
FIG. 31 illustrates a rear perspective view of the housing of the device of FIG. 25.

The device 110 further includes a housing 120 having a proximal end 121, a distal end 122, and a housing body 123, the hub 140 being attached to the housing 120 and the distal tip 144 of the needle cannula 142 extending past the distal end 122 of the housing 120. The device 110 further includes a needle cannula cover 115 comprising an elongate sleeve 150 having a proximal end 151 and a distal end 154. The needle cannula cover 115 is slidably movable in a distal and proximal direction inside the housing and is biased to move in a distal direction toward the distal tip 144 of the needle cannula 142 when the device is activated. The needle cannula cover 115 has an initial starting position at which the distal tip 144 of the needle cannula 142 is exposed, an intermediate position at which the needle cannula cover 115 is moved in a proximal direction to move the distal end of the needle cannula cover 115 a distance further from the distal tip 144 of the needle cannula 142, and an extended position at which the distal end 154 of the needle cannula cover, namely the distal end 154 of the sleeve 150 extends past the distal tip 144 of the needle cannula 142 to cover the distal tip 144. The device further includes a locking element in the form of a clip 170 disposed adjacent the distal end 154 of the sleeve 150 of the needle cannula cover 115, the clip 170 preventing proximal movement of the sleeve and exposure of the distal tip 144 of the needle cannula 142. FIG. 27 shows a view of the device 110 from the proximal end with the hub 140 fitted within the housing body 123. FIG. 28 shows an alternate perspective view of the device from the distal end thereof, and FIG. 29 shows a cross-sectional view of the device, showing the locking member in the sleeve 150, and the spring 190, which biases the sleeve 150 forward when released from the initial position. FIG. 30 shows an exploded view of the device 110.

As will be discussed further below the locking member in the form of the clip 170 is slidably engageable along the length of the needle cannula 142 when the device 110 is in use.

The sleeve 150 of the needle cannula cover 115 has an opening 155 at the distal end 154 that permits the needle cannula 142 to slide therethrough, and the clip 170 slides over the distal tip 144 of the needle cannula 142 when the sleeve 150 needle cannula cover 115 is in the extended position, blocking the distal tip 144 of the needle cannula 142 and preventing the distal tip 144 of the needle cannula 142 from protruding through the opening 155.

Figure 56:
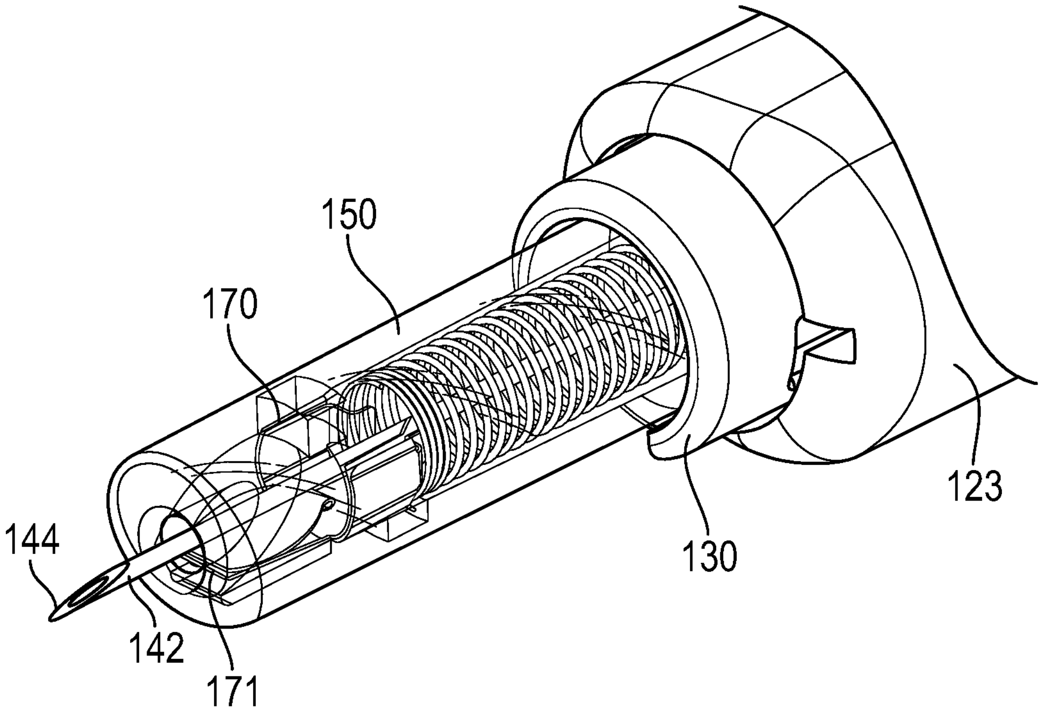
FIG. 56 shows a partial front perspective view of a device showing the needle cannula distal tip exposed through the sleeve.
Figure 57:
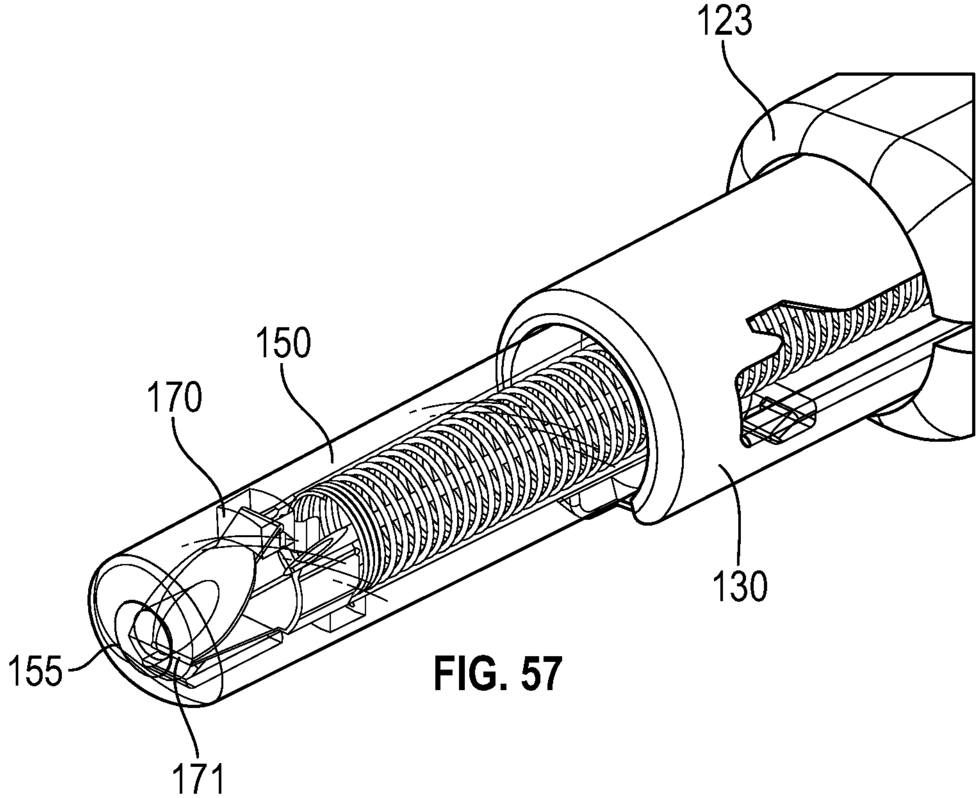
FIG. 57 shows a partial front perspective view of the device shown in FIG. 58 with the sleeve covering the needle cannula and the clip engaging the distal tip of the needle cannula.

In one or more embodiments, the clip 170 can comprise a latch having a bend 171 at a distal end. The clip 170 is biased to slide over and cover the distal tip 144 of the needle cannula, as shown in FIGS. 56 and 57 and prevent movement of the distal tip 144 through an opening 155 in the sleeve 150 of the needle cannula cover 115.

As shown, the sleeve 150 of the needle cannula cover 115 has an opening 155 at the distal end 154 that permits the needle cannula 142 to slide therethrough, and the clip 170 is a spring-biased blocking element that blocks the opening 155 to prevent the distal tip 144 of the needle cannula 142 from protruding through the opening 155 when the sleeve 150 of the needle cannula cover 115 is in the extended position.

In one or more embodiments of the device, the spring-biased blocking element has a spring that is biased in a direction transverse to the longitudinal axis of the needle cannula 142. In other words, the needle cannula moves along the long axis of the device 110 in a proximal and distal direction. This axis may be considered a z axis in a Cartesian coordinate system. The clip 170 comprises the blocking element is biased in a direction in the x-y plane to slide a gate to block the opening 155 at the distal end 154 of the sleeve 150. This will be discussed in more detail below.

In one or more embodiments, the blocking element comprises a gate 177 that is biased to move to a closed position to block the opening 155 in sleeve 150 of the needle cannula cover 115, and the blocking element is held open by the needle cannula when the cover is in the initial position and the intermediate position. In one or more embodiments, as shown in FIGS. 40-43, there is a pocket 160 adjacent the distal end 154 of the sleeve 150, the pocket 160 configured to securely hold the clip 170 in the pocket 160. In one or more embodiments, as best shown in FIGS. 40-42 and 48-55, the clip 170 has a height $H_c$ and the pocket has a depth D that is at least equal to the height $H_c$ of the clip. In other embodiments, the depth D of the pocket 160 is equal to or greater than the height $H_c$ of the clip. Such a configuration prevents a user of the device 110 from removing the clip from the pocket 160. In one or more embodiments, the top edges 161 of the pocket are narrowed or sharp edges to further make it difficult to access the pocket to remove the clip 170.

Another embodiment of a device provides a safety needle device 110, which can be a safety needle device which comprises a hub 140 having a proximal end that can be coupled to a syringe, the hub 140 having a needle cannula 142 extending therefrom in a distal direction, the needle cannula having a longitudinal axis and distal tip 144. The device 110 also includes a housing 120 having a proximal end, a distal end and a housing body 123, and the hub 140 is attached to the housing 120. The needle cannula 142 and the distal tip 144 extend past the distal end of the housing 120. The device further includes a needle cannula cover 115 comprising an elongate sleeve 150 having a distal end 154, the elongate sleeve 150 of the needle cannula cover 115 slidably movable in a distal and proximal direction inside the housing 120 and being biased to move in a distal direction toward the distal tip 144 of the needle cannula 142. The elongate sleeve 150 of needle cannula cover 115 has an initial position at which the distal tip 144 of the needle cannula 142 is exposed, an intermediate position at which the elongate sleeve 150 needle cannula cover 115 is moved in a proximal direction to move the distal end 154 of the elongate sleeve 150 of the needle cannula cover 115 a distance further from the distal tip 144 of the needle cannula 142, and an extended position at which the distal end 154 of the elongate sleeve 150 of the needle cannula cover 115 extends past the distal tip 144 of the needle cannula 142, the elongate sleeve 150 axially movable with respect to the needle cannula 142. The device further comprises an activation component in the form of tether 130 slidably engaged with the elongate sleeve 150 of the needle cannula cover 115 and positioned intermediate the housing 120 and the elongate sleeve 150 of the needle cannula cover 115, the activation component in the form of the tether 130 being rotationally movable with respect to the housing 120, such that when the activation component in the form of the tether 130 is moved rotationally when the elongate sleeve 150 of the needle cannula cover 115 is moved in a proximal direction from the initial position, the elongate sleeve 150 of the needle cannula cover 115 is activated and biased to move in a distal direction.

In specific embodiments, the activation component in the form of the tether 130 and the elongate sleeve 150 of the needle cannula cover 115 move telescopically within the housing 120 such that the distal tip 144 of the needle cannula is exposed when the activation component in the form of the tether 130 and the elongate sleeve 150 of the needle cannula cover 115 are moved in a proximal direction from the initial position, and the distal tip 144 of the needle cannula 142 is covered when the activation component and the needle cannula cover are moved in a distal direction to the extended position such that the distal end 154 of the elongate sleeve 150 of the needle cannula cover 115 is moved distally past the needle cannula distal tip 144. In this way, the device is a single-use passive safety needle device, as the needle cannula cover automatically covers the distal end of the needle after a patient has been injected and the needle has been removed from the patient. Thus, the needle distal tip is shielded by a needle cannula cover (or a sleeve or a sheath) automatically after the needle cannula is removed from a subject or patient. A practitioner or user of the device does not have to activate the needle cannula cover by pressing a button on the device, twisting the device or taking any other action.

Figure 36:
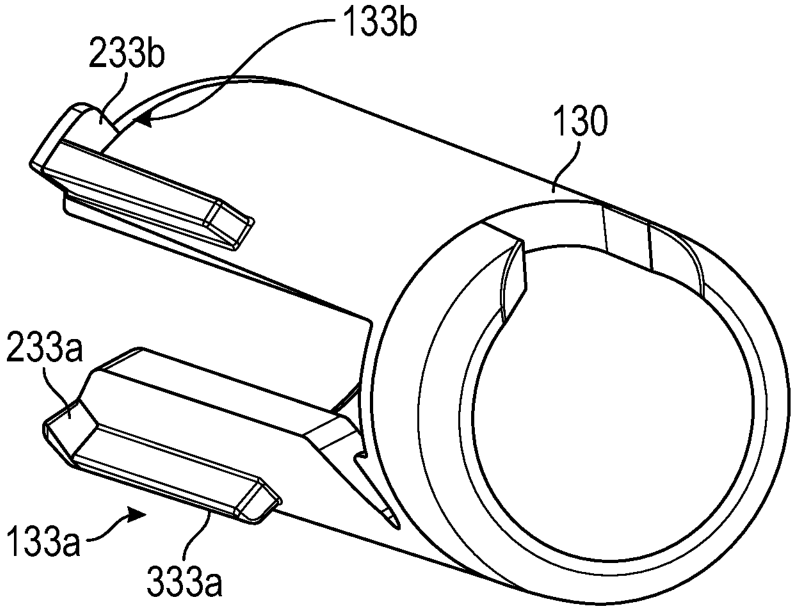
FIG. 36 illustrates an alternate front perspective view of the sleeve of the device of FIG. 25.
Figure 37:
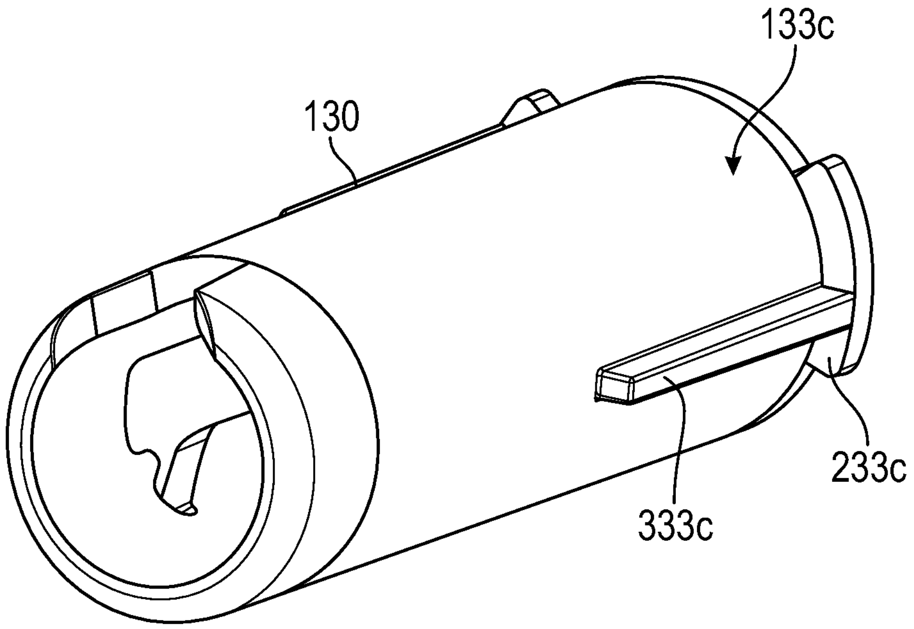
FIG. 37 illustrates an alternate front perspective view of the sleeve of the device of FIG. 25.
Figure 39:
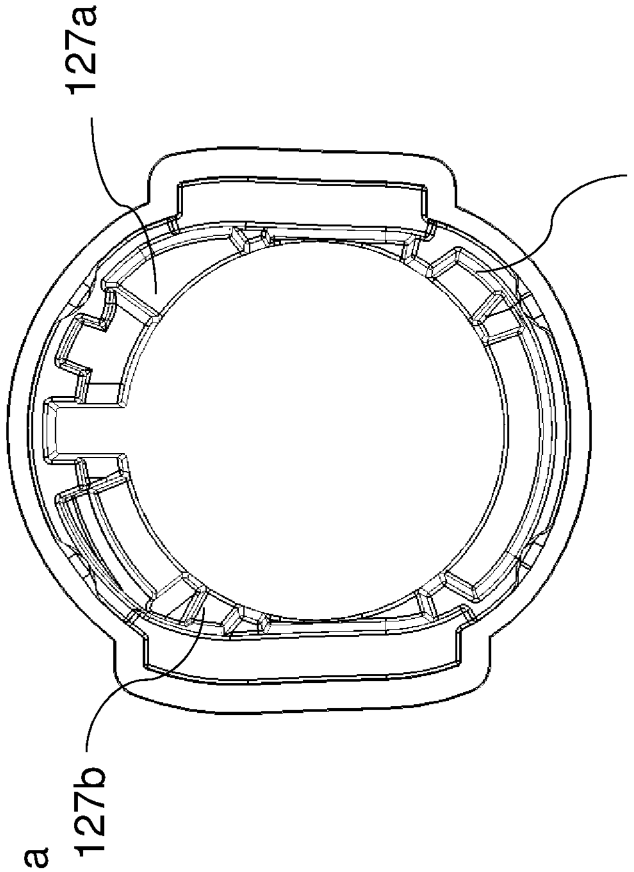
FIG. 39 is a rear perspective view of the housing shown in FIG. 40 with the sleeve removed, showing the ledges of the housing.
Figure 38:
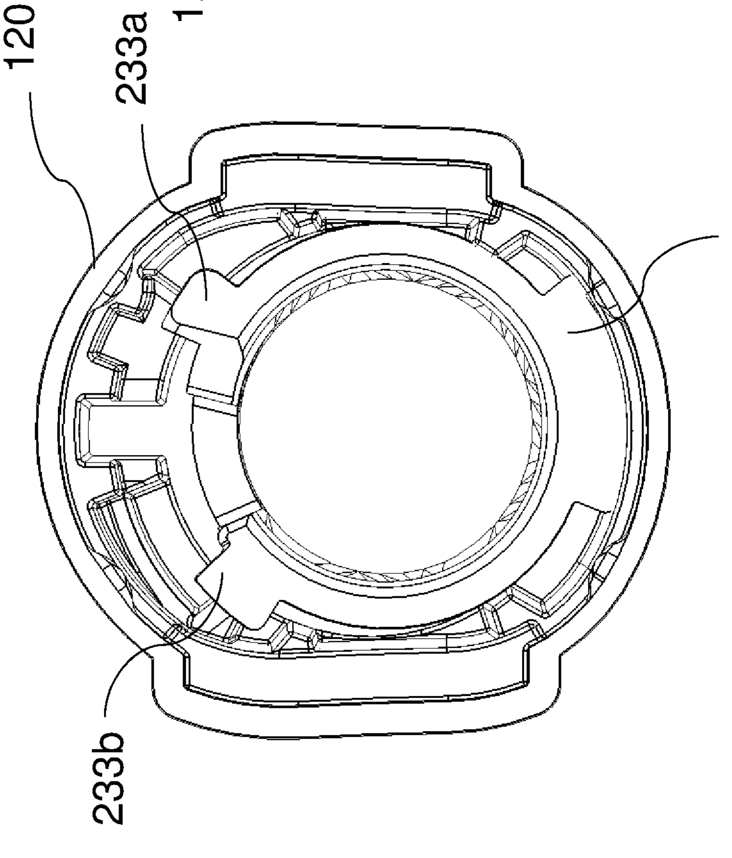
FIG. 38 illustrates a rear perspective view of the sleeve shown in the initial state of the device before use, with the protrusions of the sleeve resting upon ledges of the housing.
Figure 41:
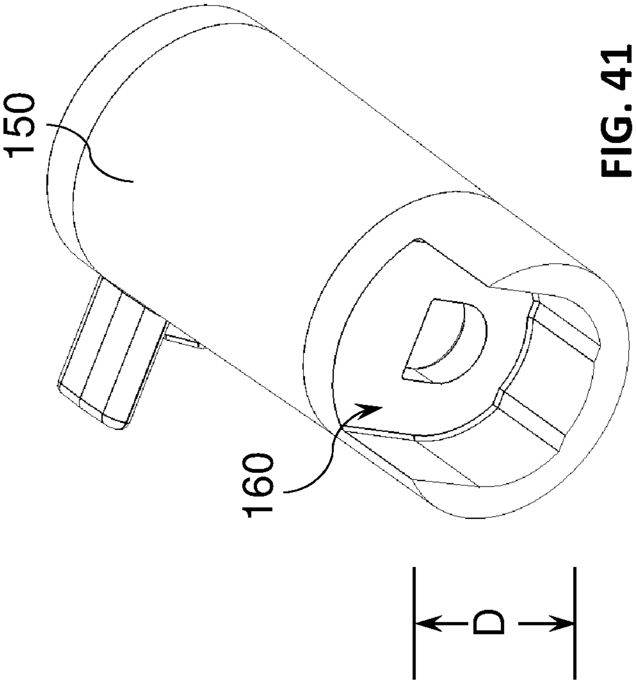
FIG. 41 is the front perspective view with a section taken along line A-A of FIG. 42, showing the pocket.
Figure 40:
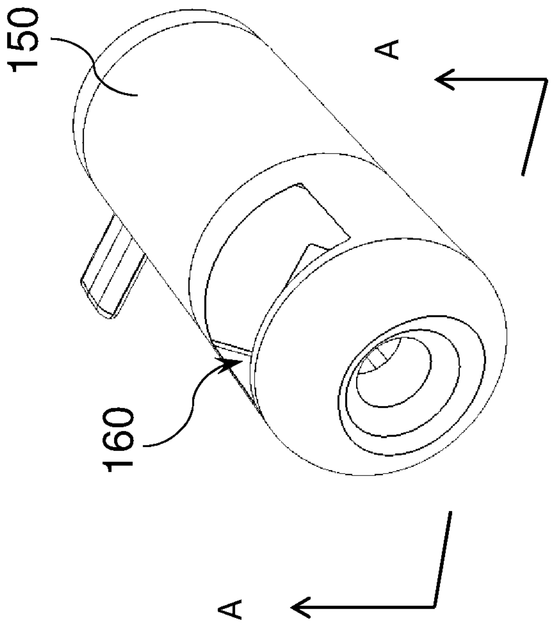
FIG. 40 is a front perspective view of the sleeve shown in FIG. 25, illustrating the pocket that holds the clip.
Figure 43:
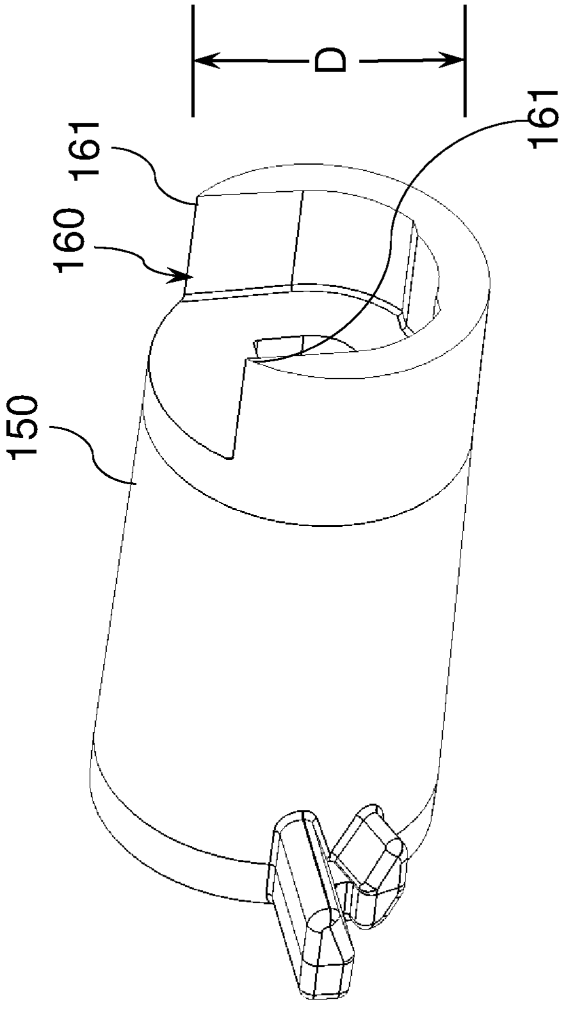
FIG. 43 is a front perspective view with a section taken along line A-A of FIG. 44, showing the pocket.
Figure 42:
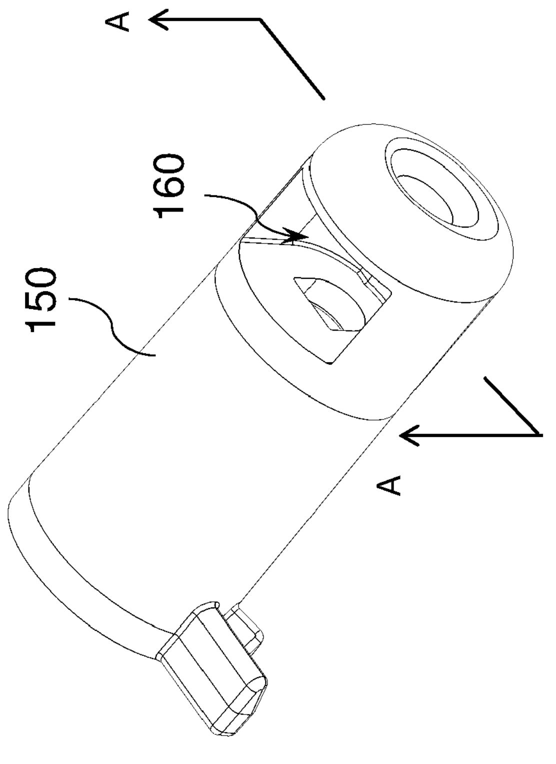
FIG. 42 is an alternate front perspective view of the sleeve shown in FIG. 25, illustrating the pocket that holds the clip.

Referring now to FIGS. 31-35, in some embodiments of the device 110, the housing 120 includes a first ledge 127*a* that cooperates with at least one radial protrusion on the activation component in the form of the tether 130 to maintain the activation component and the elongate sleeve 150 of the needle cannula cover 115 in the initial position. More details of the activation component in the form of the tether 130 can be seen in FIGS. 34-36, and the cooperation of the one or more ledges and the at least one radial protrusion on the activation component in the form of the tether 130.

When the elongate sleeve 150 of the needle cannula cover is moved from the initial position in a proximal direction, the activation component in the form of the tether 130 is rotated, causing the at least one radial protrusion to move off of the first ledge 127*a*, and causing the elongate sleeve 150 of the needle cannula cover 115 to be moved in a distal direction. This is considered activation of the device 110, because the sleeve 150 is no longer held in a fixed position with respect to the housing by the radial protrusion of the sleeve 150 resting on the ledge of the housing 120.

Figure 33:
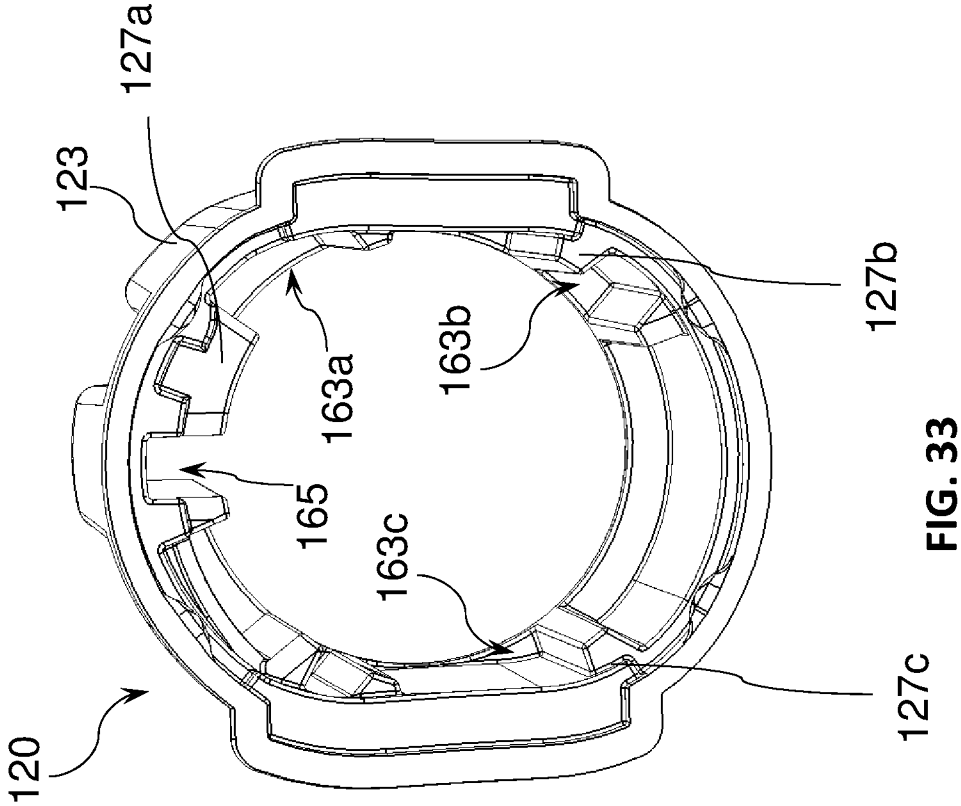
FIG. 33 illustrates a rear view of the housing of the device of FIG. 25.
Figure 32:
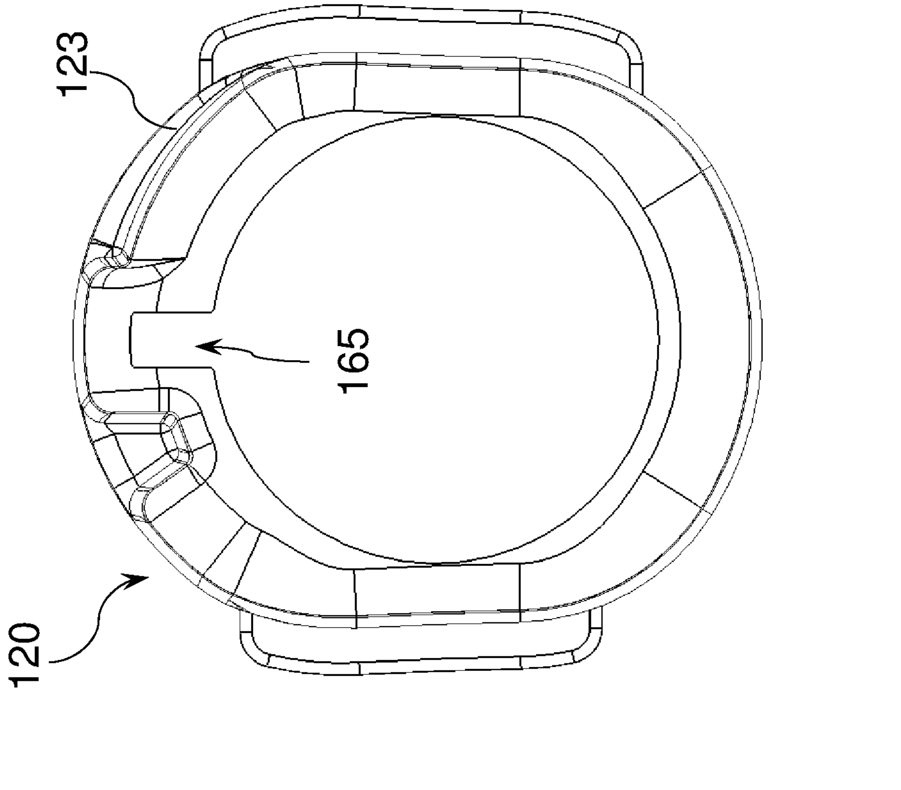
FIG. 32 illustrates a front view of the housing of the device of FIG. 25.
Figure 35:
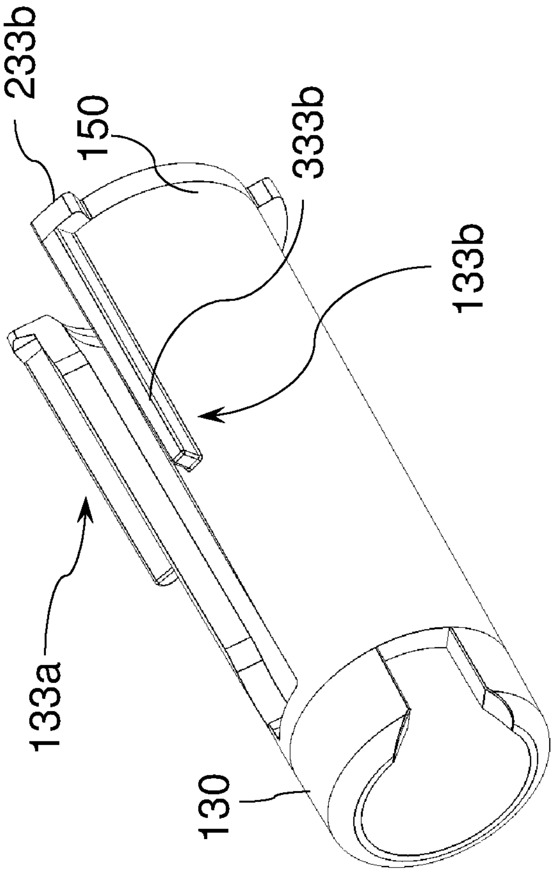
FIG. 35 illustrates an alternate front perspective view of the sleeve of the device of FIG. 25 rotated slightly counter-clockwise from the view in FIG. 36.
Figure 34:
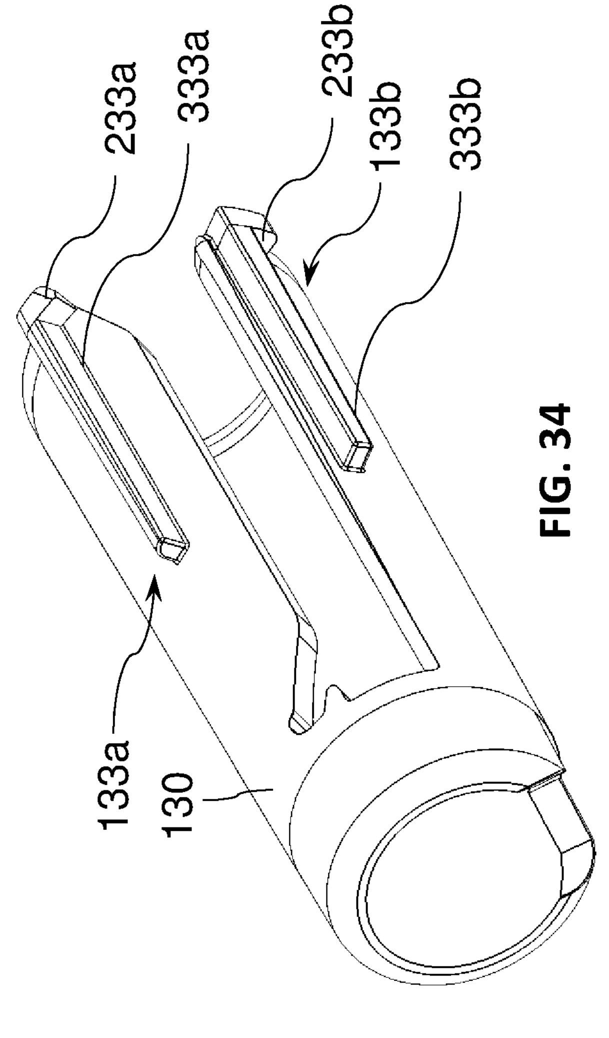
FIG. 34 illustrates a front perspective view of the sleeve of the device of FIG. 25.

As best seen in FIG. 33, the housing 120 of the device 110 may include a first ledge 127*a*, a second ledge 127*b*, and a third ledge 127*c* spaced apart from each other within the housing. The first ledge 127*a*, the second ledge 127*b* and the third ledge 127*c* are areas where the inner diameter of the housing 120 is reduced with inwardly protruding mass that forms the ledges. The disclosure of the three ledges is exemplary only, and the device according to one or more embodiments can include only a single ledge, two ledges, three ledges or more than three ledges. Adjacent to each ledge, there is a housing channel that runs along the length of the housing from the proximal end 121 to the distal end 122 of the housing 120. Thus, as best seen in FIG. 33, there is a first housing channel 163*a* adjacent the first ledge 127*a*, a second housing channel 163*b* adjacent the second ledge 127*b*, and a third housing channel 163*c* adjacent the third ledge 127*c*. The housing body 123 further includes a guide track 165 that functions as a guide track for a protrusion on the distal end of the elongate sleeve 150, which will be discussed further below.

Referring now to FIGS. 34-37, the at least one radial protrusion 133*a* comprises a first protrusion 152*a* in the form of a L-shaped radial protrusion, wherein a first portion 233*a* of the first radial protrusion 133*a* engages the first ledge 127*a* when the needle cannula cover is in the initial position and a second portion 333*a* of the first radial protrusion 133*a* being L-shaped slides within a first housing channel 163*a* on an inner surface of the housing 120, allowing the activation component to slide in a distal and proximal direction with respect to the housing.

Embodiments of the device 110 include a second radial protrusion 133*b* being L-shaped and having a first portion 233*b* which engages a second ledge 127*b* when the needle cannula cover is in the initial position and a second portion 333*b* which slides within a second housing channel 163*b* on an inner surface of the housing 120.

Embodiments further include a radial protrusion 133*c* being T-shaped and slidably movable in a third housing channel 163*c*, the radial protrusion 133*c* being T-shaped and having a first portion 233*c* that engages a third ledge 127*c* when the needle cannula cover is in the initial position, and a second portion 333*c* that slides within a third housing channel 163*c* on an inner surface of the housing 120. It will be understood that the radial protrusions 133*a*, 133*b* and 133*c* on the activation component in the form of the tether 130 can be configured in other ways. In general, there is at least one radial protrusion that has a surface that rests on a ledge of the housing in the initial state when the device 110 is not activated, the ledge being adjacent to a housing channel that guides the radial protrusion as the intermediate component in the form of the tether 130 slides within the housing. In an embodiment, there can be a single radial protrusion on that rests on a single ledge of the housing and a single channel. In an embodiment, there can be a pair of radial protrusions that rest on a pair of ledges adjacent to a pair of channels in the housing. In an embodiment, there can be three protrusions that rest on three ledges adjacent three channel in the housing. More ledges, protrusions and channels in the housing are within the scope of the disclosure. In one or more embodiments, the radial protrusions can be L-shaped, T-shaped or a combination of L-shaped and T-shaped. In one or more embodiments, the protrusions are neither L-shaped nor T-shaped, and instead only include a surface that rests upon the respective ledges.

Figure 44:
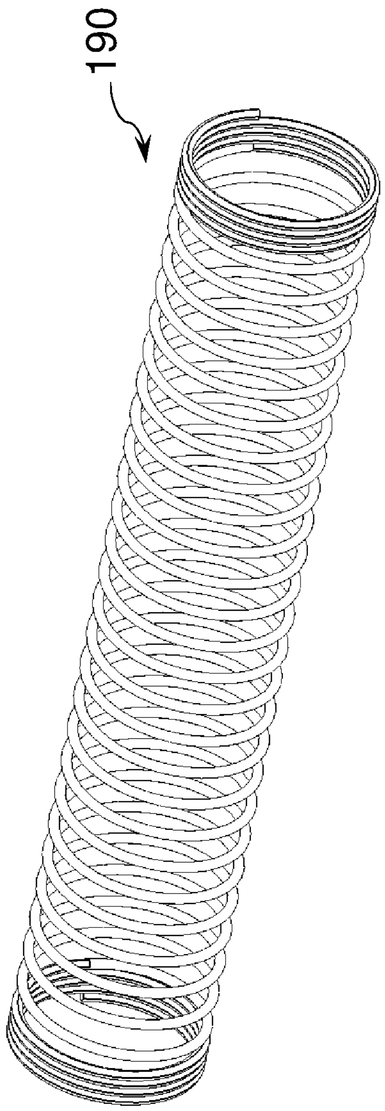
FIG. 44 is a perspective view of a biasing element of the device shown in FIG. 25.
Figure 45:
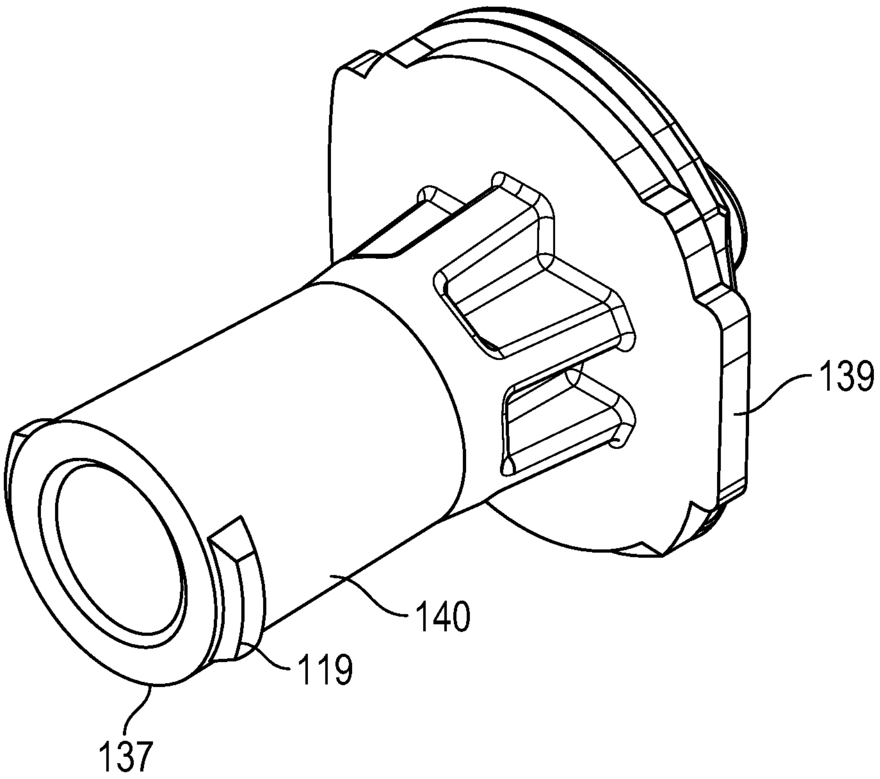
FIG. 45 is a rear perspective view of the hub of the device shown in FIG. 25.
Figure 46:
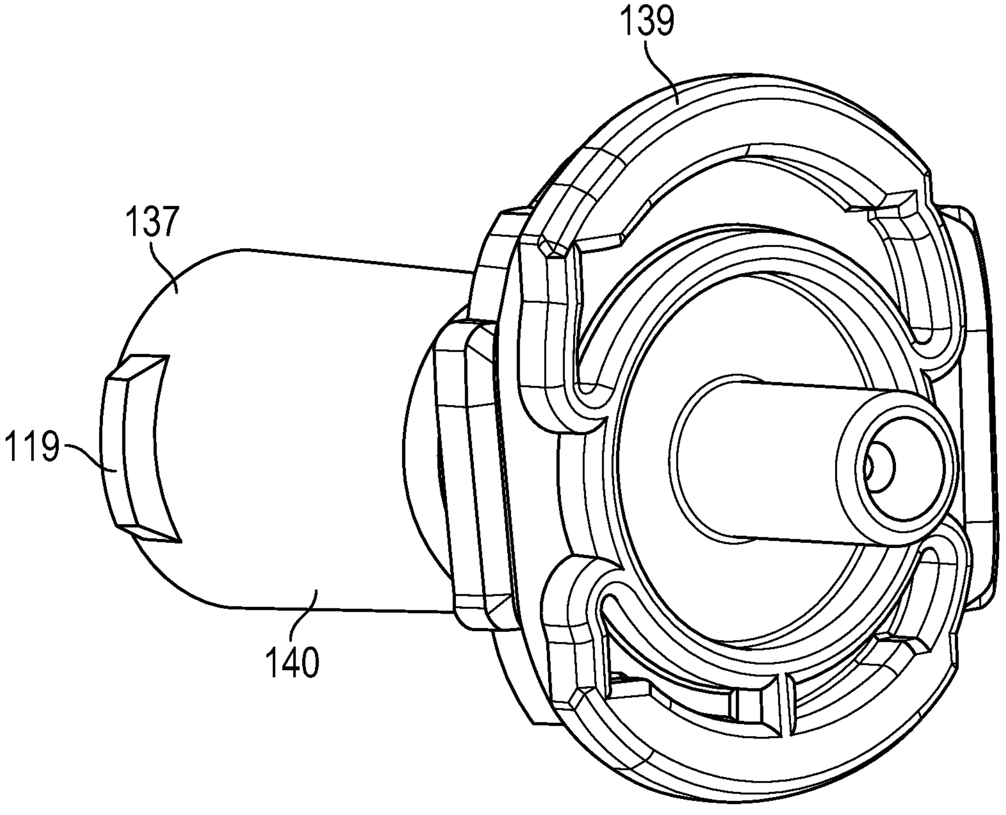
FIG. 46 is a front perspective view of the hub of the device shown in FIG. 25.

FIG. 44 shows a view of the biasing element in the form of a spring 190, which is mounted within the sleeve 150 and biases the sleeve in a distal direction when the device 110 is activated. FIGS. 45 and 46 show views of the hub 140.

The device according to one or more embodiments can include the needle cannula cover 115 elongate sleeve 150 having a second protrusion 152*b* that engages first guide path 131 in the form of a first slot on the activation component in the form of tether 130 to hold the elongate sleeve 150 of needle cannula cover 115 in the initial position. The device 110 can further include the elongate sleeve 150 of the needle cannula cover 115 further comprising a first protrusion 152*a* in the form of a protruding bar that moves within a second guide path 132 in the form of a track within the activation component in the form of the tether 130 and a guide track 165 within the housing. In one or more embodiments, the first protrusion 152*a* and the guide track 165 key the elongate sleeve 150 of the needle cannula cover and the housing 120, preventing rotational movement of the elongate sleeve 150 of the needle cannula cover 115.

Another embodiment of the disclosure pertains to a safety needle device 110, which in some embodiments is a single-use passive safety needle device. The device 110 according to this embodiment comprises a hub 140 having a proximal end that can be coupled to a syringe, the hub having a needle cannula 142 extending therefrom in a distal direction, the needle cannula having a longitudinal axis and distal tip 144. The device further includes a housing 120 having a proximal end, a distal end, and a housing body 123, the hub 140 being attached to the housing 120 and the needle cannula 142 and the distal tip 144 extending past the distal end of the housing. In this embodiment, the device includes activation component 195, which will be explained with respect to FIGS. 58-63, with specific reference to FIG. 62. In one or more embodiments, the activation component 195 can move axially in the direction of arrows 197 and radially in the direction of arrows 196 with respect to the housing, the activation component 195 telescopically engaged with the housing 120. In the embodiments shown and described herein, the activation component has been shown as a tether 130. As used herein, the word "tether" means an attachment to a device that anchors one component of the device movably to a reference point on the device. In one or more embodiments, the tether 30 or tether 130 described herein attaches to the housing 20 or housing 120 and anchors the movable sleeve 50 or sleeve 150 to the housing 20 or housing 120 which is a non-movable fixed reference point. Thus, in one or more embodiments, the tether 30 at least axially moves with respect to the housing 20 and anchors movable sleeve 50 to the housing 20, and in other embodiments, the tether 30 axially and rotationally (or radially) moves with respect to the housing 20 and anchors movable sleeve 50 to the housing 20. In one or more embodiments, the tether 130 at least axially moves with respect to the housing 120 and anchors movable sleeve 150 to the housing 120, and in other embodiments, the tether 130 axially and rotationally (or radially) moves with respect to the housing 120 and anchors movable sleeve 150 to the housing 120. This embodiment also includes a sleeve 150 of a needle cannula cover 115 that can move axially (as shown by arrow 197) with respect to the housing and the activation component 195. The sleeve 150 of the needle cannula cover 115 is telescopically engaged with the activation component 195, and the sleeve 150 of the needle cannula cover includes a second protrusion 152*b* protruding radially from the sleeve 150, which may be a peg engaged in a first guide path 31 shown as a slot in the activation component 195 to activate the sleeve 150 of the needle cannula cover. This causes the sleeve 150 of the needle cannula cover to be moved in a distal direction.

Figure 61:
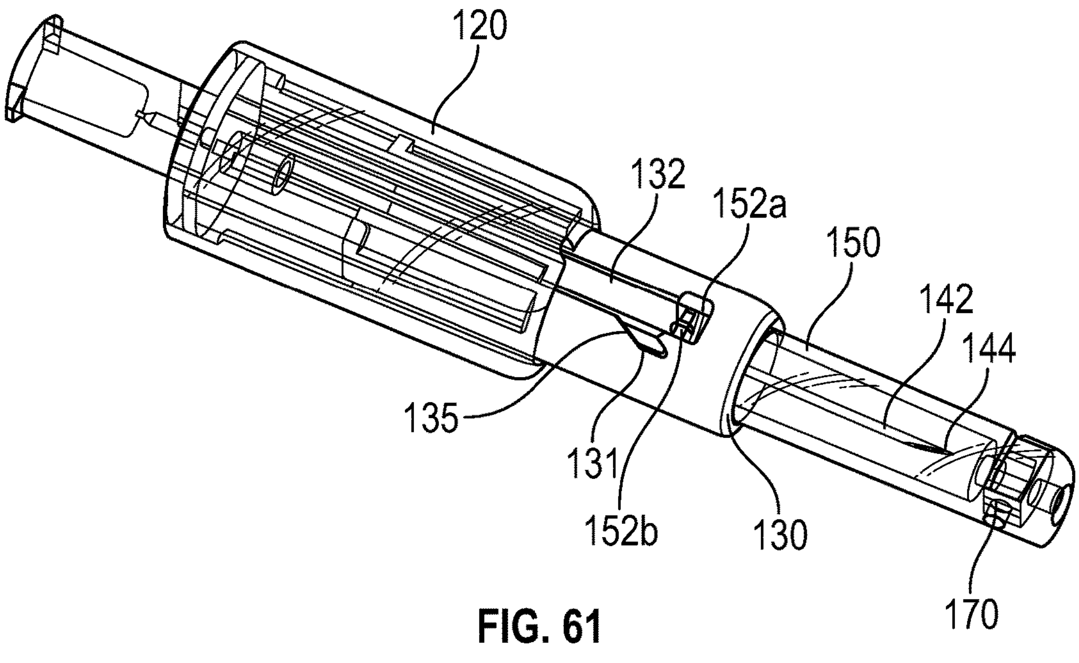
FIG. 61 shows a front perspective view of the device shown in FIG. 60 with the sleeve fully extended and covering the distal tip of the needle cannula.
Figure 62:
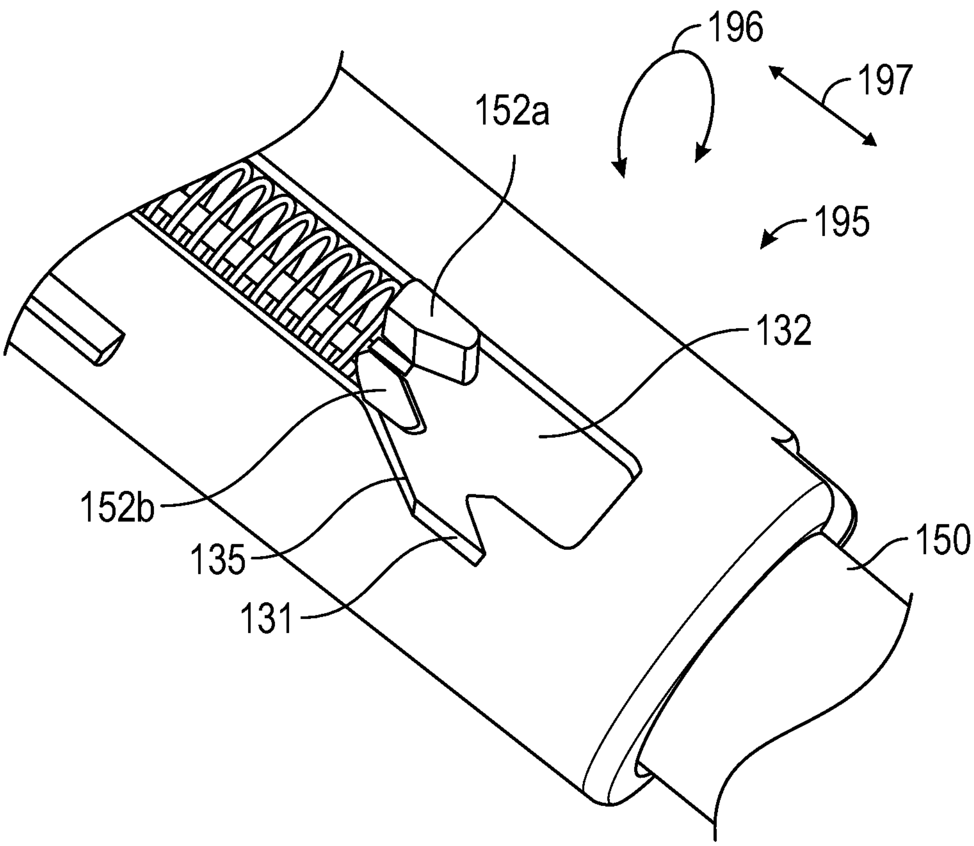
FIG. 62 shows a partial perspective view showing the activation feature of the device shown in FIG. 25.
Figure 63:
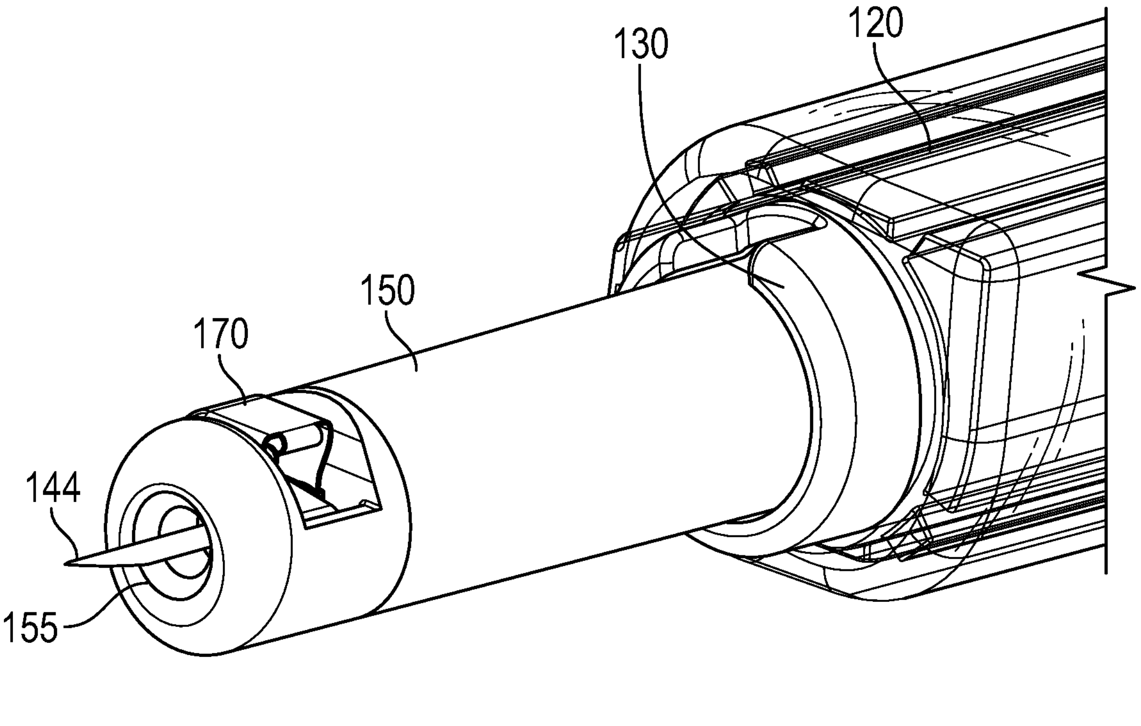
FIG. 63 shows a partial perspective view showing the needle exposed from the distal end of the sleeve and the clip in the pocket.
Figure 64:
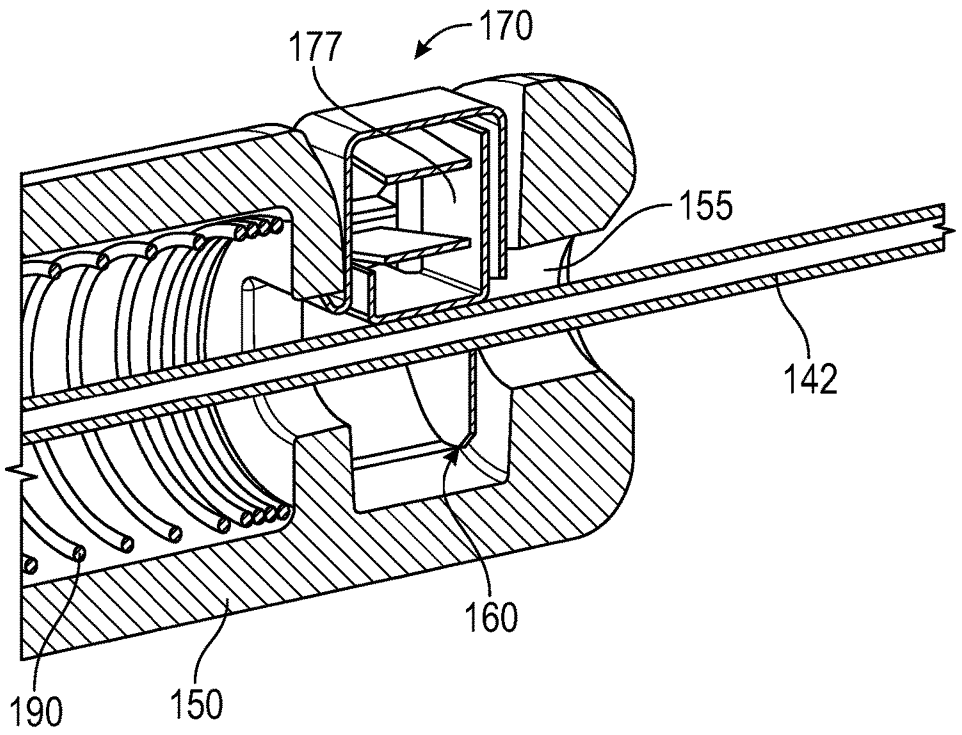
FIG. 64 is a partial sectional view of the device of FIG. 25 showing the clip of biased against the needle cannula and the gate held in the open position.
Figure 65:
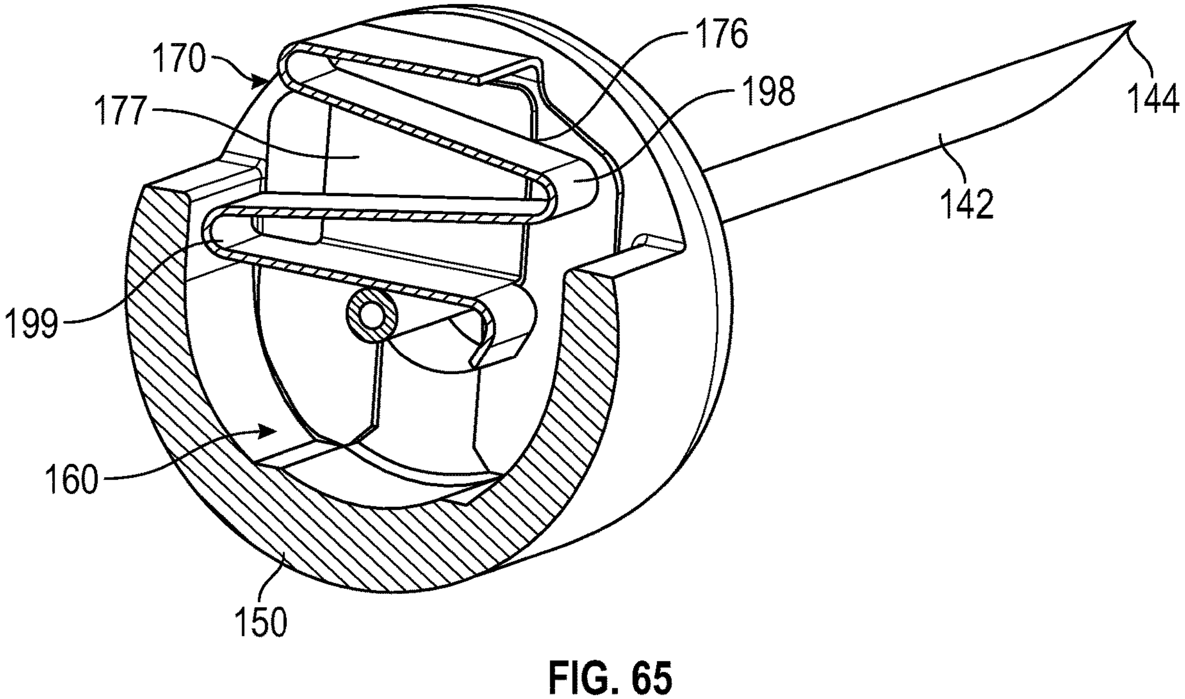
FIG. 65 is a view of an alternate embodiment of a clip that can be used with the device of FIG. 25, showing the needle cannula holding the gate open.
Figure 66:
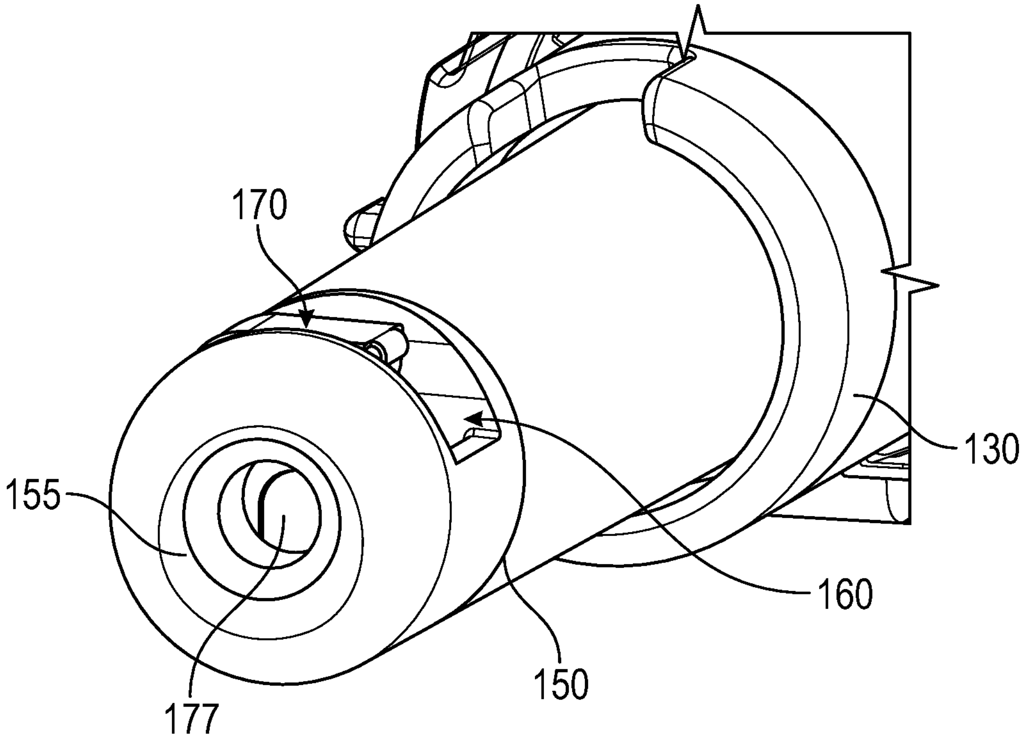
FIG. 66 is a partial perspective view of the distal end of the device of FIG. 25 with the needle cannula covered by the sleeve and the gate of the clip blocking the opening at the distal end of the sleeve.
Figure 67:
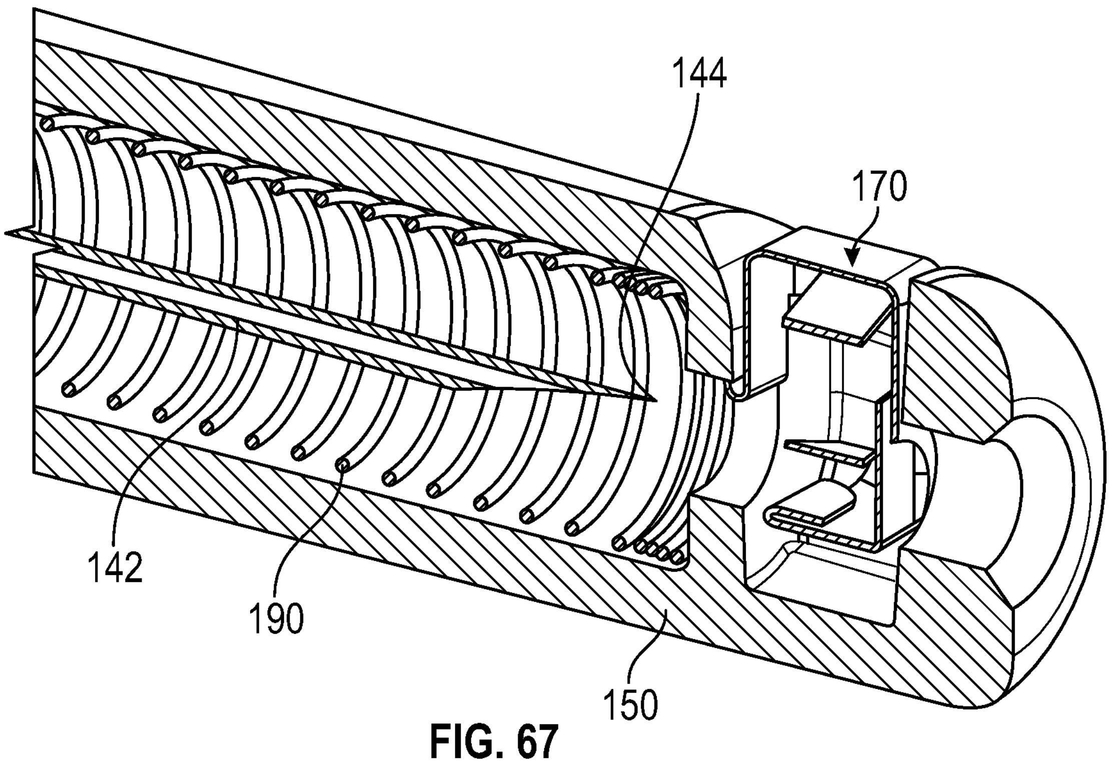
FIG. 67 is a partial sectional view of the device shown in FIG. 66, showing the needle cannula retracted in the sleeve and blocked from exiting the sleeve by the gate of the clip.

In a variant of this embodiment, as shown in FIG. 61, there is a clip 170 mounted in the sleeve 150 of the needle cannula cover adjacent an opening 155 in a distal end in the needle cannula cover, the clip preventing the distal tip 144 of the needle cannula 142 from exiting the opening 155 when the sleeve 150 needle cannula cover is in a fully extended position. In another variant on this embodiment, a first protrusion 152*a* protruding outwardly in the form of a bar extending from the sleeve 150 of the needle cannula cover cooperates a second guide path 132 in the form of a slot in the activation component 195 guides the sleeve 150 of the needle cannula cover when the needle cannula cover slides within the housing 120. As seen in FIG. 62, the first guide path 131 and the second guide path 132 form a Y-shaped slot at the distal end of the activation component 195. In a further variant the interior surface of the housing further including a guide track 165 that keys with a first protrusion 152*a* in the form of a protruding bar on the sleeve 150 of the needle cannula cover, preventing rotational movement of the sleeve 150 of the needle cannula cover with respect to the housing 120.

Another embodiment of the disclosure pertains to a safety needle device comprising a hub 140 having a proximal end that can be coupled to a syringe and a distal end supporting a needle cannula 142 having a longitudinal axis and distal tip 144 extending from the hub 140. The device further includes a housing 120 having a proximal end, a distal end, and a housing body 123, the hub 140 being attached to the housing 120 adjacent the proximal end and the needle cannula 142 and the distal tip 144 extending past the distal end of the housing 120. The device 110 further includes a needle cannula cover comprising an elongate sleeve 150 having a distal end 154 having an opening 155 therein, the sleeve axially movable in a distal and proximal direction inside the housing 120 and being biased to move in a distal direction to cover the distal tip 144 of the needle cannula 142, the opening 155 allowing the distal tip 144 to pass therethrough when sleeve 150 is moved in a proximal direction. This embodiment further comprises a biased clip 170 disposed adjacent the distal end 154 of the elongate sleeve 150, the biased clip 170 having a gate 177 that is biased by a biasing element 176 to a closed position to cover the opening 155 when the cover is moved in a proximal direction and the distal tip 144 of the needle cannula passes through the opening 155, the gate 177 held in an open position by the needle cannula 142. The features of the biased clip 170 are best seen in FIGS. 63-67, showing the biased clip 170 in the pocket of the sleeve 150.

In a variant on this embodiment the biasing element 176 of the biased clip comprises at least two bends, a first bend 198 and a second bend 199 that provide biasing force to the gate 177, the needle cannula 142 in sliding contact with a portion of the biased clip 170. In some embodiments the biased clip 170 comprises three bends. In some embodiments, the biased clip 170 is mounted in a pocket adjacent the distal end of the sleeve 150 needle cannula cover.

Figure 58:
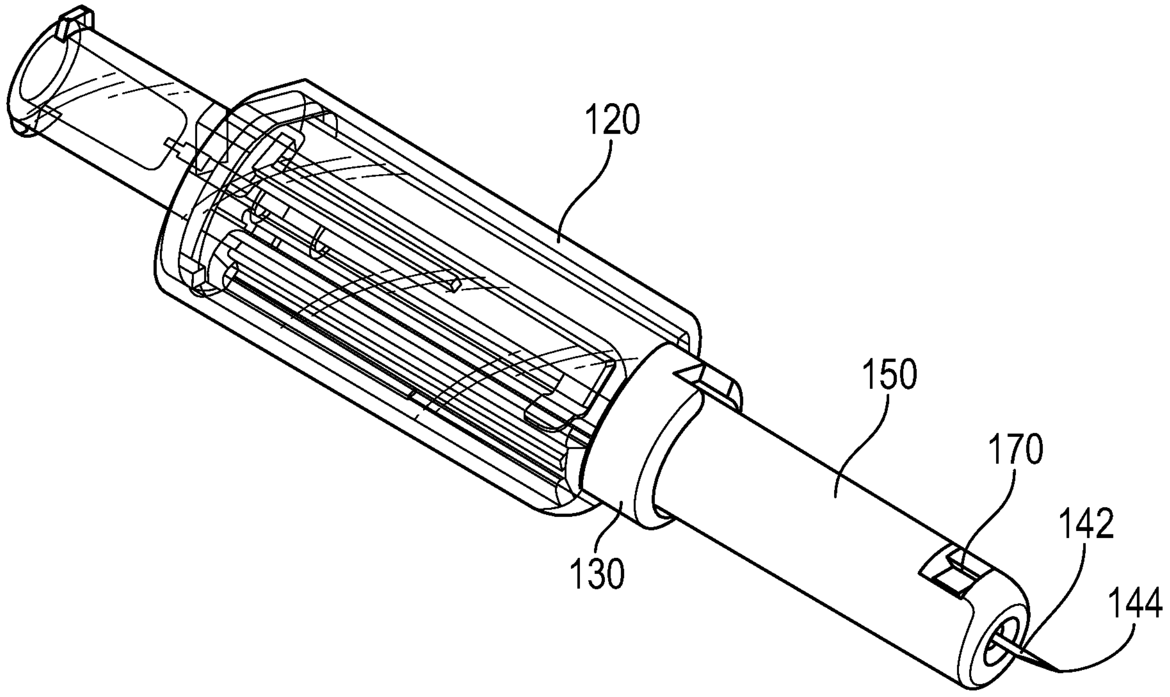
FIG. 58 shows a front perspective view of the device shown in FIG. 25 in the initial state with the distal tip of the needle cannula exposed through the sleeve.
Figure 59:
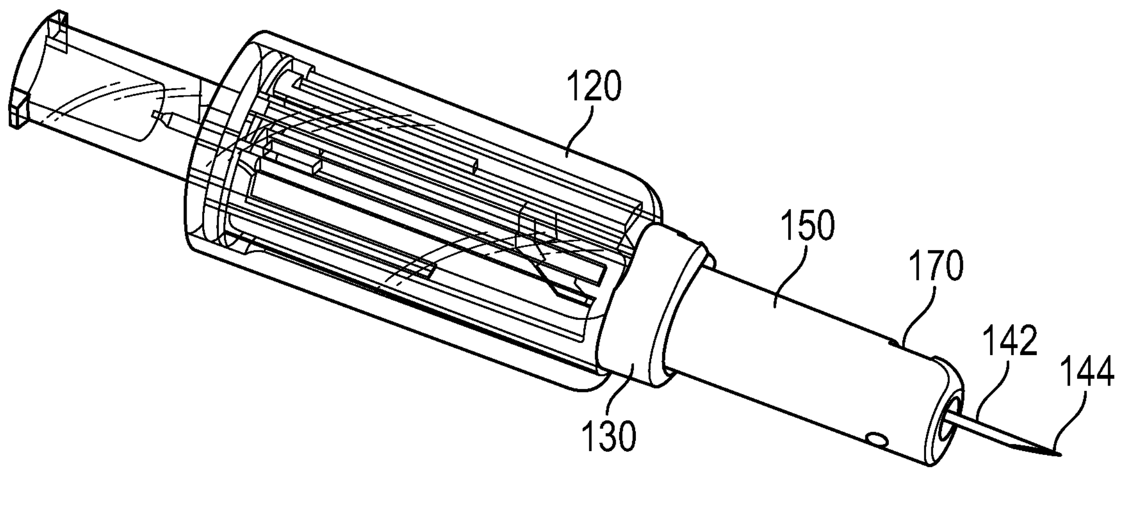
FIG. 59 shows a front perspective view of the device shown in FIG. 60 with the sleeve partially retracted.
Figure 60:
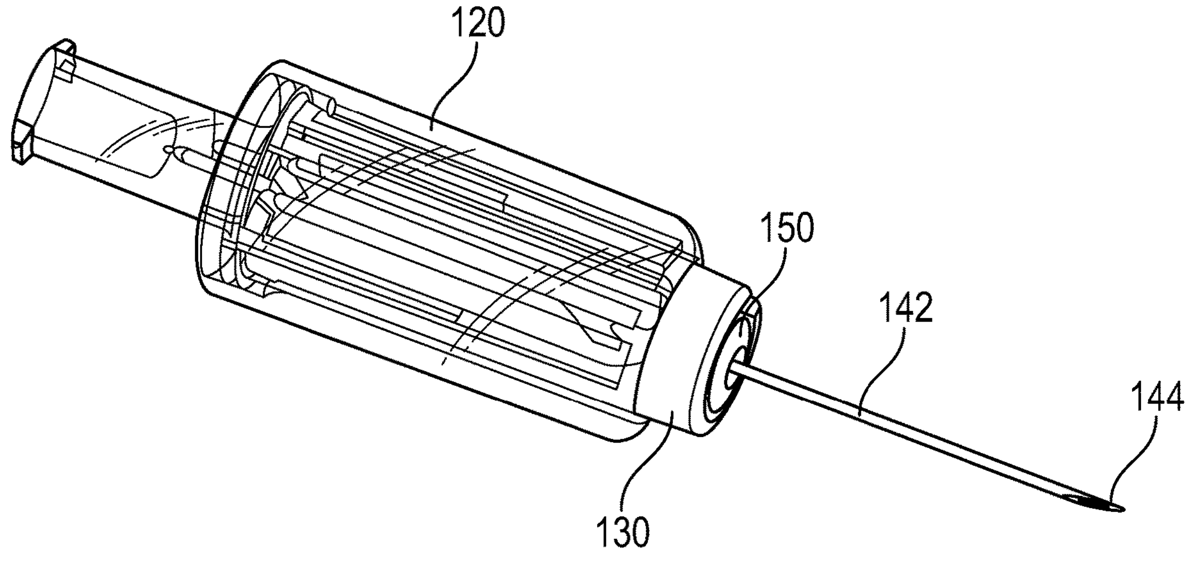
FIG. 60 shows a front perspective view of the device shown in FIG. 60 with the sleeve fully retracted.

In variants on this embodiment in which the safety needle is a single-use passive safety needle, as best shown in FIGS. 58-61 the sleeve of the needle cannula cover has an initial position shown in FIG. 58, where the distal tip 144 of the needle cannula 142 is exposed and the elongate sleeve 150 cannot move in a distal direction. Referring to FIG. 59, there is an intermediate position where the sleeve 150 of the needle cover is moved proximally such that the distal end 154 of the elongate sleeve 150 is moved further from the distal tip 144 of the needle cannula and the elongate sleeve 150 is now biased to move in a distal direction because the device has been activated, as discussed above with respect to FIGS. 32-39, where a radial protrusion on the tether 130 is moved from a ledge on the housing to activate the device. FIG. 60 shows the sleeve 150 fully retracted and the needle cannula fully exposed. FIG. 61 shows a final position where the distal end 154 of the elongate sleeve 150 extends past the distal tip 144 of the needle cannula 142 and the gate 177 of the biased clip 170 prevents proximal movement of the elongate sleeve 150 and exposure of the needle cannula distal tip 144. As will be understood, the initial position of the device is a position when the device is removed from a package by a practitioner. The distal tip of the needle cannula is inserted into a patient, and as the needle cannula is advanced into a patient, the sleeve moves proximally away from the distal tip from the skin of the patient pushing on the distal end of the sleeve, which advances proximally into the housing 120 as shown in FIG. 60. When the practitioner withdraws the needle cannula 142 from the patient, the spring element biases the sleeve 150 in a distal direction and when the needle cannula 142 is removed from the patient, the distal end of the sleeve advances past the distal tip 144 of the needle cannula 142, blocking the needle cannula from exiting the sleeve 150. In one or more specific embodiments, the activation feature discussed above with respect to FIG. 62 can be incorporated with the tether 130, as shown in FIG. 61. In one or more embodiments, the safety device is activated after the initial state by advancing the sleeve in a proximal direction, causing the second protrusion 152*b* to move from the first guide path 131 which forms a Y-shaped slot with the second guide path 132, causing the tether 130 to rotate counterclockwise with respect to the housing 120. The first guide path 131 is hook-shaped to prevent the tether 130 from rotating prior to proximal movement of the sleeve. As the second protrusion 152*b* advances, it rides along ramping surface 135 and is guided into the second guide path 132. During movement in the second guide path 132, the sleeve 150 only moves axially, but does not rotate or move radially. As the sleeve 150 is further moved in a proximal direction, the first protrusion 152*a* on the sleeve slides along the second guide path axially.

Thus, the tether 130 is an intermediate component to the housing 120 and the sleeve 150 that moves axially and radially within the housing 120 and the sleeve 150 of the needle cannula cover moves axially within the intermediate component and the housing. The sleeve 150 of the needle cannula cover cooperates with the intermediate component to activate the device after movement from the initial position, causing the sleeve to be biased the in the distal direction.

As the user of the device 110 removes the device from the patient the spring 190 that biases the sleeve in a distal direction automatically extends the sleeve 150 to the first protrusion 152*a* slides along the guide track 165 in the housing 120 and exits the guide track 165. The ledges in the housing that hold the tether by the protrusion from the tether 130 are not engaged after the device has been activated, and the spring 190 also automatically extends the tether 130 allowing the tether to fully extend until the protrusions are stopped at the distal end of the housing. As the tether 130 fully extends, the needle cannula distal tip 144 is enveloped or covered by the distal end of the sleeve 150. The biased clip 170 closes the gate 177, automatically locking the device.

Figure 47:
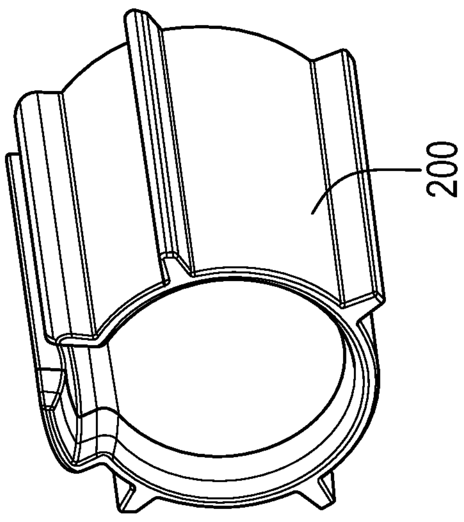
FIG. 47 is a perspective view of a spacer element of the device shown in FIG. 25.
Figure 48:
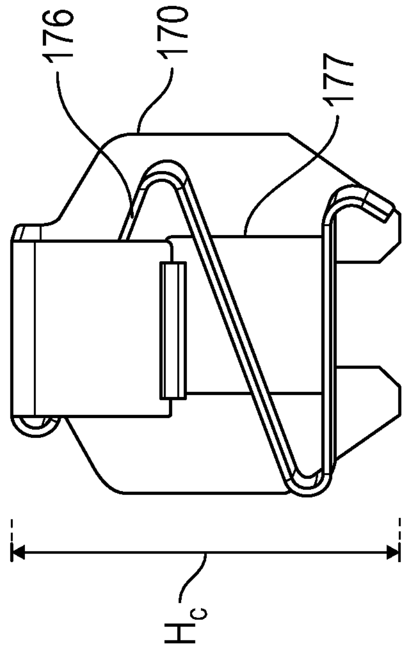
FIG. 48 is a rear view of a clip of the device shown in FIG. 25.
Figure 49:
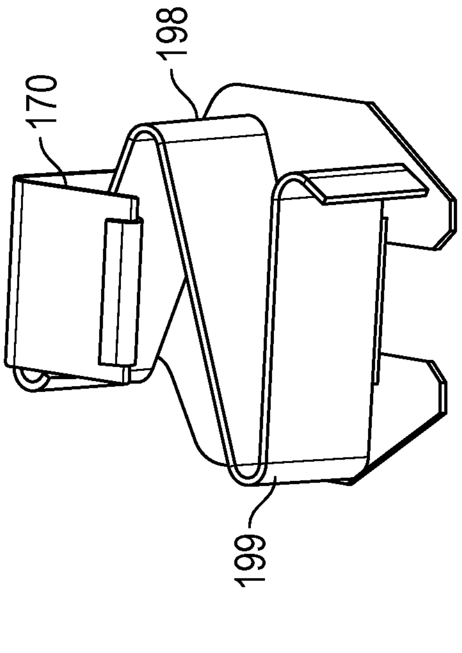
FIG. 49 is a rear perspective view of the clip shown in FIG. 50.
Figure 50:
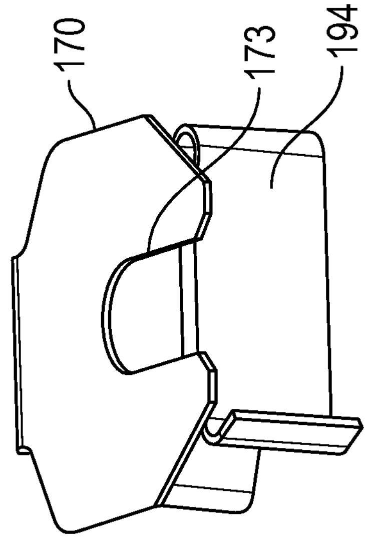
FIG. 50 is a front perspective view of the clip shown in FIG. 50.
Figure 53:
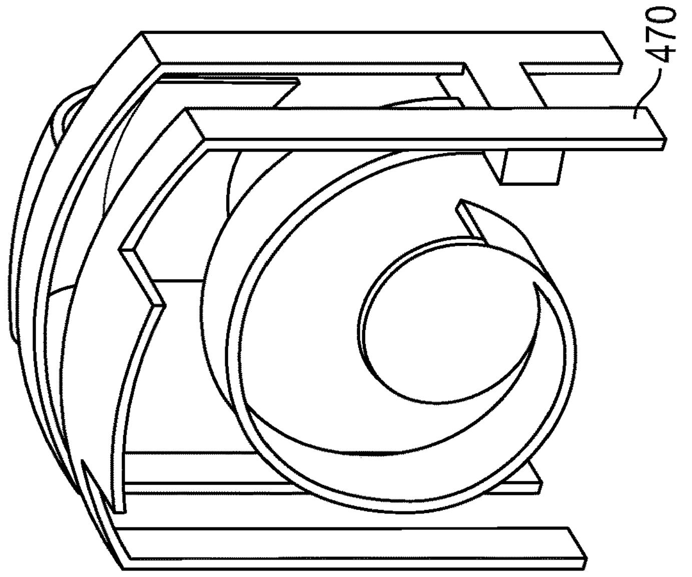
FIGS. 51-55 show alternate embodiments clips.
Figure 52:
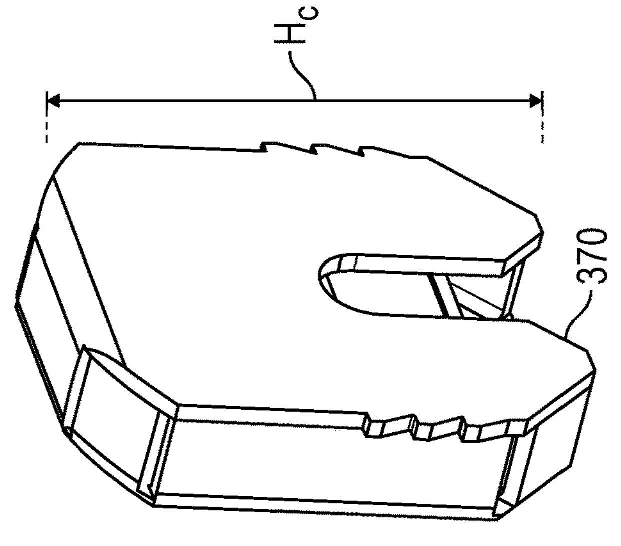
Figure 51:
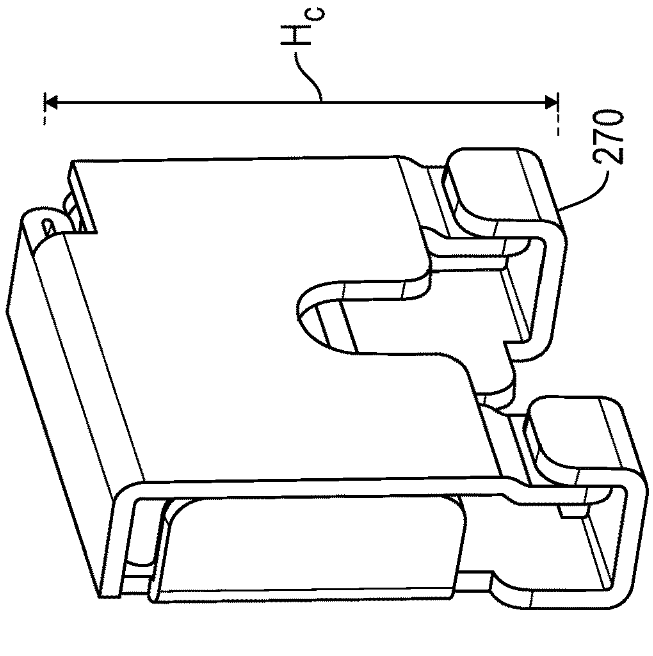
Figure 54:
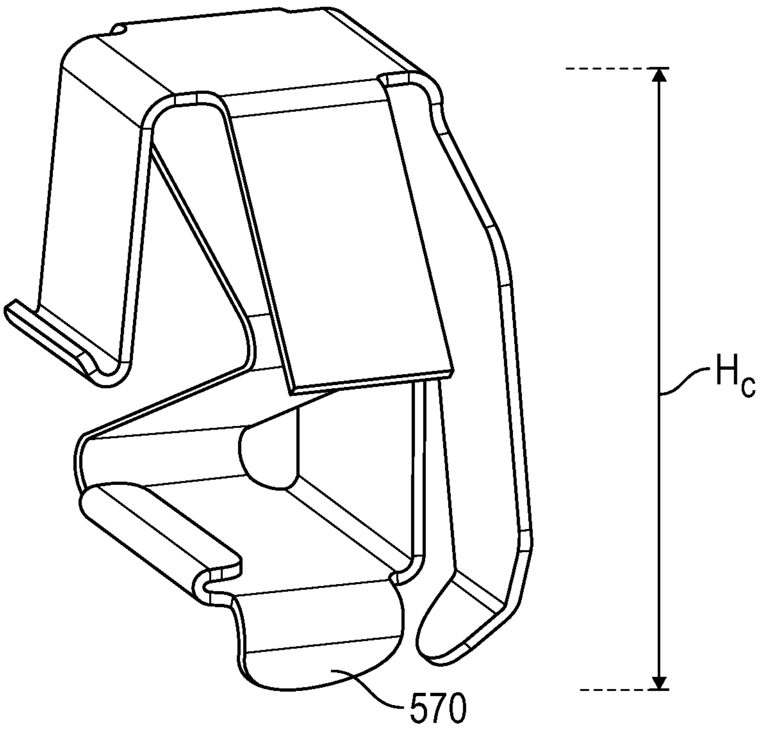
Figure 55:
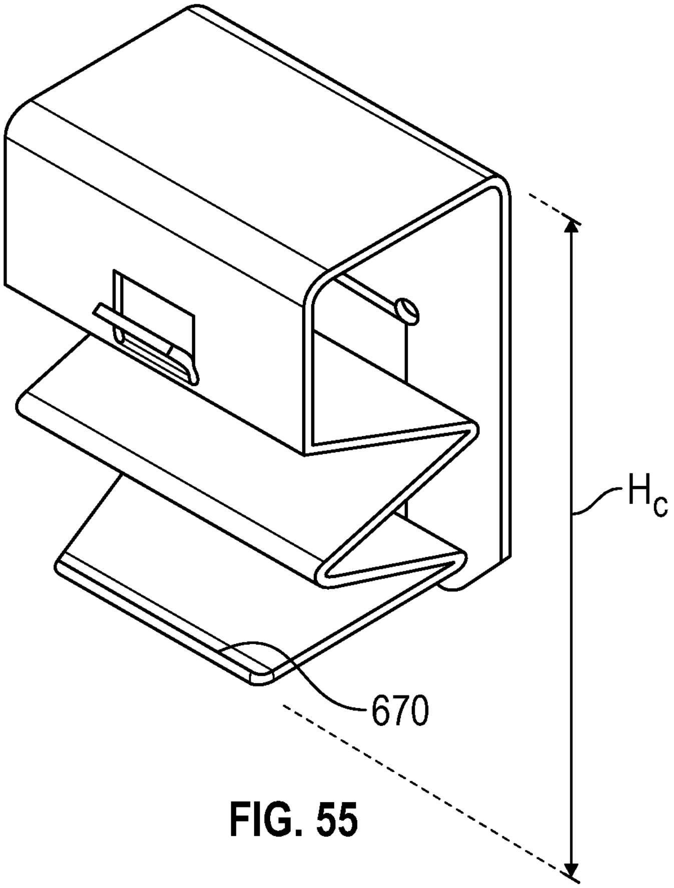

FIG. 47 shows a spacer 200 that can be mounted in the distal end of the housing for devices that are longer than 1" in length. FIGS. 48-50 show different views of the biased clip discussed above. The clip shown has a first bend 198 and a second bend 199 to provide an N-shaped biasing element 176. In some embodiments, there is a single bend to provide a V-shaped biasing element. In other embodiments, there are three or more bends. The biased clip 170 includes a slot 173 and a sliding surface 194, and the needle cannula 142 slides in the slot 173 and contacts the sliding surface 194 when the sleeve moves in a distal and proximal direction as described above. FIG. 51 shows an alternate embodiment of a biased clip 270 having full boxed in sides, which protects the biased clip 270 from debris in use and damage during assembly. FIG. 52 shows another alternate embodiment of a biased clip 370 in a fully boxed design having bite cleats on the ends. FIG. 53 shows another alternate embodiment of a biased clip 470 having a spiral bias design. FIG. 54 shows another alternate embodiment of a biased clip 570, and FIG. 55 shows another alternate embodiment of a biased clip 670 having three bends. Each of the alternate biased clip designs can be used in the devices disclosed herein.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A safety needle device comprising:

a hub having a proximal end that can be coupled to a syringe, the hub having a needle cannula extending therefrom in a distal direction, the needle cannula having a longitudinal axis and a distal tip;

a housing having a proximal end, a distal end, and a housing body, the hub being attached to the housing and the distal tip extending past the distal end of the housing;

a needle cannula cover comprising an elongate sleeve having a distal end, the needle cannula cover slidably moveable in the distal direction and a proximal direction inside the housing and being biased to move in the distal direction toward the distal tip of the needle cannula, the needle cannula cover having an initial starting position at which the distal tip of the needle cannula is exposed, an intermediate position at which the needle cannula cover is moved in the proximal direction to move the distal end of the needle cannula cover a distance further from the distal tip of the needle cannula, and an extended position at which the distal end of the needle cannula cover extends past the distal tip of the needle cannula to cover the distal tip; and a clip disposed adjacent the distal end of the needle cannula cover, the clip preventing proximal movement of the sleeve and exposure of the distal tip of the needle cannula when the clip is closed by a biasing element which biases a gate in a closed position, the biasing element comprising at least two bends that provide biasing force to the gate, the needle cannula in sliding contact with a portion of the clip, wherein a spring-biased blocking element is biased in a direction transverse to the longitudinal axis of the needle cannula and the spring-biased blocking element comprises the gate that is biased to move to the closed position to block an opening in the needle cannula cover and the spring-biased blocking element is held open by the needle cannula when the needle cannula cover is in the initial position and the intermediate position.

2. The safety needle device of claim 1, the needle cannula having a length, and the clip being slidably engageable along the length of the needle cannula.

3. The safety needle device of claim 1, wherein the clip slides over the distal tip of the needle cannula when the needle cannula cover is in the extended position, blocking the distal tip of the needle cannula and preventing the distal tip of the needle cannula from protruding through the opening.

4. The safety needle device of claim 3, wherein the clip blocks movement of the needle cannula through the opening in the needle cannula cover.

5. The safety needle device of claim 1, wherein the clip blocks the opening to prevent the distal tip of the needle cannula from protruding through the opening when the needle cannula cover is in the extended position.

6. The safety needle device of claim 5, further comprising a pocket adjacent the distal end of the sleeve configured to securely hold the clip in the pocket.

7. The safety needle device of claim 6, wherein the clip has a height and the pocket has a depth that is at least equal to the height of the clip.

8. The safety needle device of claim 1, wherein the safety needle device is a single-use passive safety needle device, wherein the needle cannula cover automatically covers the distal tip of the needle cannula after a patient has been injected and the needle has been removed from the patient.

9. The safety needle device of claim 8, wherein a practitioner or user of the safety needle device does not have to activate the needle cannula cover by pressing a button on the safety needle device or twisting the safety needle device.

10. A safety needle device comprising:

a hub having a proximal end that can be coupled to a syringe, the hub having a needle cannula extending therefrom in a distal direction, the needle cannula having a longitudinal axis and a distal tip;

a housing having a proximal end, a distal end, and a housing body, the hub being attached to the housing and the needle cannula and the distal tip extending past the distal end of the housing;

a needle cannula cover comprising an elongate sleeve having a distal end, the needle cannula cover slidably moveable in the distal direction and a proximal direction inside the housing and being biased to move in the distal direction toward the distal tip of the needle cannula, the needle cannula cover having an initial position at which the distal tip of the needle cannula is exposed, an intermediate position at which the needle cannula cover is moved in the proximal direction to move the distal end of the needle cannula cover a distance further from the distal tip of the needle cannula, and an extended position at which the distal end of the needle cannula cover extends past the distal tip of the needle cannula, the elongate sleeve axially moveable with respect to the needle cannula;

an activation component slidably engaged with the needle cannula cover and positioned intermediate the housing and the needle cannula cover, the activation component being rotationally moveable with respect to the housing, such that when the activation component is moved rotationally when the needle cannula cover is moved in the proximal direction from the initial position, the needle cannula cover is activated and biased to move in the distal direction; and a clip disposed adjacent the distal end of the needle cannula cover, the clip preventing the proximal movement of the elongate sleeve and exposure of the distal tip of the needle cannula, the clip comprising a latch having at least two bends, and the clip biased by the two bends to slide over and to cover the distal tip of the needle cannula with a spring-biased blocking element to block movement of the needle cannula through an opening in the needle cannula cover wherein the spring-biased blocking element is biased in a direction transverse to the longitudinal axis of the needle cannula and the spring-biased blocking element comprises the gate that is biased to move to the closed position to block the opening in the needle cannula cover and the spring-biased blocking element is held open by the needle cannula when the needle cannula cover is in the initial position and the intermediate position.

11. The safety needle device of claim 10, wherein the activation component and the needle cannula cover move telescopically within the housing such that the distal tip of the needle cannula is exposed when the activation component and the needle cannula cover are moved in the proximal direction from the initial position to the intermediate position, and the distal tip of the needle cannula is covered when the activation component and the needle cannula cover are moved in the distal direction to the extended position such that the distal end of the needle cannula cover is moved distally past the needle cannula tip.

12. The safety needle device of claim 10, wherein the housing includes a first ledge that cooperates with at least one radial protrusion on the activation component to maintain the activation component and the needle cannula cover in the initial position.

13. The safety needle device of claim 12, wherein when the needle cannula cover is moved from the initial position in the proximal direction, the activation component is rotated, causing the at least one radial protrusion to move off of the first ledge, and causing the needle cannula cover to be moved in the distal direction.

14. The safety needle device of claim 13, wherein the at least one radial protrusion comprises a first L-shaped radial protrusion, wherein a first portion of the first L-shaped radial protrusion engages the first ledge when the needle cannula cover is in the initial position and a second portion of the first L-shaped radial protrusion slides within a first housing channel on an inner surface of the housing, allowing the activation component to slide in the distal direction and the proximal direction with respect to the housing.

15. The safety needle device of claim 14, further comprising a second L-shaped radial protrusion having a first portion which engages a second ledge when the needle cannula cover is in the initial position and a second portion which slides within a second housing channel on the inner surface of the housing.

16. The safety needle device of claim 15, further comprising a T-shaped radial protrusion slidably moveable in a third channel, the T-shaped radial protrusion having a first portion that engages a third ledge when the needle cannula cover is in the initial position.

17. The safety needle device of claim 13, the needle cannula cover comprising a protruding peg that engages a slot on the activation component to hold the needle cannula cover in the initial position.

18. The safety needle device of claim 17, the needle cannula cover further comprising a protruding bar that moves within a guide track within the activation component and a track within the housing.

19. The safety needle device of claim 18, wherein the protruding bar and the guide track are keyed to the needle cannula cover and the housing, preventing rotational movement of the needle cannula cover.

20. The safety needle device of claim 19, wherein the safety needle device is a single-use passive safety needle device, wherein the needle cannula cover automatically covers the distal tip of the needle cannula after a patient has been injected and the needle cannula has been removed from the patient.

21. The safety needle device of claim 20, wherein a practitioner or user of the safety needle device does not have to activate the needle cannula cover by pressing a button on the safety needle device or twisting the safety needle device.

22. A safety needle device comprising:

a hub having a proximal end that can be coupled to a syringe, the hub having a needle cannula extending therefrom in a distal direction, the needle cannula having a longitudinal axis and a distal tip;

a housing having a proximal end, a distal end, and a housing body, the hub being attached to the housing and the needle cannula and the distal tip extending past the distal end of the housing;

an activation component that can move axially and radially with respect to the housing, the activation component telescopically engaged with the housing;

a needle cannula cover that can move axially with respect to the housing and the activation component, the needle cannula cover telescopically engaged with the activation component, the needle cannula cover comprising a peg engaged in a slot in the activation component to activate the needle cannula cover, causing the needle cannula cover to be moved in the distal direction; and a clip disposed adjacent the distal end of the needle cannula cover, the clip preventing proximal movement of the needle cannula cover and exposure of the distal tip of the needle cannula, the clip comprising a latch having at least two bends, and the clip biased by the two bends to slide over and to cover the distal tip of the needle cannula with a spring-biased blocking element to block movement of the needle cannula through an opening in the needle cannula cover, wherein the spring-biased blocking element is biased in a direction transverse to the longitudinal axis of the needle cannula and the spring-biased blocking element comprises the gate that is biased to move to the closed position to block the opening in the needle cannula cover and the spring-biased blocking element is held open by the needle cannula when the needle cannula cover is in the initial position and the intermediate position.

23. The safety needle device of claim 22, the clip mounted in the needle cannula cover adjacent the opening in a distal end in the needle cannula cover, the clip preventing the distal tip of the needle cannula from exiting the opening when the needle cannula cover is in a fully extended position.

24. The safety needle device of claim 23, wherein a first outward protrusion on the needle cannula cover cooperates with a first channel in the activation component when the needle cannula cover slides within the housing.

25. The safety needle device of claim 24, an interior surface of the housing further including a track that keys with a protruding bar on the needle cannula cover, preventing rotational movement of the needle cannula cover with respect to the housing.

26. A safety needle device comprising:

a hub having a proximal end that can be coupled to a syringe and a distal end supporting a needle cannula having a longitudinal axis and a distal tip extending from the hub;

a housing having a proximal end, a distal end, and a housing body, the hub being attached to the housing adjacent the proximal end of the housing and the needle cannula and the distal tip extending past the distal end of the housing;

a needle cannula cover comprising an elongate sleeve having a distal end having an opening therein, the elongate sleeve axially moveable in a distal direction and a proximal direction inside the housing and being biased to move in the distal direction to cover the distal tip of the needle cannula, the opening allowing the distal tip to pass therethrough when the elongate sleeve is moved in the proximal direction; and a biased clip disposed adjacent the distal end of the elongate sleeve, the elongate sleeve having a gate including a spring-biased blocking element that is biased by a biasing element to a closed position to cover the opening when the needle cannula cover is moved in the proximal direction and the distal tip of the needle cannula passes through the opening, the gate held in an open position by the needle cannula, the biasing element comprising at least two bends that provide biasing force to the gate, the needle cannula in sliding contact with a portion of the biased clip, wherein the spring-biased blocking element is biased in a direction transverse to the longitudinal axis of the needle cannula and the spring-biased blocking element comprises the gate that is biased to move to the closed position to block the opening in the needle cannula cover and the spring-biased blocking element is held open by the needle cannula when the needle cannula cover is in the initial position and the intermediate position.

27. The safety needle device of claim 26, wherein the at least two bends comprises three bends.

28. The needle safety device of claim 26, wherein the biased clip is mounted in a pocket adjacent the distal end of the needle cannula cover.

29. The needle safety device of claim 26, wherein the needle cannula cover has an initial position where the distal tip of the needle cannula is exposed and the elongate sleeve cannot move in the distal direction, an intermediate position where the needle cannula cover is moved proximally such that the distal end of the elongate sleeve is moved further from the distal tip of the needle cannula and the elongate sleeve is biased to move in the distal direction, and a final position where the distal end of the elongate sleeve extends past the distal tip of the needle cannula and the gate prevents proximal movement of the elongate sleeve and exposure of the needle cannula distal tip.

30. The needle safety device of claim 29, further comprising an intermediate component that moves axially and radially within the housing and the needle cannula cover moves axially within the intermediate component, the needle cannula cover cooperating with the intermediate component to activate the device after movement from the initial position and causing the needle cannula cover to be moved in the distal direction.

31. The safety needle device of claim 26, wherein the safety needle device is a single-use passive safety needle device, wherein the needle cannula cover automatically covers the distal tip of the needle cannula after a patient has been injected and the needle has been removed from the patient.

32. The safety needle device of claim 31, wherein a practitioner or user of the safety needle device does not have to activate the needle cannula cover by pressing a button on the safety needle device or twisting the safety needle device.

* * * * *

UNITED STATES PATENT AND TRADEMARK OFFICE

CERTIFICATE OF CORRECTION

PATENT NO. : 10,792,438 B2
APPLICATION NO. : 15/837756
DATED : October 6, 2020
INVENTOR(S) : Sanders et al.

It is certified that error appears in the above-identified patent and that said Letters Patent is hereby corrected as shown below:

In the Claims

In Claim 10, Column 32, Line 22, insert --,-- after “cover” and before “wherein”.

Signed and Sealed this
First Day of December, 2020

Andrei Iancu
*Director of the United States Patent and Trademark Office*